United States Patent
Boveja

(10) Patent No.: US 10,149,626 B1
(45) Date of Patent: Dec. 11, 2018

(54) METHODS AND SYSTEMS FOR MAPPING AND ABLATION OF CARDIAC ARRHYTHMIAS COMPRISING ATRIAL FLUTTER

(75) Inventor: Birinder R. Boveja, Greenfield, WI (US)

(73) Assignee: AMERICAN MEDICAL TECHNOLOGIES, LLC, Wau Watosa, WI (US)

( * ) Notice: Subject to any disclaimer, the term of this patent is extended or adjusted under 35 U.S.C. 154(b) by 746 days.

(21) Appl. No.: 13/595,451

(22) Filed: Aug. 27, 2012

Related U.S. Application Data

(60) Provisional application No. 61/575,736, filed on Aug. 27, 2011, provisional application No. 61/573,820, filed on Sep. 13, 2011.

(51) Int. Cl.
*A61B 5/04* (2006.01)
*A61N 1/362* (2006.01)

(52) U.S. Cl.
CPC ........ *A61B 5/04012* (2013.01); *A61N 1/3621* (2013.01)

(58) Field of Classification Search
None
See application file for complete search history.

(56) References Cited

U.S. PATENT DOCUMENTS

| | | | |
|---|---|---|---|
| 6,487,441 B1 | 11/2002 | Swanson | |
| 7,123,954 B2 | 10/2006 | Narayan | |
| 8,275,452 B2 | 9/2012 | MacAdam | |
| 2004/0059237 A1* | 3/2004 | Narayan et al. | 600/509 |
| 2004/0243012 A1* | 12/2004 | Ciaccio et al. | 600/509 |
| 2007/0055167 A1* | 3/2007 | Bullinga | A61B 5/04011 600/509 |
| 2008/0200913 A1* | 8/2008 | Viswanathan | A61B 18/1492 606/41 |
| 2009/0208079 A1* | 8/2009 | Vaillant | G06T 7/0024 382/131 |
| 2011/0125150 A1 | 5/2011 | Dino | |
| 2011/0144510 A1* | 6/2011 | Ryu et al. | 600/509 |
| 2011/0230775 A1* | 9/2011 | Barley et al. | 600/508 |
| 2012/0035488 A1 | 2/2012 | MacAdam | |
| 2012/0150021 A1* | 6/2012 | Schwartz | 600/424 |

* cited by examiner

*Primary Examiner* — Eric S Lee

(57) ABSTRACT

A method and system for cardiac mapping comprises acquiring patient's cardiac signals into a computer based system. The computer based system may be a cardiac mapping system, cardiac recording/monitoring system, or any other computer based system. The method and system comprises algorithms/programs capable of analyzing the intracardiac signals for determining at least one of locating the "zone of slow conduction", checking post-pacing interval (PPI), or checking line of block. This disclosure is useful in cardiac ablation procedures for treating cardiac arrhythmias especially atial flutters and isthmus dependent atrial flutters. The above computer based algorithms can also be activated by voice activation.

20 Claims, 46 Drawing Sheets

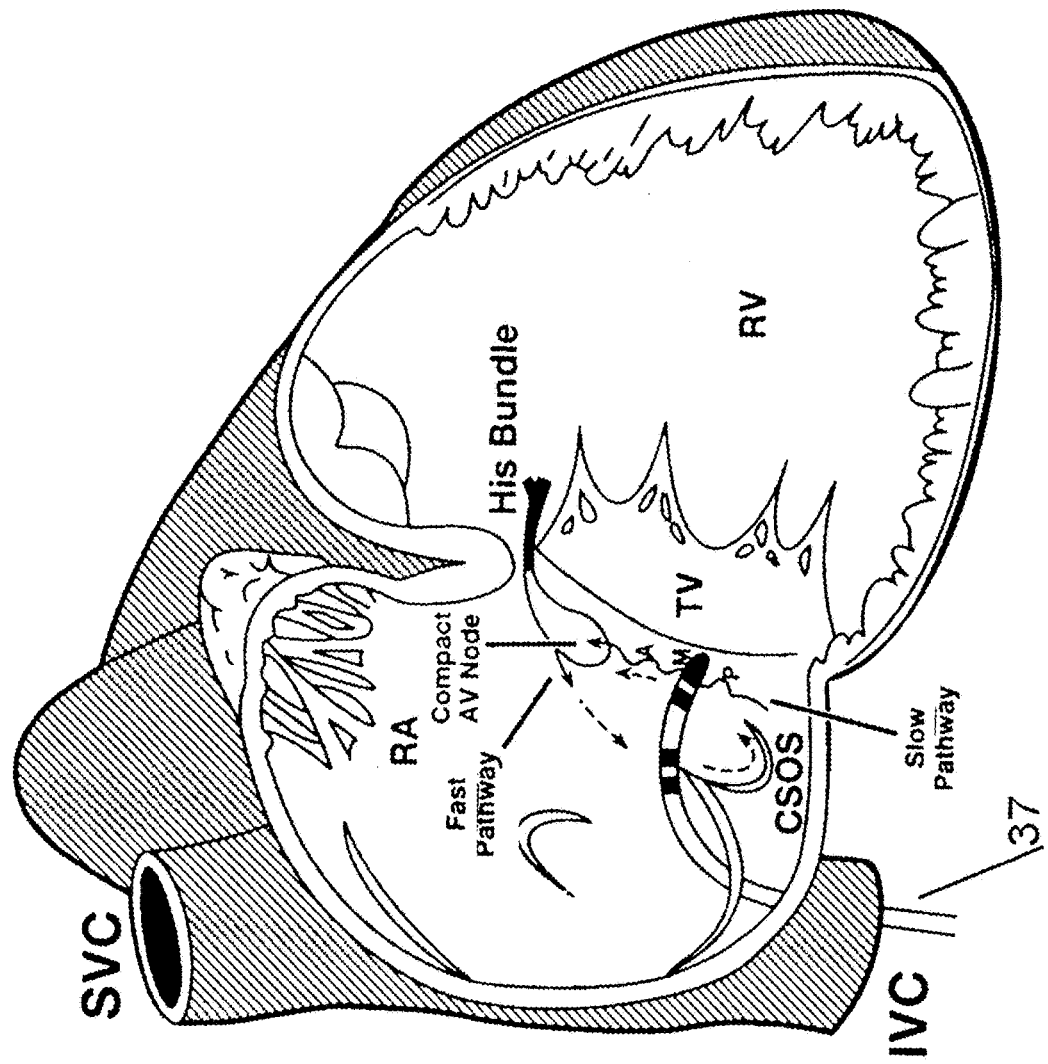

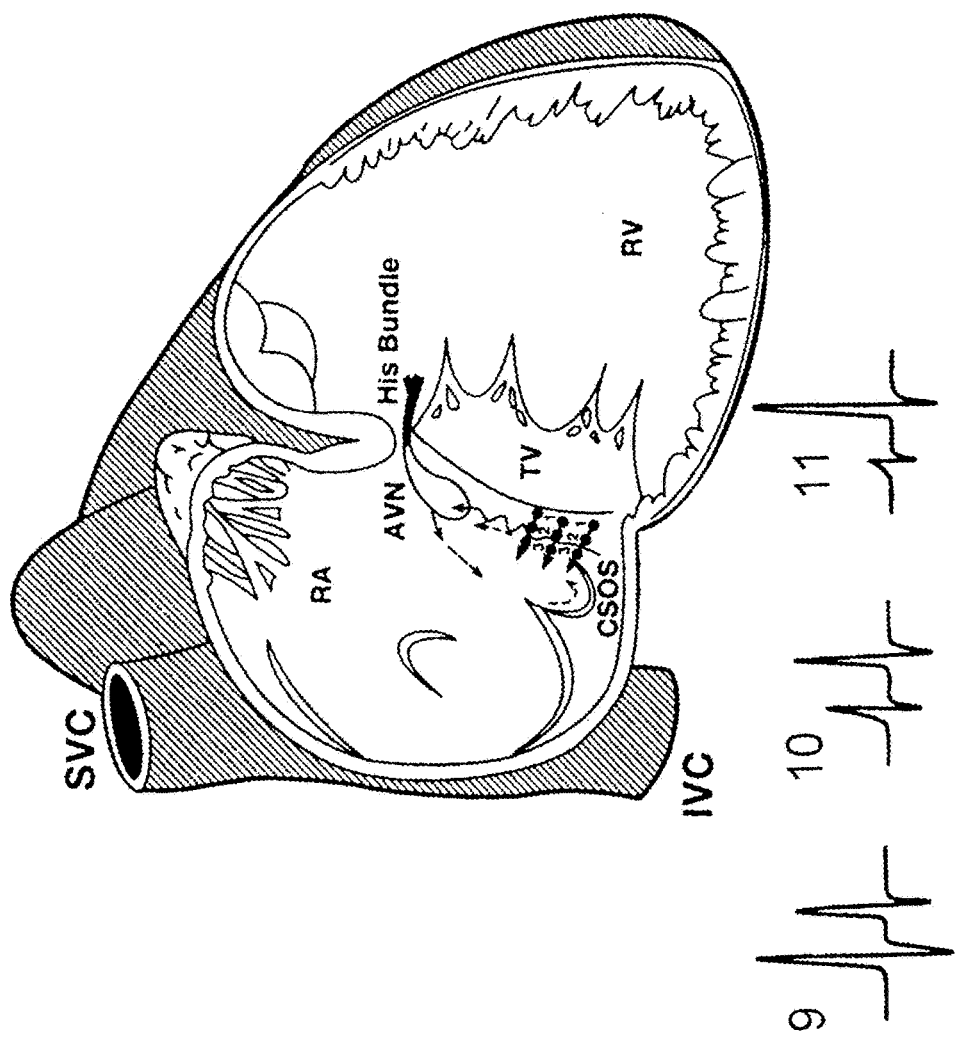

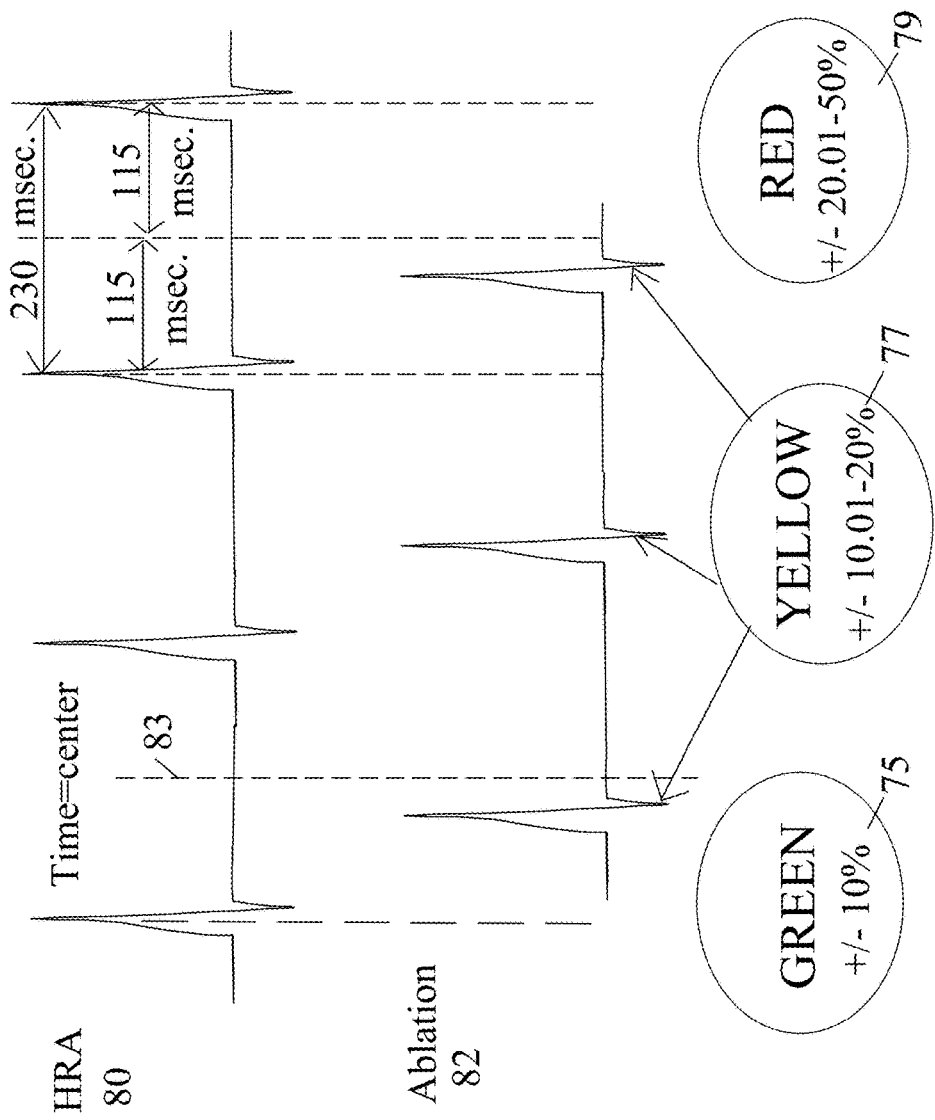

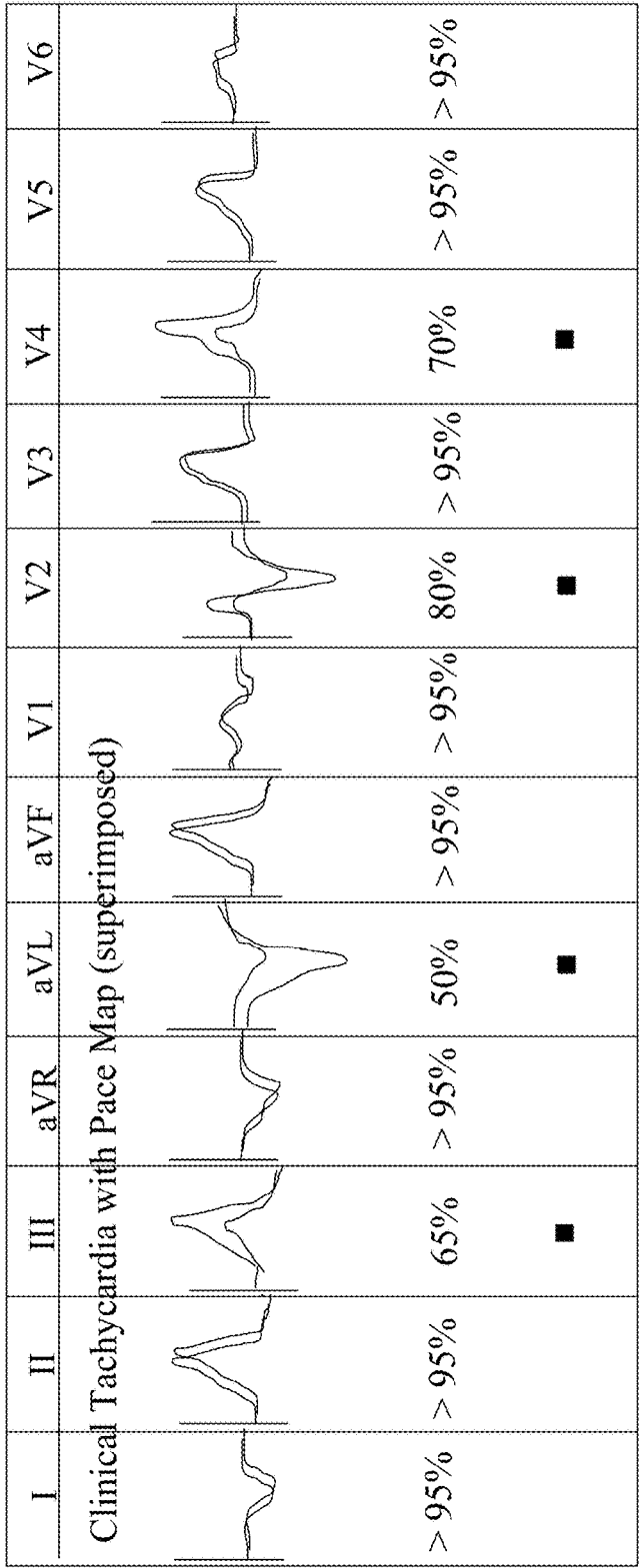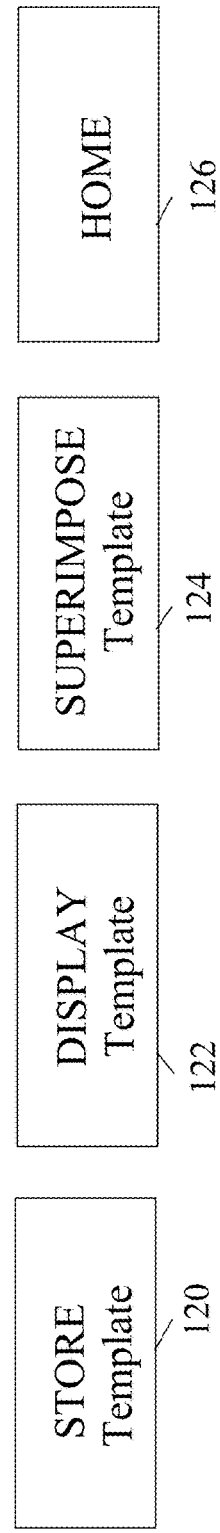
FIG. 24

FIG. 30

METHODS AND SYSTEMS FOR MAPPING AND ABLATION OF CARDIAC ARRHYTHMIAS COMPRISING ATRIAL FLUTTER

This application claims priority date of U.S. Provisional Application No. 61/575,736 filed on Aug. 27, 2011, and Provisional Application No. 61/573,820 filed on Sep. 13, 2011, which are hereby incorporated by reference in their entirety.

FIELD OF DISCLOSURE

The present disclosure relates to cardiac mapping system technology, more specifically mapping system utilizing novel methods for mapping and ablating cardiac arrhythmias.

BACKGROUND

Many cardiac arrhythmias that formerly required the use of potentially toxic drugs or cardiac surgery can now be routinely cured (or at least palliated) in the electrophysiology laboratory by means of transcatheter ablation techniques. As shown in conjunction with FIG. 1, the basic idea behind transcatheter ablation is to position an electrode catheter 37 to a critical area within the heart 52, and to apply damaging energy through the catheter in order to create a discrete scar. Strategically placed scar tissue, since it is electrically inert, can disrupt the pathways necessary for pathologic tachyarrhythmias.

Generally, for a typical ablation procedure, an EP study is performed first. Typically, in the EP study the electrical properties of the conduction system are studied, and an attempt is made to induce and study the patient's clinical arrhythmia. Once the patient's clinical arrhythmia is induced, it may be terminated with pacing or the patient may be left in arrhythmia and ablated while still in clinical arrhythmia. A 3-D mapping system is frequently used to guide the ablation procedure. The 3-D mapping system generally has the capability for 3-D reconstruction of the cardiac anatomy on a computer screen. A 3-D mapping system can be useful in some very complex ablation procedures that require computerized 3-D reconstruction, such as atrial fibrillation procedures. Examples of currently available 3-D mapping systems are Biosense Webster's Carto® mapping system, which is electromagnetic based, and St Jude's-ESI Navix® mapping system which is based on electrical impedance. St Jude-ESI also has an Array® mapping system in which a balloon is placed inside cardiac chamber.

In contrast to 3D mapping systems, EP recording/monitoring systems currently do not do 3D reconstruction of the heart. Generally, a patient in the EP Lab is also connected to an EP recording/monitoring system for performing an EP study and storing and achieving the EP Study information.

EP recoding/monitoring systems are currently manufactured and marketed by GE Healthcare—CardioLab Pruca® system, CR Bard—Lab System PRO RP®, and St Jude's EP Med Systems®.

REFERENCES AND RELATED US PATENT DOCUMENTS

How to ablate typical atrial flutter: A. Takahashi, D C Shah, P. Jais, and M. Haissaguerre, *Europace* (1999), 151-155.

U.S. Pat. No. 8,103,327 (MacAdam et al.) assigned to CR Bard, generally discloses an electrophysiology (EP) mapping system which includes an interface for operator-interaction with the results of code executing therein. In this disclosure, mapping operations can be performed without the requirement for precise catheter location.

U.S. Pat. No. 8,103,327 (Beatty et al.) assigned to St. Jude Medical generally discloses a method of representing the geometry of a portion of a heart chamber which includes positioning a catheter in a hear chamber. In the methodology the position of the catheter in the heart chamber is determined. The catheter can be re-positioned and the position is then re-determined a plurality of times to determine the geometry of at least a portion the heart chamber. A three-dimensional, anatomical representation of at least a portion of the heart chamber is then created.

U.S. Pat. No. 8,175,681 (Hartmann et al.) assigned to Medtronic Inc. generally discloses a navigation system or combination of navigation systems that can be used to provide two or more types of navigation or modalities of navigation to navigate a single instrument. A single instrument can be positioned within the patient and tracked. For example, both an Electromagnetic (EM) and Electropotential (EP) navigation system can be used to navigate an instrument within a patient.

U.S. Pat. No. 8,050,739 (Beatty et al.) assigned to Koninklijke Philips Electronics, generally discloses systems and methods for facilitating visual detection of one or more catheter tips in relation to the morphology of an anatomical structure include locating reference catheters relative to heart tissue using an automated navigation support that draws upon prominent image features that are visible in the x-ray fluoroscopy images.

U.S. Pat. No. 7,996,055 (Hauck, et al.) assigned to St. Jude Medical generally discloses a cardiac navigation system including a mapping catheter, a control system coupled to the mapping catheter, an electrode array, and means for driving an electrical current across the electrode array. The mapping catheter includes means for sensing an electrical field. The control system includes means for receiving sensed signals from the mapping catheter. The cardiac navigation system includes at least one electrode array including means for providing an electrical field across three axes. The three axes are approximately orthogonal with respect to one another. The means for driving an electrical current across the three axes includes means for providing a plurality of individual current sources to the electrode array.

U.S. Pat. No. 7,123,954 (Narayan, et al.) generally discloses an analyzes of surface electrocardiographic and intracardiac signals to identify and separate electrical activity corresponding to distinct but superimposed events in the heart. And, also uses variability in the indices from the surface electrocardiogram to indicate subtle beat-to-beat fluctuations which reflect the tendency towards atrial and ventricular arrhythmias.

U.S. Pat. No. 7,588,567 (Boveja et al.) generally discloses an apparatus and method for stopping of ablation energy delivery to tissues during cardiac ablation procedures for providing added safety.

U.S. Pat. No. 7,578,816 (Boveja, et al.) generally discloses a method and system of increasing safety of ablation of cardiac arrythmias, especially AVNRT and antero-septal accessory pathway ablations.

U.S. Pat. No. 6,658,285 (Potset, et al.) assigned to Resolution Medical, Inc. generally discloses systems, devices, and methods to localize and/or treat arrhythmias of a heart of a patient using signals sensed at an accessible body surface. Based on a database of known heart signals and associated ectopic origin sites or exit sites for treatment guidance, continuous localization identifies candidate ectopic or exit sites throughout a continuous region of tissue.

U.S. Pat. No. 6,400,981 (Govari) assigned to Biosense, Inc. generally discloses a method for mapping electrical activity of a heart including inserting a probe into a chamber of the heart, the probe including at least one position sensing device and a plurality of non-contact electrodes. Position coordinates of the electrodes are determined relative to an endocardial surface of the chamber, using the at least one position sensing device, and electrical potentials are measured at the determined position coordinates using the electrodes. Electrical potentials are computed at a plurality of points on the endocardial surface, using the measured potentials and the position coordinates, so as to generate a map of electrical activity over the endocardial surface based on the computed potentials.

SUMMARY OF THE DISCLOSURE

The current disclosure discloses novel methods and system of increasing safety, efficacy and convenience of cardiac ablation procedures for various different types of arrhythmias.

Accordingly, one objective of this disclosure is providing tools/aids for increasing at least one of effectiveness, safety, or convenience in performing cardiac ablations In one aspect the method and system of this disclosure can be incorporated into a mapping system.

In another aspect the method and system of this disclosure can be incorporated into an EP recording system.

In another aspect of this disclosure, the method and system these features can be incorporated and run via desktop computer or server.

In another aspect of this disclosure, the method and system can be incorporated and run via laptop computer.

In another aspect of this disclosure, the display of the mapping system incorporates picture-in-picture (PIP).

In another aspect of this disclosure, the display of the mapping system incorporates the fluoroscopic image in addition to the electrical signal display.

In another aspect of this disclosure, the display of the mapping system incorporates the fluoroscopic image, and additional images in addition to the electrical signal display.

In another aspect of this disclosure, the display of the mapping system incorporates digital image of the heart such as CT scan or MRI in addition to the electrical signal display.

In another aspect of this disclosure, these novel tools and features can be incorporated and run via a tablet such as the I-Pad.

In another aspect of this disclosure, these novel tools and features can be incorporated and run via a mobile device.

In another aspect of this disclosure, these novel tools can be incorporated into an existing 3-D mapping system.

In one embodiment, the method and system provides guidance for ablation in the zone of slow conduction/vulnerable portion of the circuit for atrial flutter ablations.

In one embodiment, the method and system provides visual guidance as to when the ablation catheter is in the zone of slow conduction.

In one embodiment, the method and system provides visual guidance as to when the ablation catheter is not in the zone of slow conduction.

In one embodiment, the method and system provides visual guidance as to when the ablation catheter is not in the zone of slow of conduction, but is close to it.

In one embodiment, the method and system provides visual guidance (displayed numbers) based on entrainment as to when the ablation catheter is in the flutter circuit.

In one embodiment, in the method and system the algorithms/program are configured and programmed as to automatically display the entrainment mapping numbers when the pacing from ablation catheter is stopped.

In one embodiment, in the method and system the algorithms/program are configured and programmed as to automatically display the numbers for checking for the line of block, post ablation.

In one embodiment, in the method and system the algorithms/program are configured and programmed as to automatically display the numbers for checking for the line of block, post ablation with CS pacing.

In one embodiment, in the method and system the algorithms/program are configured and programmed to automatically display the timing numbers for checking for the line of block, post atrial flutter ablation with pacing from the ablation catheter.

In one aspect of the disclosure, voice activated commands are given to activate a sequence for measuring PPI intervals.

In one aspect of the disclosure, voice activated commands are given to activate a sequence for measuring line of block with CS pacing.

In one aspect of the disclosure, voice activated commands are given to activate a sequence for measuring line of block with pacing from the ablation catheter and measuring the time to the CS catheter signal.

In one aspect of the disclosure, voice activated commands are given to activate a sequence for measuring other automated measurements.

In one aspect of the disclosure the system acquires, conditions, and analyzes timing information of atrial and ventricular intracardiac signals. Based on pre-determined timing analyses, the system being capable of electronically switching off the ablation energy.

In another aspect of the method and system, the system stops the ablation procedure by disconnecting the ablation circuit via the ground patch connection.

In another aspect of the method and system, the system shuts off ablation by turning off power of the ablation generator.

In another aspect of the disclosure, the system performs timing analysis of atrial and ventricular intracardiac signals using software selected from a group comprising, Lab Windows/CVI, LabView (National Instruments Corp.), Microsoft Visual C++, C, Dot Net framework, MATLAB, Microsoft Visual Basic.

In another aspect of the disclosure, the method and system of this disclosure may be incorporated into an ablation generator.

In another aspect of the disclosure, the method and system of this disclosure may be incorporated into an electrophysiology recording system.

In another aspect of the disclosure, the software program for analyzing intracardiac timing relationships can be modified.

In one embodiment, in the method and system of this disclosure the algorithm(s)/program(s) is configured and programmed as to automatically display the earliest activation information in real-time.

In one embodiment, in the method and system of this disclosure the software is configured and programmed as to automatically display the earliest activation information in real-time, along with earliest activation for the session.

In another aspect of the disclosure, the system contains means for EKG localization.

In another aspect of the disclosure, the system contains algorithm(s)/program(s) configured for EKG localization either automatically or interactively with the physician or operator answering questions.

In another aspect of the disclosure, the algorithm(s)/program(s) are configured such that the system measures the polarity of QRS complexes and determines automatically whether the polarity is positive, negative, or flat and stores that information in a table, which is used by the system for determining the localization or regionalization of the arrhythmia.

In another aspect of the disclosure, the system uses electrogram polarity information and one or more of area under the curve, width of the QRS complex, or amplitude of the signal.

In another aspect of the disclosure, 12-lead EKG localization is used for Atrial tachycardia, Ischemic ventricular tachycardia, Idiopathic ventricular tachycardia including RVOT and LVOT, accessory pathways including WPW, PVC mapping, and other focal or re-entry tachycardia's.

In another aspect of the disclosure, 12-lead EKG localization may be interactive with the physician or operator answering questions interactively and determining the localization information with the program.

In one embodiment, the physician or operator answers questions about the arrhythmias based on the 12-lead morphology and the program displays the answer such as the site of localization.

In one embodiment, the physician or operator answers questions about the arrhythmias based on the 12-lead morphology and the program display the answer such as the site of localization in graphical form such as a picture marked with localization.

Various other features, objects and advantages of the disclosure will be made apparent from the following description taken together with the drawings.

BRIEF DESCRIPTION OF THE DRAWINGS

For the purpose of illustrating this disclosure, there are shown in accompanying drawing forms which are presently preferred, it being understood that the disclosure is not intended to be limited to the precise arrangement and instrumentalities shown.

FIG. 5 is a diagrammatic representation of a catheter placed inside the heart (in the triangle of Koch) for AVNRT ablations.

FIG. 6 depicts the signals recorded from different locations in the triangle of Koch for AVNRT ablations.

FIG. 8B depicts schematically the positioning of the ablation catheter for ablating typical atrial flutter.

FIG. 24 shows schematically the screen for template matching for 12 leads (I, II, III, aVR, aVL, aVF, V1, V2, V3, V4, V5, and V6) and for pace mapping, where the corresponding signals are superimposed on each other.

FIG. 30 shows the question answering screen of the Ischemic VT localization program.

DEFINITIONS

EKG and ECG both refer to body surface electrocardiograms, and the terms are used interchangeably in this disclosure.

REF signal refers to a reference signal, and in the methodology of early activation mapping, the REF signal may be any one of an intracardiac signal such as a high right atrial (HRA) signal, a coronary sinus (CS) signal, or may be a body surface EKG signal.

ABL signal refers to the signal from an ablation catheter, which is used interchangeably with roving catheter, or mapping catheter, or moving catheter.

The term "software" in this disclosure is sometimes used interchangeably with algorithm(s) or program(s).

Real-time as used in this disclosure also includes near real-time

DETAILED DESCRIPTION OF THE DISCLOSURE

The following description is of the best mode presently contemplated for carrying out the disclosure. This description is not to be taken in a limiting sense, but is made merely for the purpose of describing the general principles of the disclosure. The scope of the disclosure should be determined with reference to the claims.

Figure 1:
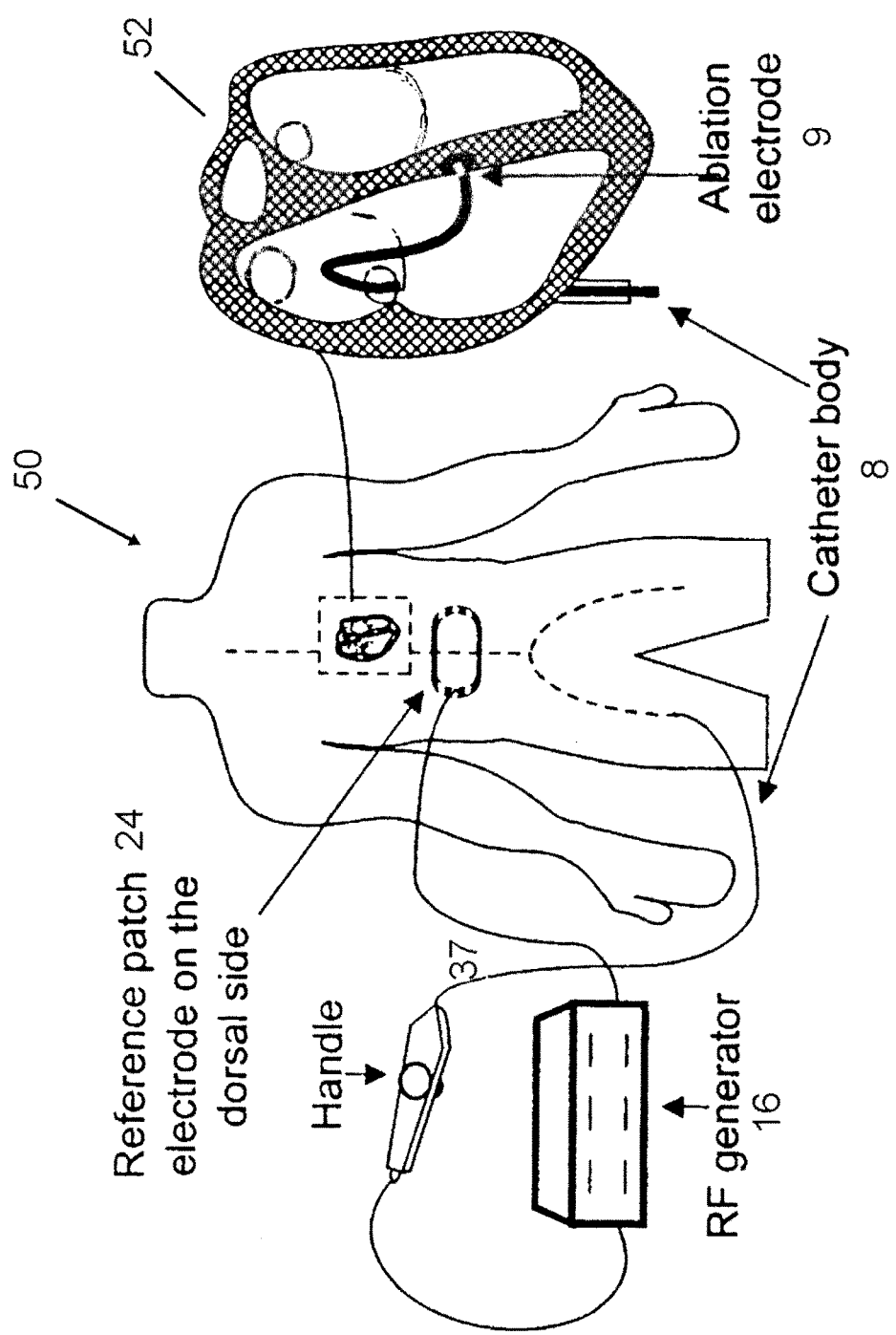
FIG. 1 depicts general concept for cardiac ablation procedures.
Figure 2:
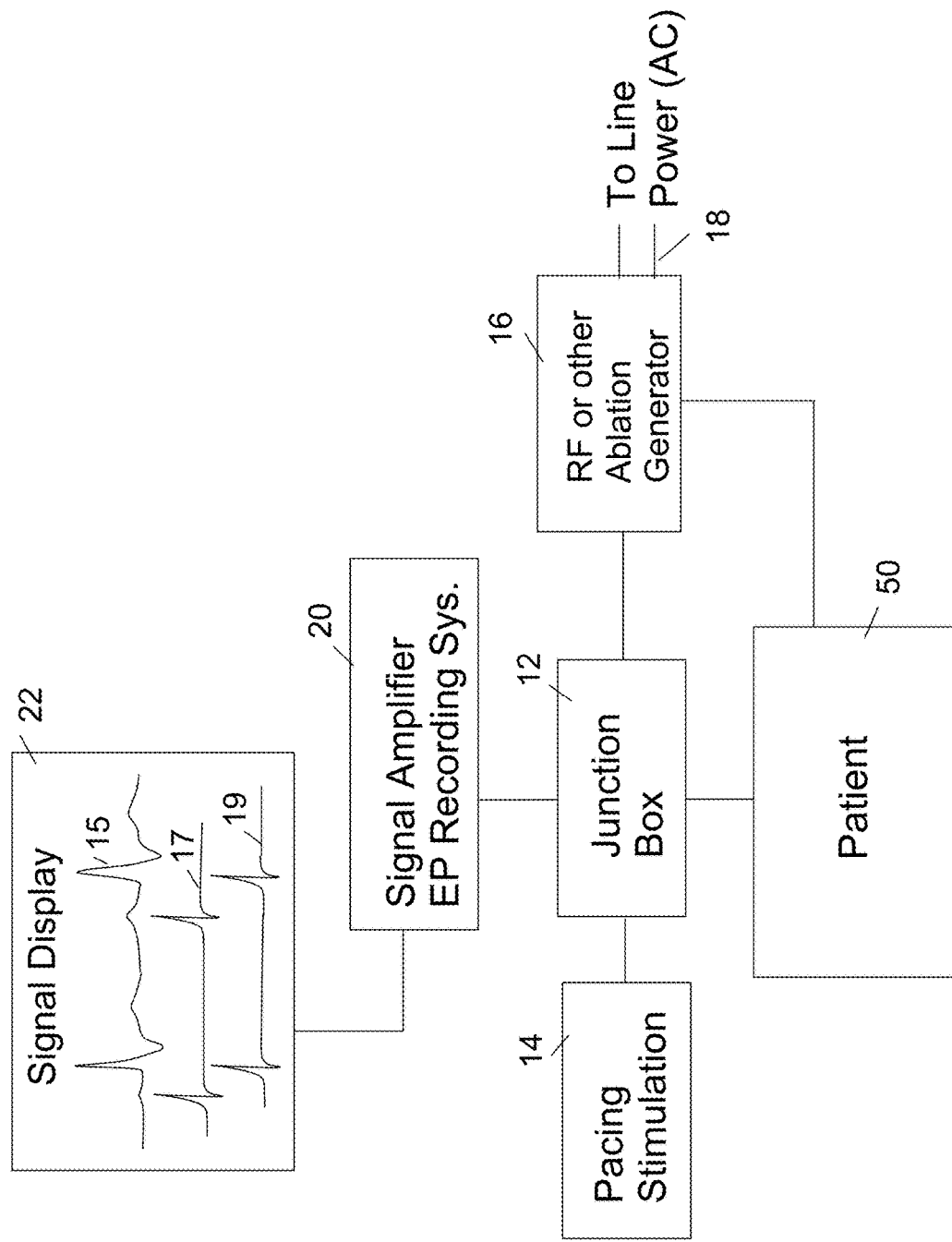
FIG. 2 depicts a general setup of cardiac ablation procedures.

For the purposes of explaining the methodology of the current disclosure, it is instructive to understand a typical setup for a generic cardiac ablation procedure. Shown in conjunction with FIG. 2 is a general setup, where body surface ECG 15 (usually 12 lead), atrial intra-cardiac (IC) signal 17, ventricular intra-cardiac (IC) signal 19, and other intra-cardiac (IC) signals such as His bundle recording and coronary sinus (CS) signals (not shown) are obtained from the patient 50, via transvenous diagnostic catheters. The catheters in the body are connected via extension cables to a junction box 12. The body surface signals are typically amplified by amplifiers of an EP recording system 20 and displayed on a display monitor 22 for easy visualization during the Electrophysiology (EP) study and cardiac ablation procedure. A pacing stimulator 14 is also connected (typically via junction box 12) for pacing of different sites within the heart such as the atrium or ventricle for example. An ablation generator 16 is connected to the patient 50. If a radiofrequency (RF) generator is used, a ground patch (or reference patch) 24 which is typically connected on patient's back (FIG. 1) is connected to the RF ablation generator, and an ablation catheter 37 which is positioned inside the heart 52 and connected to the RF ablation generator 16 via connector cables completes the circuit for ablation procedure to proceed.

Typically a physician manipulates and positions the ablation catheter 37 while being next to the patient's table, and another person operates the ablation generator 16. The ablation generator may be radiofrequency (RF), cryoablation, microwave, or other forms of ablation.

As was previously mentioned, sometimes 3-D mapping systems are used for complex ablations. The 3-D mapping systems are particularly useful for Atrial Fibrillation ablations where 3-D reconstruction of the cardiac anatomy is needed. Generally, a large percentage of cardiac arrhythmias can be ablated without the use of 3-D mapping system. Some examples of such arrhythmia's include ablations for AVNRT, atrial flutter, accessory pathway mediated tachycardias, and a group of arrythmias where ablation is based on measuring the earliest activation, such as Atrial tachycardia's (AT) and Ventricular tachycardia's (VT) for example. The tachycardia's may be normal heart VT or ischemic VT.

Figure 3:
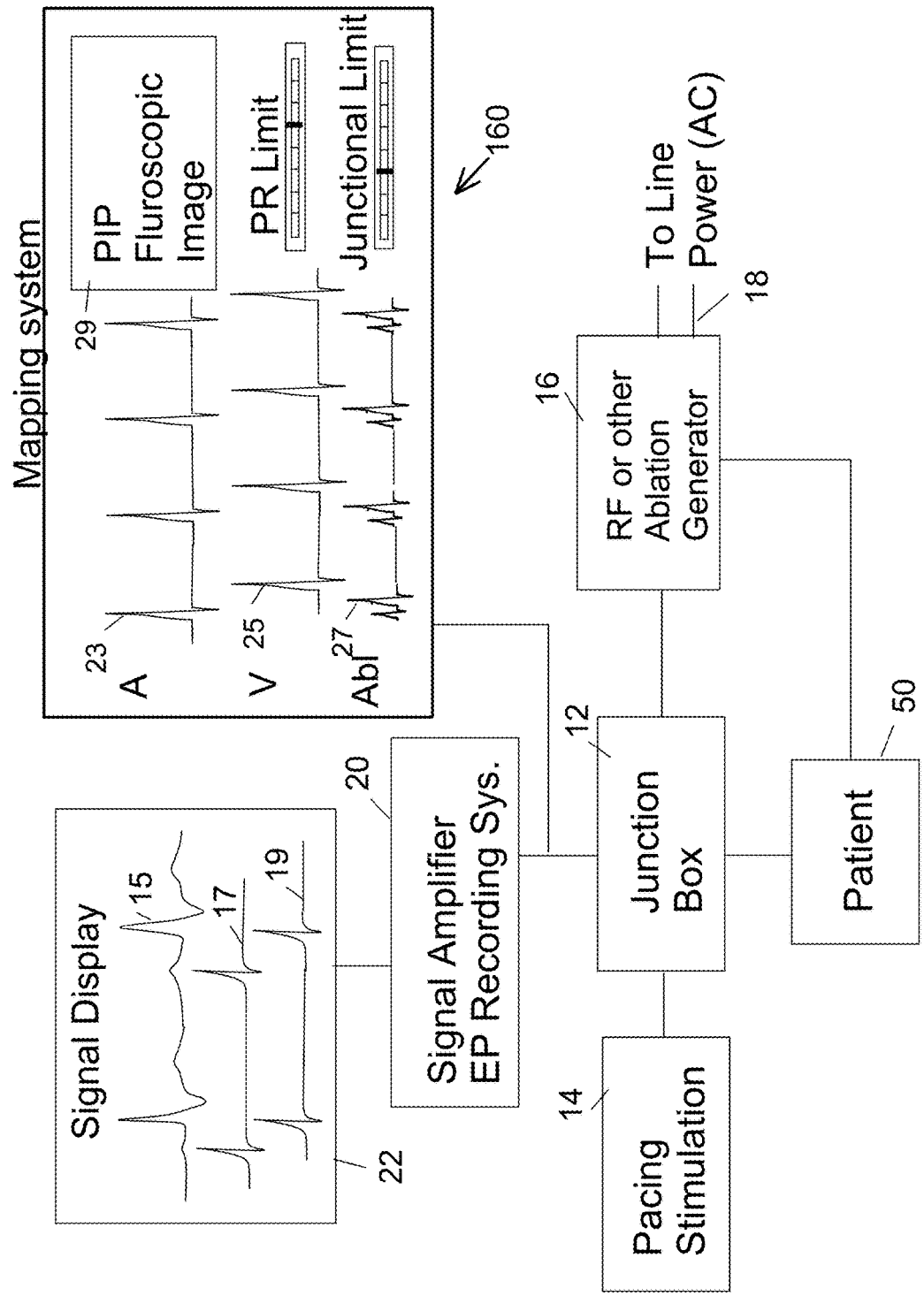
FIG. 3 depicts a general cardiac ablation setup with the addition of the mapping system 160, including picture in picture (PIP) fluoroscopic display 29.

Novel methods and system of the current disclosure can be utilized for such procedures. Shown in conjunction with FIG. 3, is a simplified block diagram showing the setup for the mapping system 160 of this disclosure which can be used as substitute for the currently available 3-D mapping systems. Since, for a significantly large percentage of cardiac catheter ablations, 3-D reconstruction by a computer is not absolutely necessary, and the mapping system of the current disclosure would be very useful and is needed.

Among the advantages of the method and system of this disclosure are,
   a) it is dramatically more cost effective whereby reducing the healthcare cost burden
   b) is simpler and easier to set-up
   c) simplifies the procedure
   d) shortens the procedure time
   e) adds to operator convenience and ease (including with automated features and voice activated commands)

Figure 4:
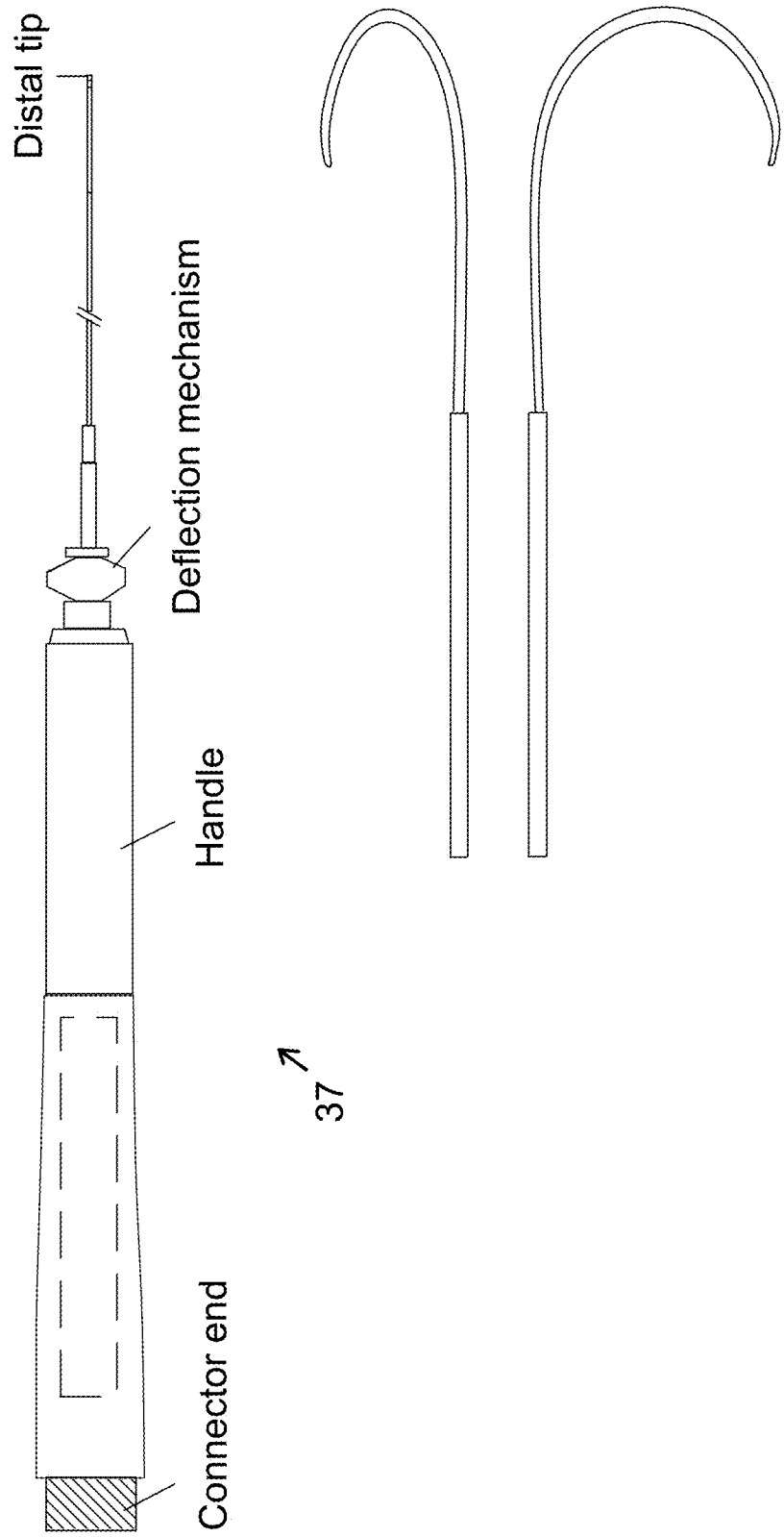
FIG. 4 is a diagrammatic representation of a generic ablation catheter.

In a typical ablation procedure, a deflectable ablation catheter such as shown in FIG. 4 is placed in a strategic location in the heart (FIG. 5), and based on the anatomic location and signal recording from the ablation catheter, the selected portion of the heart is ablated. FIG. 6 shows an example of recordings 9, 10, 11 from different regions of the heart.

Generally, the recording from the ablation catheter are analyzed in relation to recordings from other catheters in various parts of the heart which are also displayed in the mapping system and recording system. The recordings on the current mapping system of this disclosure are shown in conjunction with FIG. 6. Intracardiac electrical recording from a patient are obtained from the intracardiac catheter placed in different location of the heart, typically HRA, His bundle, CS and RV.

Figure 7A:
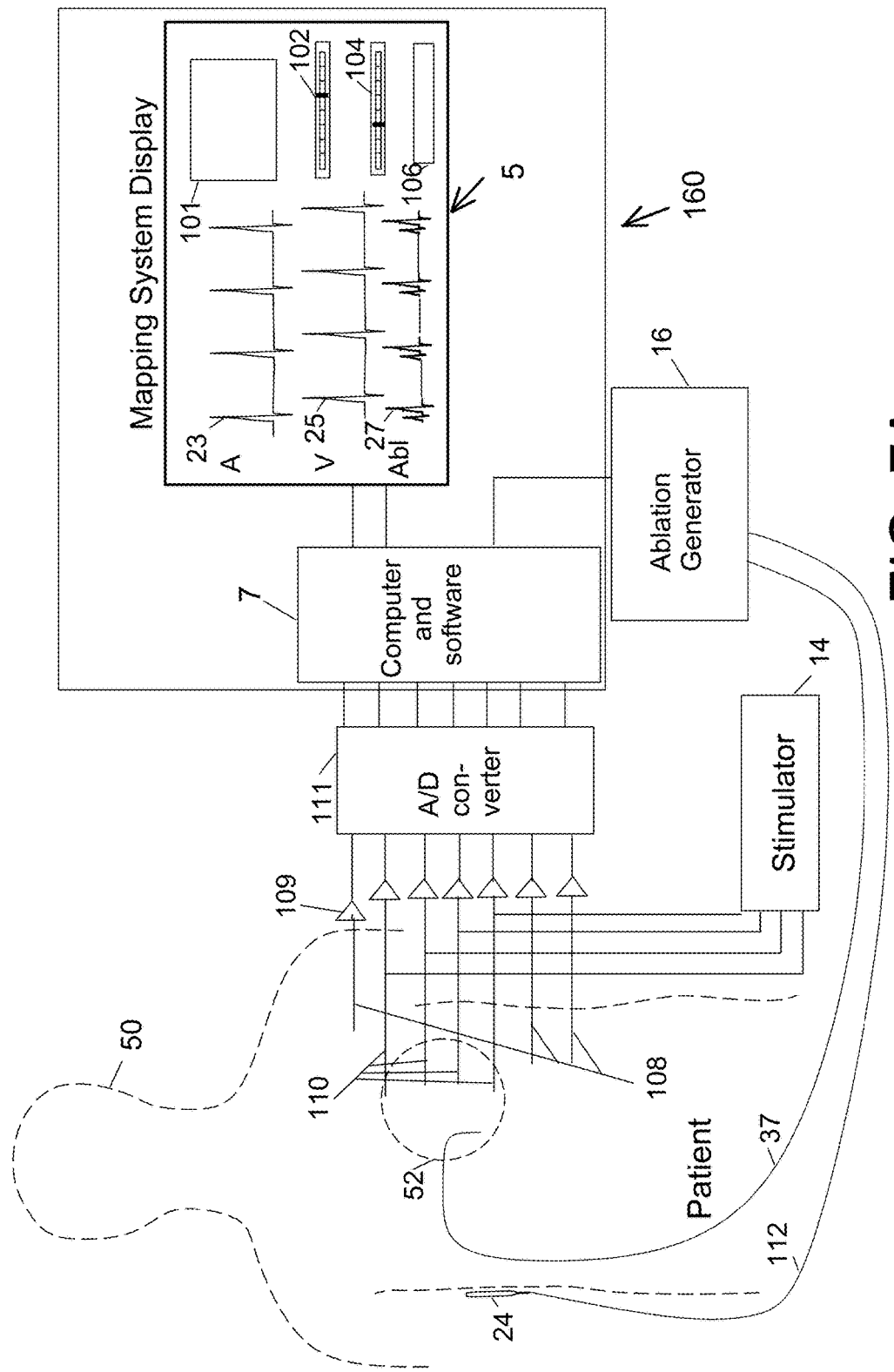
FIG. 7A is a schematic showing acquisition of signals from a patient, and the setup of the equipment in relation to the patient.

The acquisition of signals from a patient 50 into the mapping system 160 of this disclosure are shown in conjunction with FIG. 7A. As shown in FIG. 7A, cables 108 from body surface electrodes, and cables 110 carrying intracardiac signals from the heart 52 are amplified, filtered 109 and via A/D converter 111 brought into the computer 7 of the mapping system 160. The computer 7 of the mapping system 160 also comprises the which is algorithm(s)/program(s) are configured for data analysis and processing which is used for guiding the ablation procedure with the mapping system. The signals from the computer 7 are displayed on a monitor shown in FIG. 7A as mapping system display 5. The mapping system computer 7 also interfaces with the ablation generator 16, and stimulator 14 for pacing.

It will be clear to one skilled in the art that the computer 7 can be a desktop computer, a server, a laptop computer, or a tablet such as an I-Pad. It could also be a mobile device that sufficient computing power.

Figure 7B:
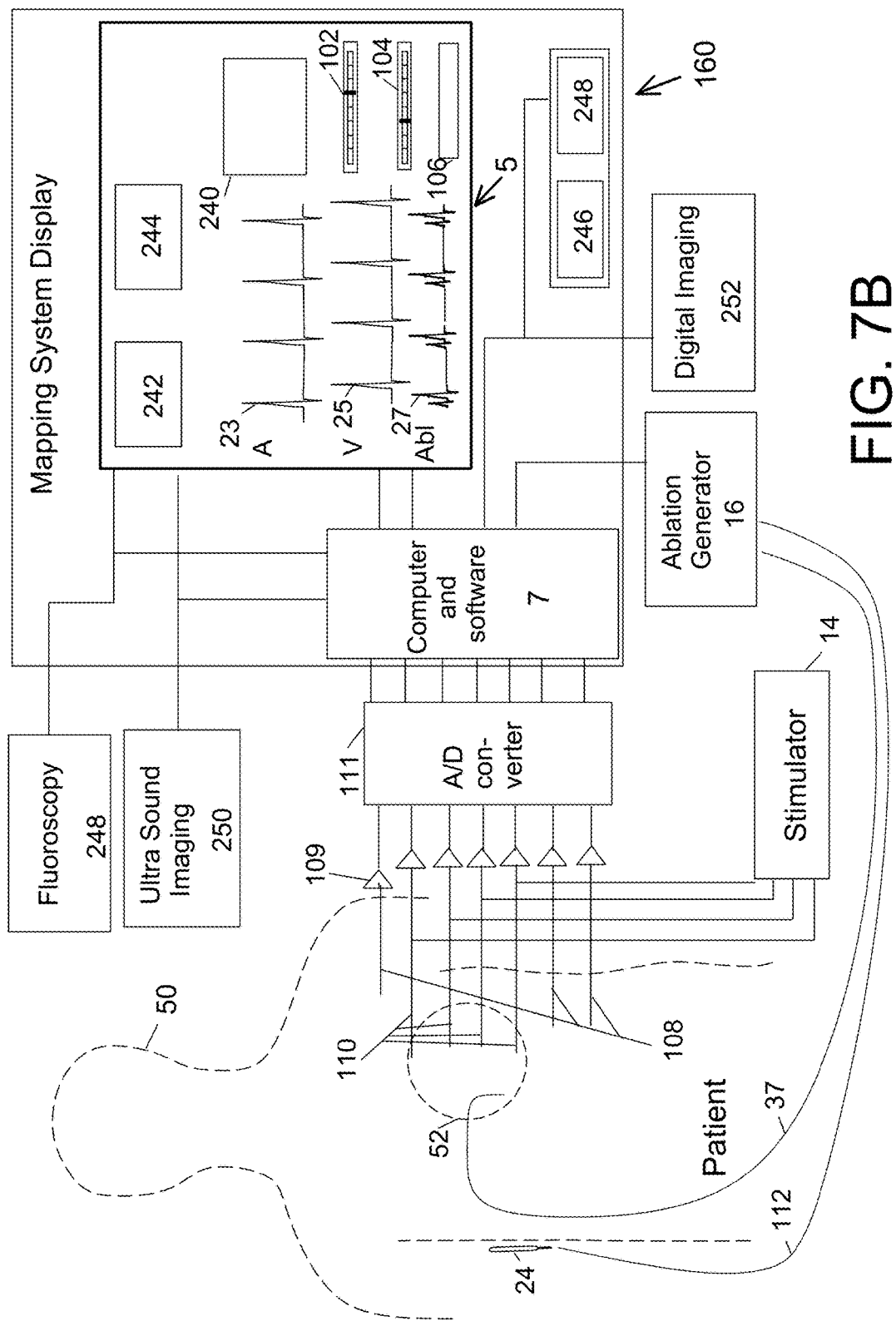
FIG. 7B is a schematic showing acquisition of signals from a patient, and the setup of the equipment in relation to the patient, including various images of the heart brought into the mapping system display.

In one aspect of the disclosure, one or more imaging display(s) may be added to the display 5 of the mapping system display. As shown in FIG. 7B, examples of these displays without limitation includes ultrasound imaging of the heart 242, ICE 244, fluoroscopic image 240 of the heart, detailed digital image of the heart such as CT 246 or MRI. Having one or more image of the heart in addition to the electrical signals is advantageous, since detailed anatomical position in addition to electrical activation or timing information is useful for making decision about the ablation site. It will be clear to one skilled in the art that detailed anatomical imaging information such as available from GE Corporation, Siemens, or Philips can be brought in the mapping system 160 display, as an aid for selecting the site for ablation.

Figure 7C:
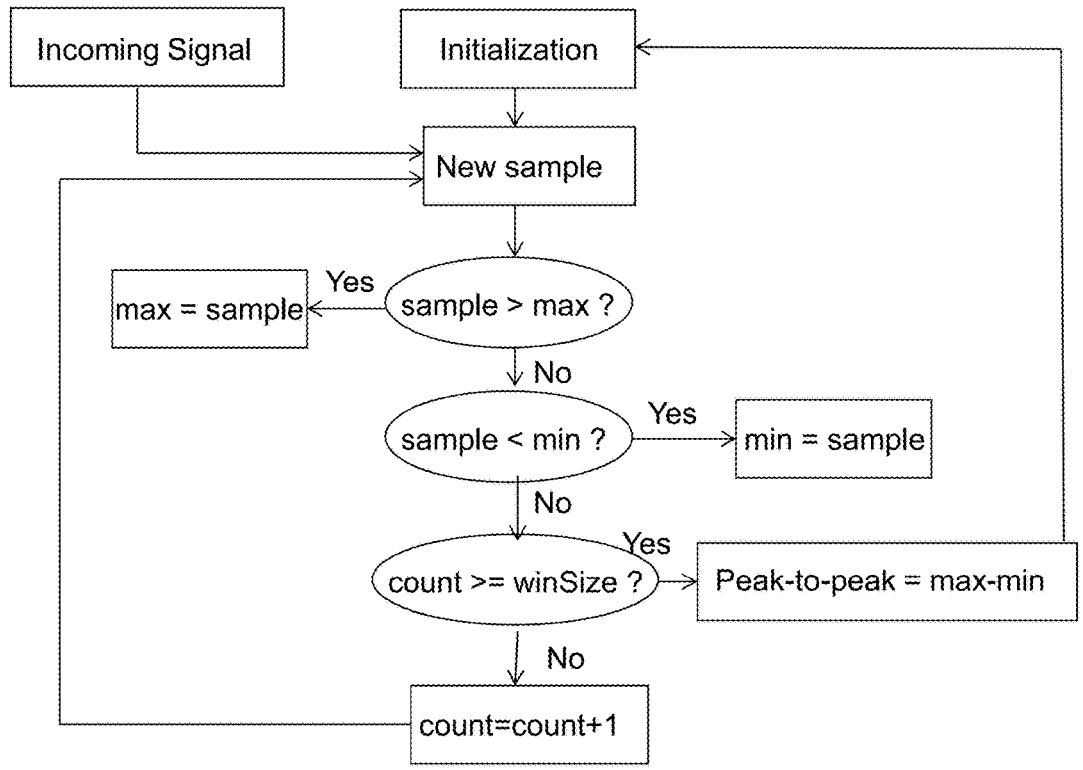
FIG. 7C is a flow diagram for algorithm to determine peak-to-peak value of each pulse, in one embodiment.

Also, as known to one skilled in the art that many different means can be utilized for signal detection by the software (after A/D conversion). FIG. 7C shows the flow diagram for one implementation for algorithm to determine peal-to-peak value of each pulse. As shown in the flow diagram the sample rate (samples/second) and the pulse rate (pulses/second) determine the Window size (winSize) within which each pulse occurs. Within this window, the maximum and minimum peaks are calculated to determine the peak-to-peak value of each pulse.

The mapping system of this disclosure 160 finds use in several different types of ablation procedures including, but not limited to, atrial flutter, AVNRT, accessory pathway, atrial tachycardia, atrial fibrillation, VT, and RVOT etc. The novel features for certain types of ablations are described below.

Use in Atrial Flutter

Several techniques have been generally described for ablation of typical atrial flutter (i.e. isthmus dependent). All have in common placing lesions in such a way that they bridge or sever a relatively narrow corridor in the low right atrium. Lesion are typically made from the tricuspid annulus directly to the IVC across the subeustachian sinus (isthmus region), or from the tricuspid annulus to the coronary sinus.

Additionally, entrainment procedure in the low right atrial subeustacian isthmus is usually or frequently performed at least once to confirm that the flutter present is indeed a "typical" variety and uses the isthmus zone as a critical element.

For entrainment mapping, the ablation catheter which is also called the mapping catheter or roving catheter is placed in the isthmus region, and paced at a cycle length (CL) which is faster than the tachycardia cycle length (TCL). Once capture is confirmed, the pacing is stopped. The first escape interval after the last paced beat is measured, and compared with the tachycardia CL. If the post-pacing interval (PPI) is similar to the tachycardia CL, then the ablation catheter is in the re-entrant circuit. If the PPI is significantly different than the TCL, then the ablation catheter is not in the circuit and some distance away from the re-entrant circuit.

Even though entrainment mapping is a very useful and sometimes essential procedure, it can be inconvenient for the electrophysiologist during the ablation procedure. Often the electrophysiologist has to break scrub to do the procedure, i.e. perform pacing measurements and measure the appropriate intervals, such as the post-pacing interval (PPI). In the method and system of this disclosure the PPI measurements are displayed on the screen and compared to tachycardia CL. This makes the cardiac ablation procedure simpler and easier.

Figure 8A:
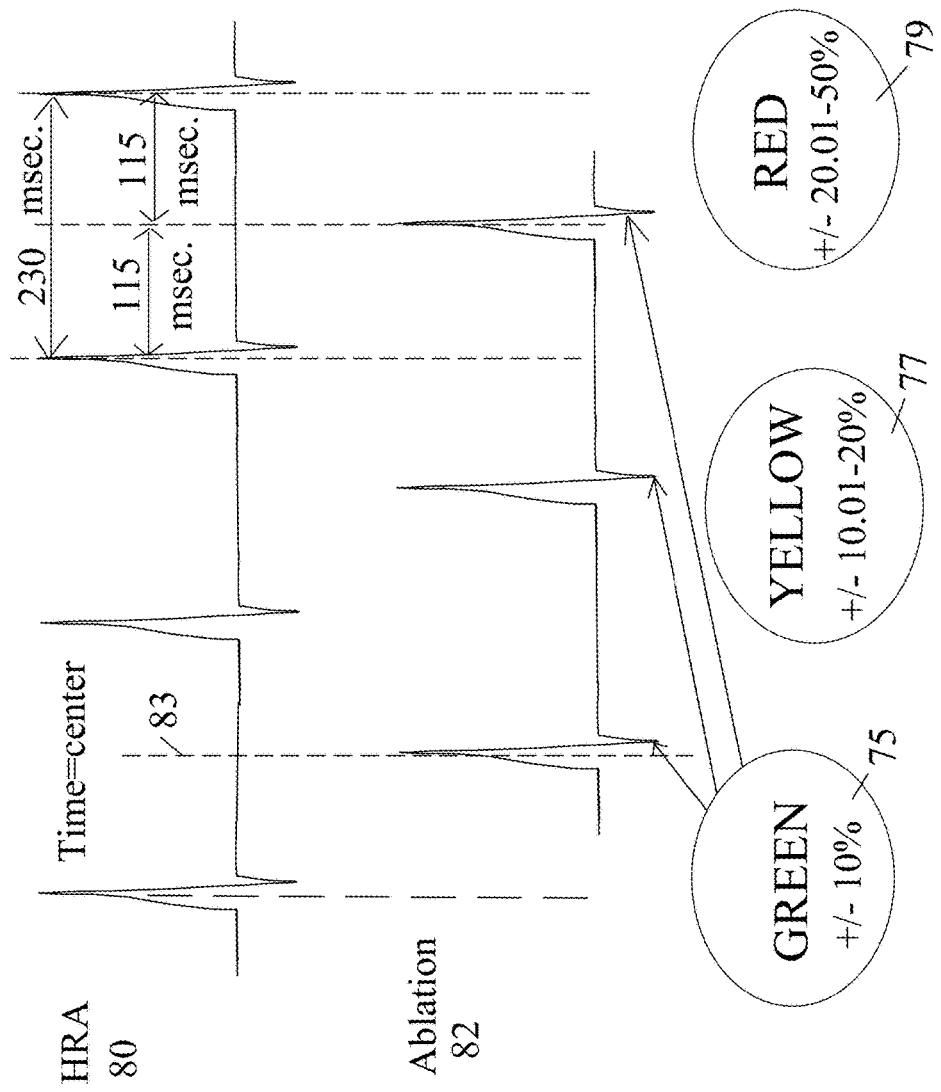
FIG. 8A depicts schematically the positioning of the ablation catheter in the center of the zone of slow conduction/vulnerable conduction in the isthmus, for ablating typical atrial flutter.

A novel feature for aiding in ablation of a typical atrial flutter procedure are shown in conjunction with FIG. 8A. In this embodiment, atrial (HRA) signals 80 and ablation (ABL) catheter signals 82 are displayed on the screen. In isthmus dependant atrial flutter ablations, it is of interest to ablate the zone of slow conduction/vulnerable portion of the circuit. In electrophysiological (EP) terms, this vulnerable portion of the circuit corresponds to when the ablation catheter signals 82 correspond in time to approximately the center of high right atrial (HRA) 80 signals. A coronary sinus (CS) signal may be used instead of HRA signal. Advantageously, the method and system of the this disclosure provides that with the computer algorithms which is configured for this in the mapping system 160 of this disclosure. As the ablation (ABL) catheter or roving catheter is manipulated by the physician, the timing of the ablation catheter signals 82 relative to the timing of HRA signal 80 keeps changing. The general aim is to have the ablation catheter (ABL) signal 82 centered 83 between the HRA 83 signals, as shown in FIG. 8A. As one tool to aid the physician, the software is configured such that when the ablation catheter signals 82 are within approximately 10-20% of the center 83 of HRA signal in time, it is an idealized site to ablate, because it is in the zone of slow conduction/vulnerable portion of the circuit. In this disclosure, this is indicated to the physician by one of various ways. In a non-limiting example, a green light 75 (shown at the bottom of FIG. 8A) goes ON indicating the desirability to ablate at this site, because this site corresponds to the zone of slow conduction/vulnerable portion of the circuit. In one embodiment, the signal itself may change color. The desirability to ablate at this site, can be shown in any number of ways, which are all considered within the scope of this disclosure.

Similarly, as the ablation catheter 82 is moving (from the center) it may be within 10-20% of the center of HRA 83, in which case the yellow light goes on, or the ablation catheter signal 82 turns yellow (shown in FIG. 8B). This indicates to the physician that the desirability of this ablation site is not as good as when the green light 75 is on, but is better than when the red light 79 is on. Again, this "in the middle" situation can be depicted in one of various ways, and any of these ways are considered within the scope of this disclosure.

Figure 9:
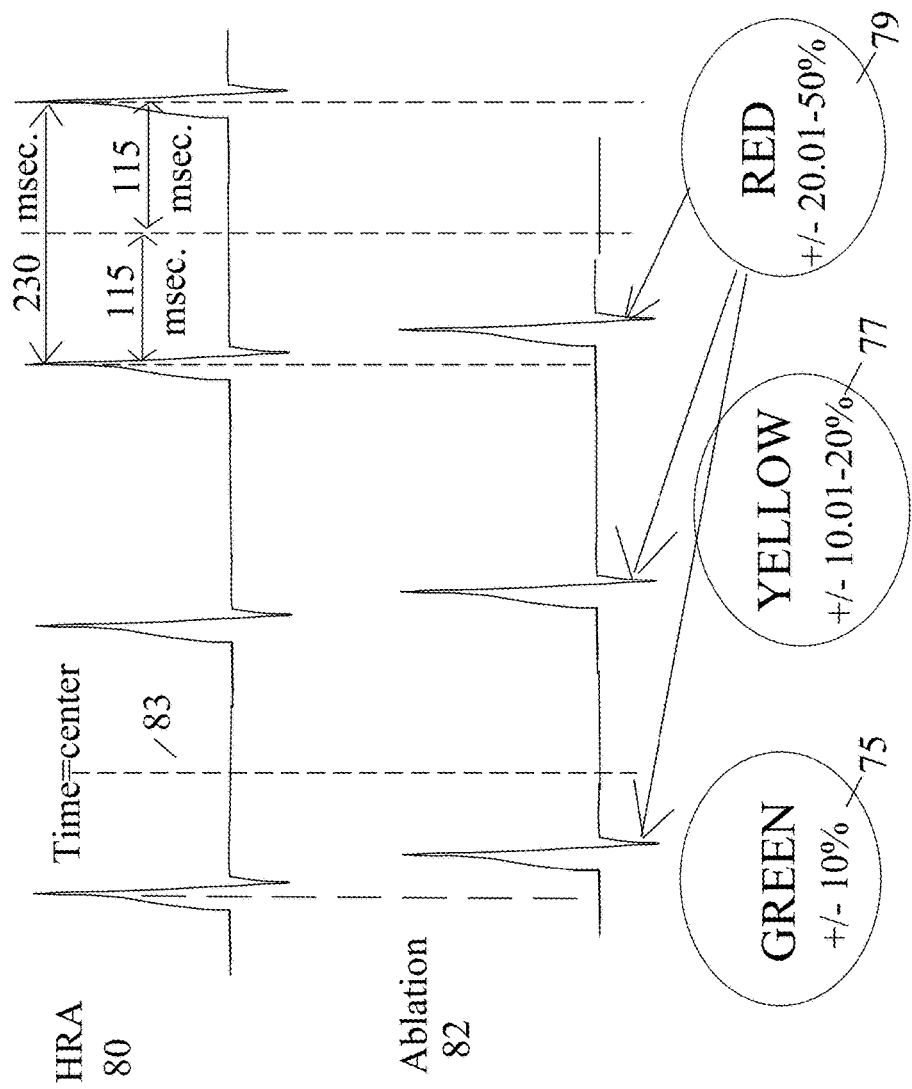
FIG. 9 depicts schematically the positioning of the ablation catheter for ablating typical atrial flutter, where the site of ablation is not desirable.

As the ablation catheter 82 is manipulated, the situation where the ablation catheter is off the center mark, i.e. away approximately 20-50% from the center point 83, which induces the red light 79 to go on, indicating to the physician that the desirability of ablating at this site is not high, and the ablation catheter 82 should probably be manipulated to a better spot or site for ablating. This situation is depicted in FIG. 9. As mentioned previously, this non-centering can also be indicated in various other ways in the method of this disclosure. For example the signal itself may turn red, or the color around the signals may turn red indicating the undesirability of ablation at this site.

It will be clear to one skilled in the art that various different software programs may be used to code these algorithm(s)/program(s), of this disclosure. Program code can be written using one of several commercially available software packages. The software that can be used for this purpose includes, but is not limited to Lab Windows/CVI, LabView (National Instruments Corp.), C+, Microsoft Visual C++, Dot Net framework, MATLAB, and Microsoft Visual Basic, Phython among others. Use of these or other functional languages for this purpose that are available now or developed in the future, is considered within the scope of the disclosure. In coding and configuring the software, the timing can be taken (T=0) from the point of signal detection in the CS and ABL catheter. Signal detection can be from simple threshold detection to more sophisticated peak detection algorithms, as long as it consistent to both CS (or HRA) and ABL signals. The formulas for line coding in C++ or VI's in Labview are well known to one of ordinary skill in the art.

Testing of applicant's prototype has been performed using both Microsoft visual C++, LabView and MATLAB.

Frequently, before starting atrial flutter ablation, entrainment mapping is performed. Sometimes, ablation is started and when it is not successful entrainment mapping is performed during the procedure. Advantageously, in the method and system of this disclosure, entrainment mapping is programmed and configured by the software in the computer system to make it convenient for the physician performing the procedure, and to make the procedure go faster and smoother. Entrainment involves pacing from multiple, separate sites within the right atrium at cycle lengths of 10-20 ms faster than the tachycardia cycle length (TCL), observing its effect on flutter wave morphology and estimating proximity of pacing site to tachycardia circuit by analysis of the post pacing interval (PPI). Generally, the pacing site is considered to lie within the tachycardia circuit when the post pacing interval (PPI) is within 30 msec of the tachycardia cycle length (TCL). Entrainment from sites which are outside the flutter circuit will demonstrate manifest fusion on the surface ECG and the PPI will exceed the flutter cycle length (FCL) by more than 30 msec.

Figure 10:
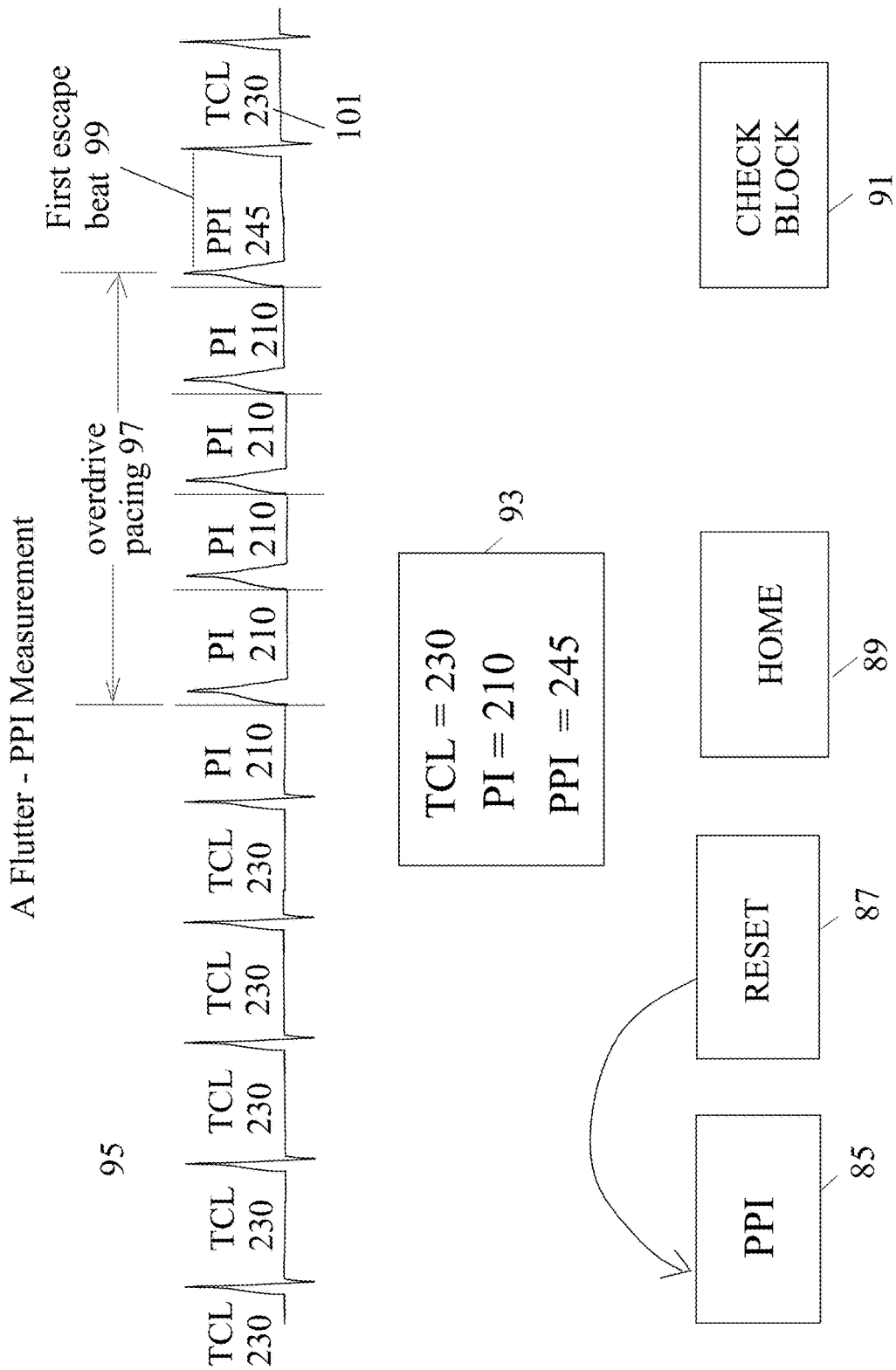
FIG. 10 shows schematically the screen for automated PPI measurements for flutter ablations.

In the method and system of this disclosure, PPI measurement is configured and programmed as is shown in conjunction with FIG. 10. As shown in the bottom portion of FIG. 10, there are three buttons labeled PPI 85, Reset 87, and Home 89. To start the PPI measurement, the PPI button 85 is pressed. This starts the program software to do the PPI measurement analysis which algorithm is configured within the program. When the PPI button 85 is active, the program starts displaying the tachycardia cycle length (TCL) 95 on the screen, as is shown in the top of the figure. In this example, without limitation, the tachycardia cycle length (TCL) is 230 msec, and the pacing interval (PI) is 210 msec. As the pacing is started at a faster rate than the tachycardia rate, the software is configured and programmed to recognize this, and a pacing sign 97 is displayed, as is shown in the top center of the figure. This is recognized by the program because the pacing rate is faster than the TCL 95. The software is programmed and configured to recognize these changes in the rate. As soon as the pacing is stopped, the rate drop is picked up by the computer software, which freezes the screen and displays the measurements on the screen. The displayed measurements 93 include values for TCL, PPI, and PI. The PPI interval is the time interval between the last paced beat, and the first escape beat. In this example it is 245 msec. After that the tachycardia interval ensues, which in this example is 230 msec. In one embodiment, the coding may be based on rate alone. In another embodiment, the coding may be based on rate and/or other parameters. For example, when the pacing is started, not only is rate faster, but the initial voltage is also higher due to the large pacing spike. This may be taken advantage of when coding.

In one embodiment, when the reset button 87 is pressed, the software goes into a mode where it is ready to repeat the PPI measurements again, and starts displaying the TCL 95 numbers on the screen. When pacing is turned on and stopped, the PPI measurement is displayed again. PPI measurements may frequently be repeated several times during the flutter ablation procedure. When the last PPI measurement is completed, the Home button 89 (shown on the bottom of the screen) is pressed, which takes the program out of the PPI measurement program and back into the main flutter program.

It will be clear to one skilled in the art, that this methodology can be used for both typical (i.e. isthmus dependent flutter) or atypical (i.e. non-isthmus dependent flutters).

During the course of the procedure, ablation lesions are performed in the usual manner. After completing the lesions, the line of block is always checked, either in the unidirectional of bidirectional manner. Advantageously, in this disclosure the procedure for checking the line of block is also configured and programmed by the software and is shown in conjunction with FIGS. 11-13.

Figure 11:
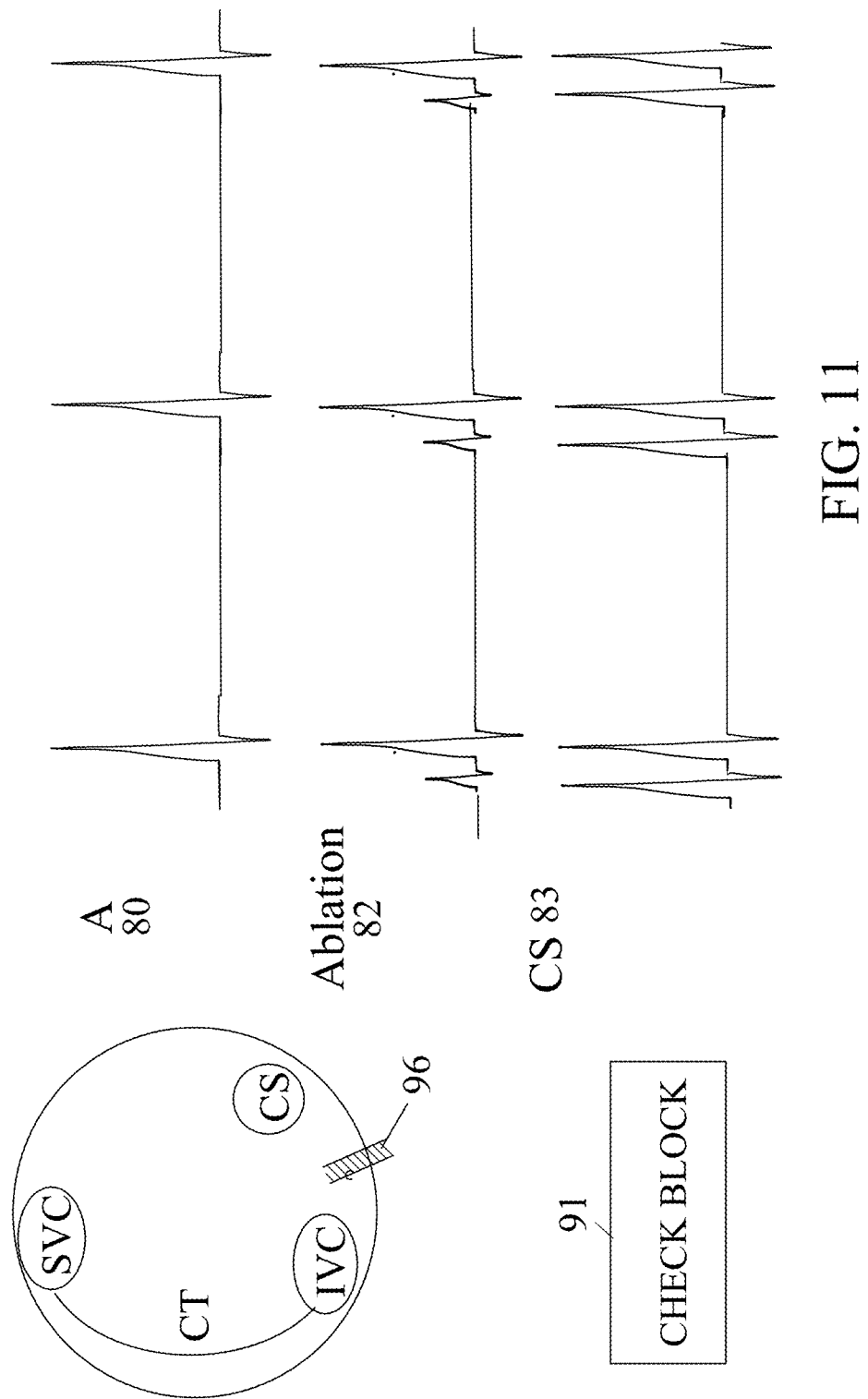
FIG. 11 shows schematically the screen for automated measurements for checking for line of block after completing a flutter ablation line.
Figure 12:
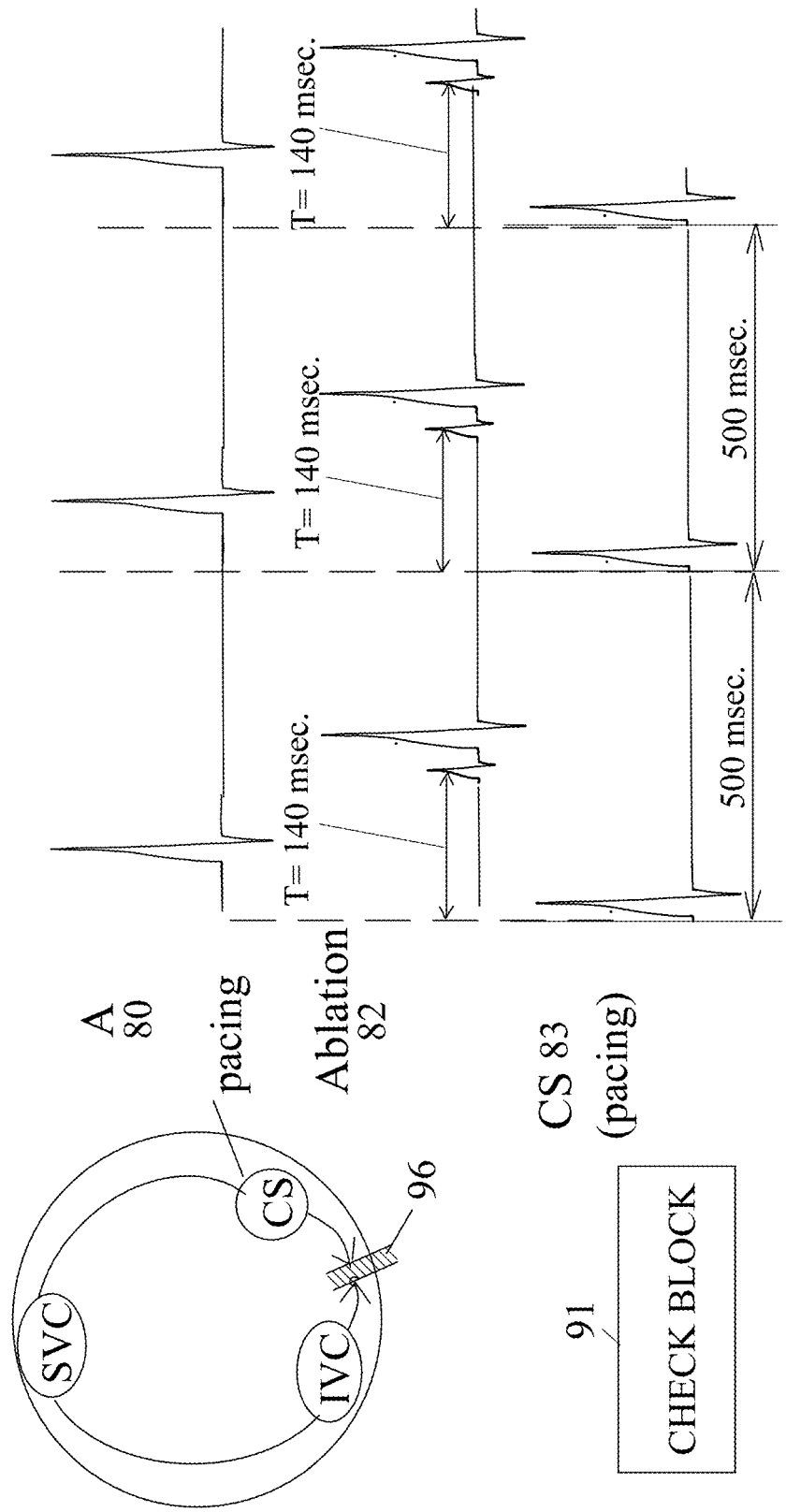
FIG. 12 shows schematically the screen for automated measurements for checking line of block with CS pacing and the ablation catheter on the other side of "ablation line".

As shown in conjunction with FIG. 11, three or more channels of information is displayed on the monitor including that of the atrial catheter (A) 80, ablation (ABL) catheter 82, and coronary sinus (CS) catheter 83. Generally, post ablation line of block can be checked by pacing through the CS 83 catheter and recording the time to the ABL catheter signal 82, or by pacing through the ABL catheter 82 and measuring the time to the CS catheter 83. Advantageously, in the method and system of this disclosure, the software in the computer is configured and programmed such that these measurements are also displayed conveniently to make the procedure go faster and smoother. To check for line of block in the clockwise direction, as shown in conjunction with FIG. 12, the Check Block box 91, shown in lower left corner of the figure is activated. As pacing is performed from the CS 83 catheter, the software is configured and programmed such that the measurement of time from the pacing spike (CS catheter) to the ABL 82 signal recording will be measured by the software and displayed on the screen. As previously mentioned, one of any number of software may used for coding for this purpose. This makes it convenient and faster for the physician performing the ablation procedure. As shown in FIG. 12, in this example the time from the pacing spike (CS 83) to the ABL signal 82 is 140 msec.

Figure 13A:
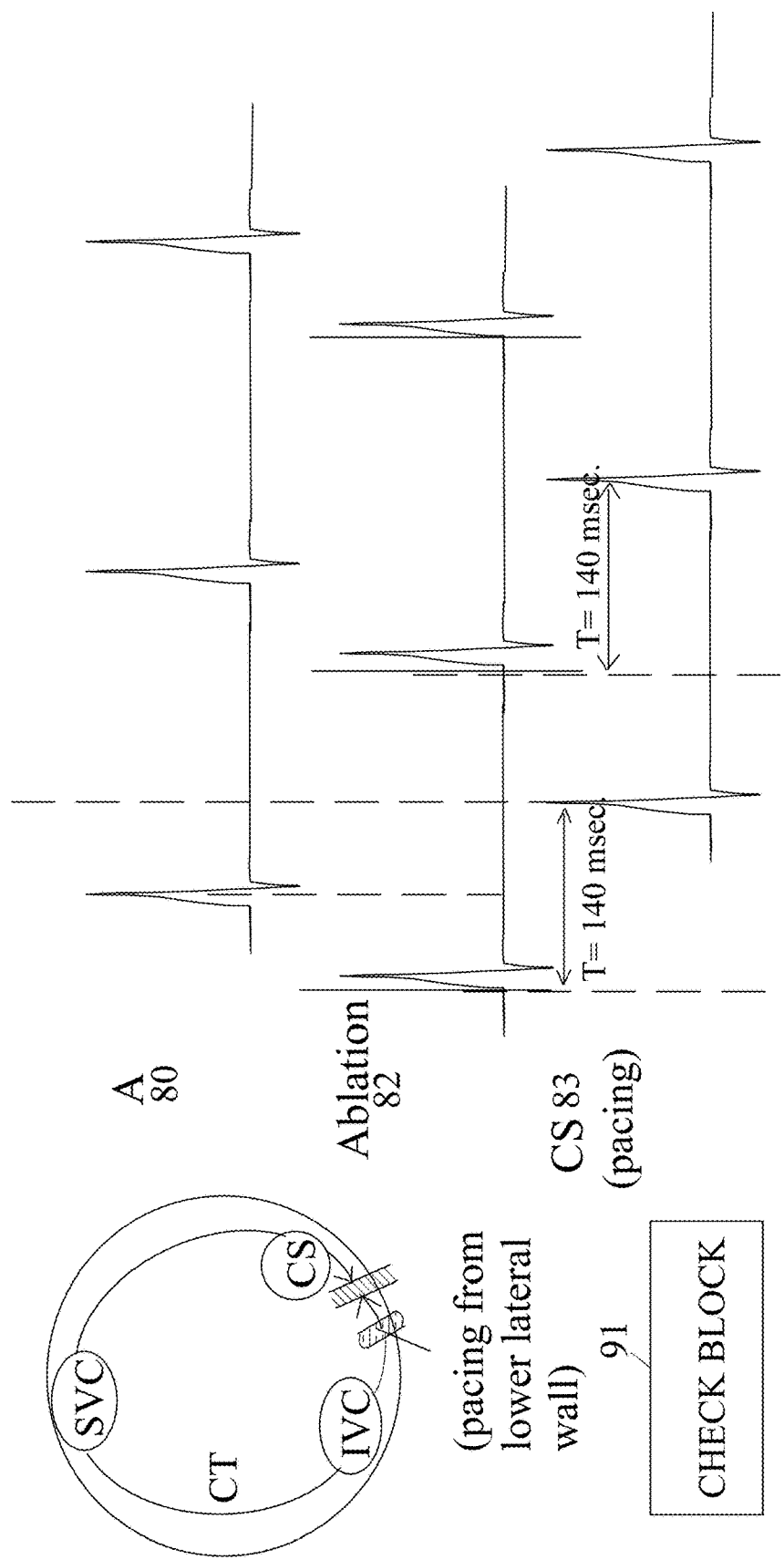
FIG. 13A shows schematically the screen for automated measurements for checking line of block with pacing from the ablation catheter (low lateral position) and the CS signal being on the other side of "ablation line".

Similarly, checking for line of block in the counterclockwise direction is shown in conjunction with FIG. 13A. In this case, the pacing is performed from the ABL 82 catheter, and time is measured from the pacing spike on the ABL 82 signal to the time on the CS signal 83. As shown in the example in this figure the time is also 140 msec.

After the measurements are completed, the software is configured such that by clicking on the Check Block box 85 again takes the program back to the main atrial flutter menu.

Figure 13B:
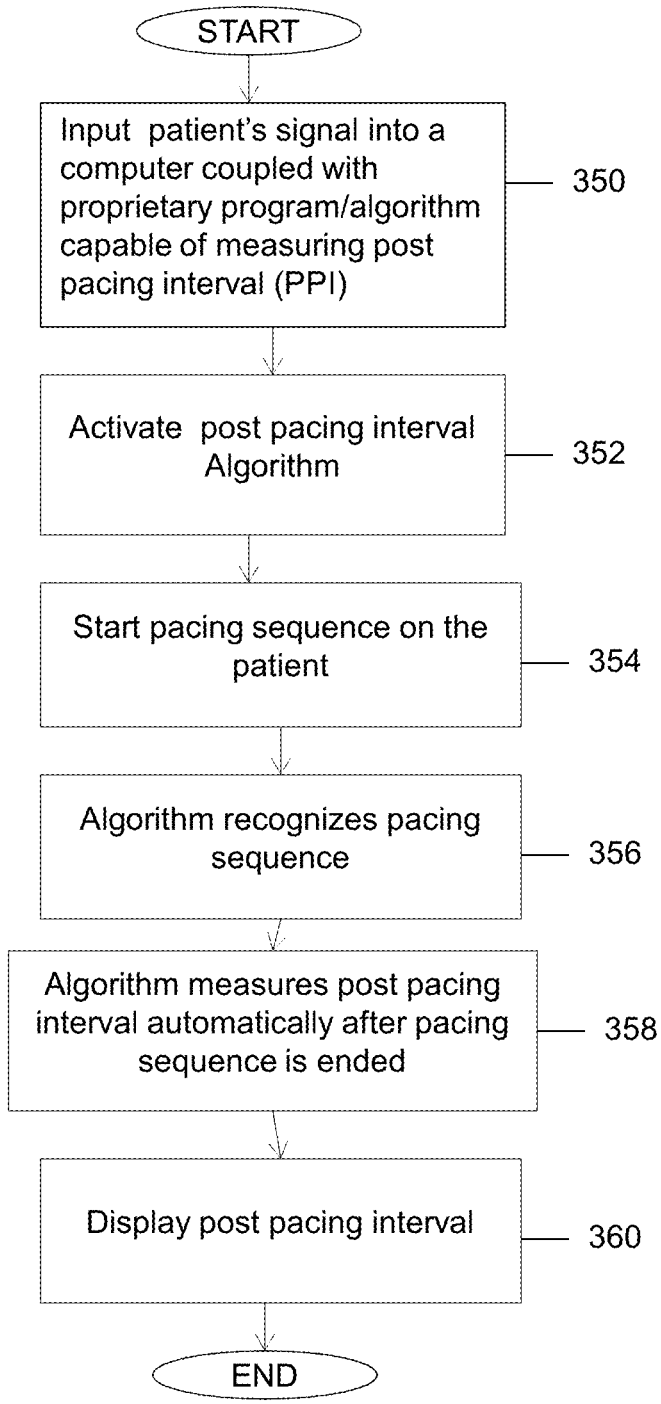
FIG. 13B is a flow diagram showing sequence for measuring and displaying PPI.

Flow diagrams 13B, 13C, and 13D explain the flow of the procedure for the methodology for atrial flutter. Flow diagram in FIG. 13B show the procedural flow for measuring post-pacing interval (PPI) which is automated in the method and system of this disclosure. As shown in conjunction with FIG. 13B, patient's signals are acquired into a computer system which comprises software configured and programmed for automated PPI analysis. PPI measurement is used to determine if the location of the ablation catheter is within the arrhythmia circuit. It generally involves pacing into the arrhythmia at a rate slightly faster than the tachycardia rate for a few beats. When the pacing is stopped, the time between the last paced beat and the first escape interval (PPI) is measured. If this time interval is similar to the tachycardia cycle length (TCL) then the ablation catheter is in the circuit of the tachycardia. If the post pacing interval (PPI) is much larger than the TCL, then the ablation catheter is not in the circuit.

In conjunction with FIG. 13B, when the ablation catheter is placed at the appropriate position, the post-pacing interval algorithm is activated (block 352). The pacing sequence is started either manually using the stimulator, or via voice activation. The algorithm recognizes the pacing sequence (block 356), and when the pacing sequence is completed, the algorithms measures and displays the post-pacing interval (blocks 358 and 360). If the PPI shows that the catheter is in the flutter circuit, then the physician may start the ablation process.

Figure 13C:
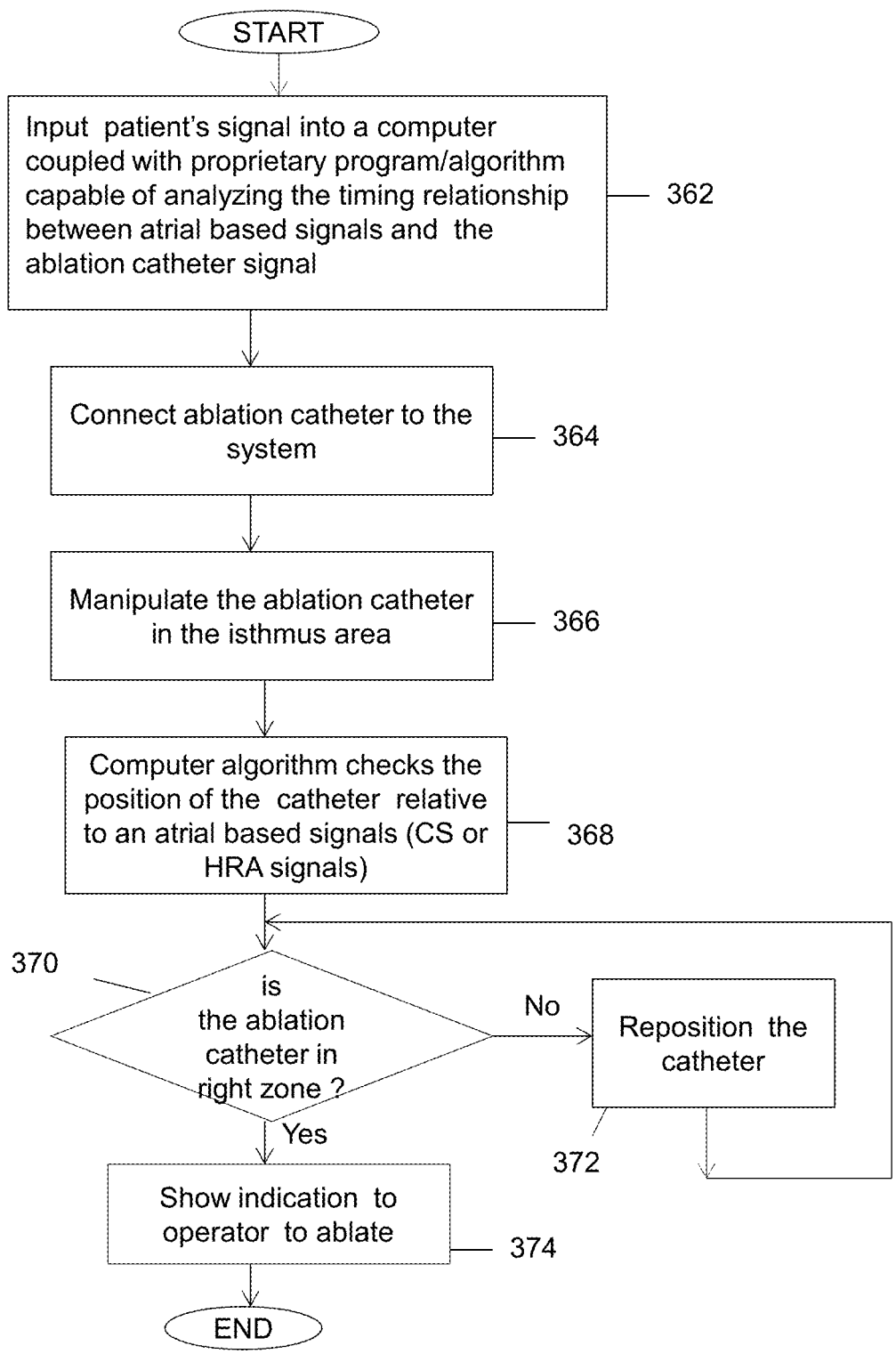
FIG. 13C is a flow diagram showing sequence for measuring "zone of slow conduction".

Shown in conjunction with FIG. 13C is the ablation process where the computer guides the physician to the zone of slow conduction. Once the ablation catheter is connected to the system (block 364), the physician manipulates the ablation catheter in the isthmus area (block 366). The algorithm guides the physician if the catheter is in the zone of slow conduction (block 370). The physician may ablate if the catheter is in the right position, or may re-position the catheter (block 372). Once the ablation lesions are completed the physician is ready to check for the line block which is shown in the flow diagram in FIG. 13D.

Figure 13D:
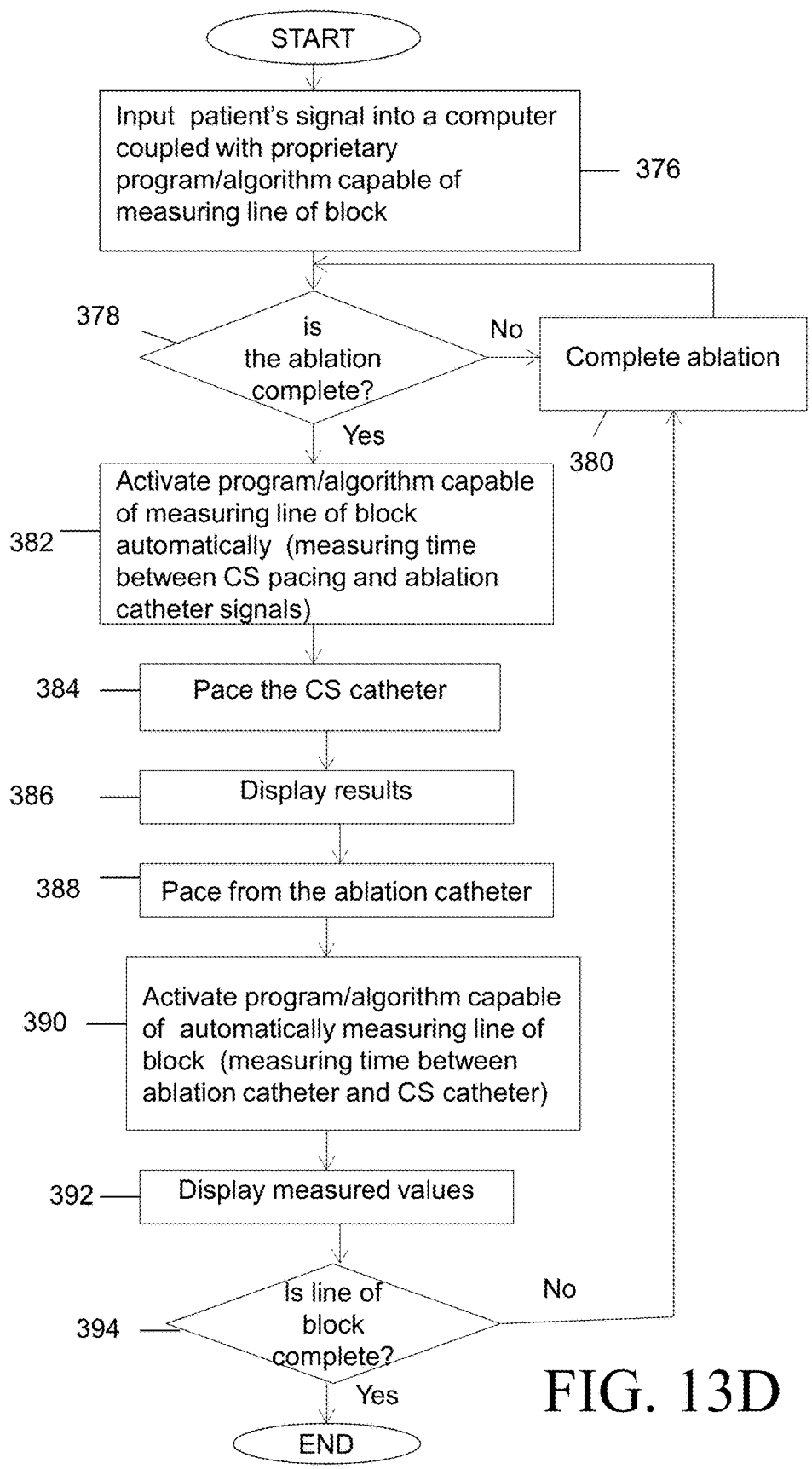
FIG. 13D is a flow diagram showing sequence for checking line of block.
Figure 13E:
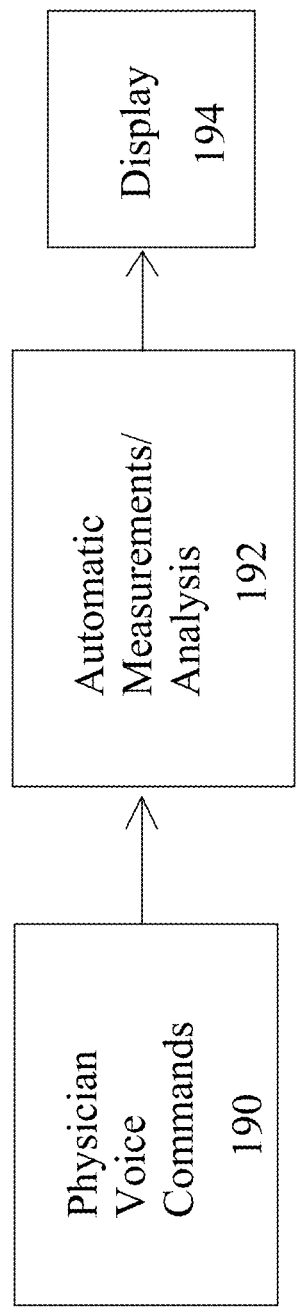
FIG. 13E is a block diagram of the general concept for voice activation.
Figure 13F:
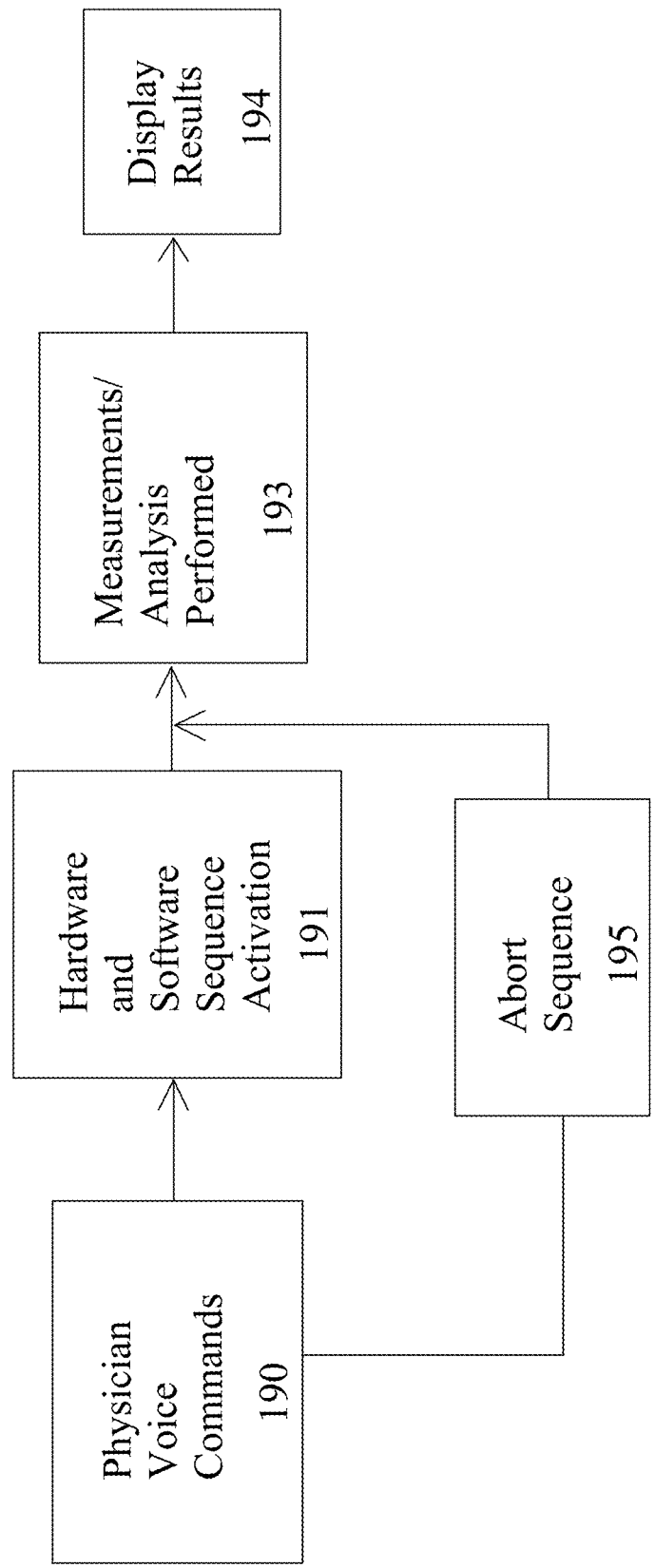
FIG. 13F is a block diagram of the general concept showing abort sequence block.

As shown in conjunction with FIG. 13D, once the physician determines that the ablation is complete (block 378), the algorithm in the program is activated (block 382) either with a mouse of via voice activation. Pacing is then commenced via the CS catheter (block 384). With the algorithm activated, the time between pacing spikes on the CS catheter and the ablation catheter is immediately displayed on the screen (block 388). Pacing may then be commenced from the ablation catheter (block 388), and the corresponding values are then displayed on the screen (block 392). If the line of block is complete (block 394), the procedure is completed.

In one aspect of the disclosure, the automated measurements can be activated and performed by physician's voice activated commands. The voice activated commands may be used for atrial flutter, or may be used for any other arrythmia's. For this embodiment, as shown in conjunction with FIG. 13E, the physician gives a set of predetermined voice commands 190, which activate a set of automatic measurements 192 which are then displayed 194 on the monitor, making the procedure proceed quickly and more efficiently.

Once the measurement sequence is activated, the sequence can be aborted either by voice commands or manually overriding on the computer via the mouse or keyboard. This is shown in conjunction with FIG. 13F, where physician voice commands 190 activate hardware and software sequence activation 191. The sequence can be aborted 195 at any time during the measurement phase. If the sequence is not aborted, the measurements are performed 193 and the results are displayed 194.

Figure 13G:
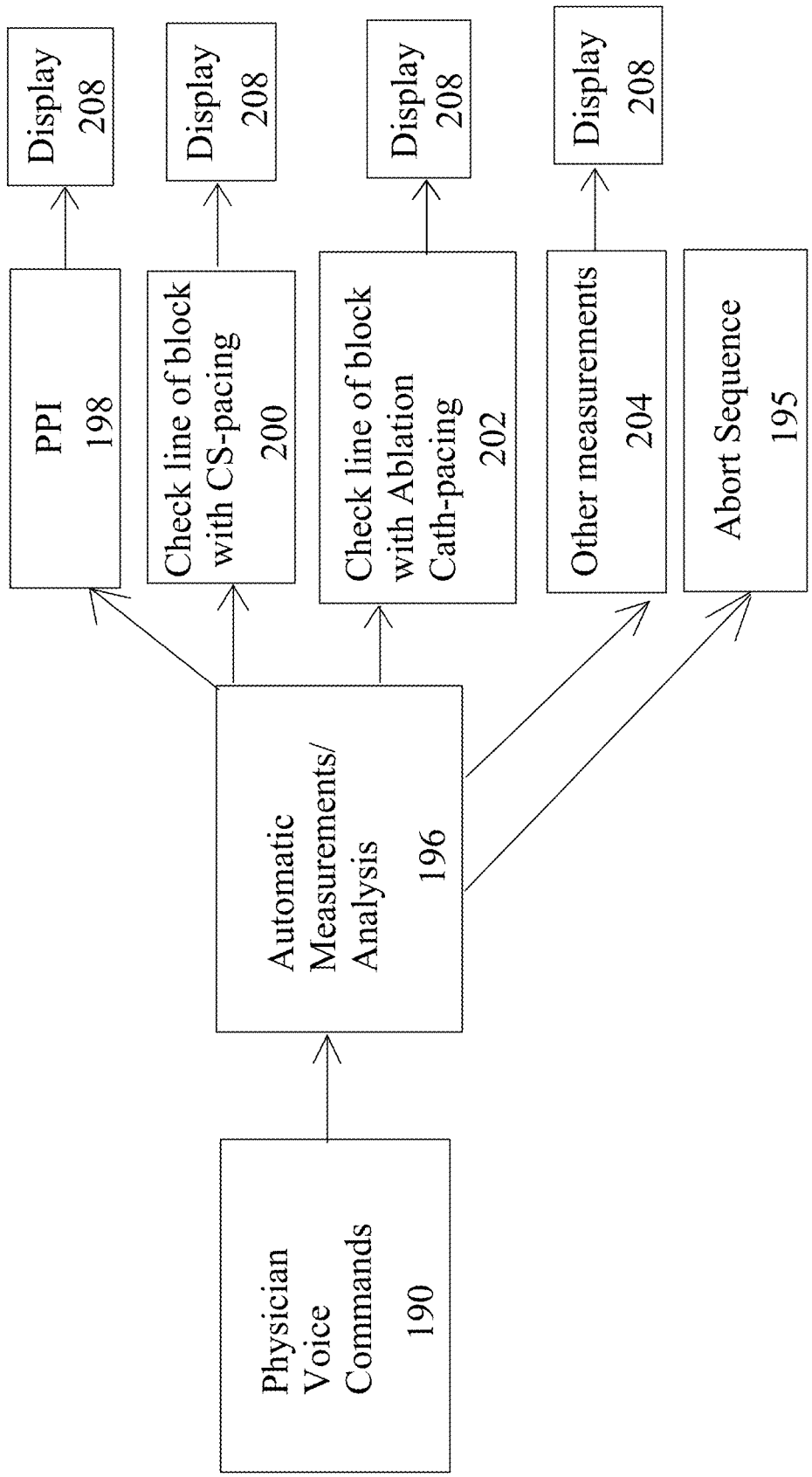
FIG. 13G is a block diagram of the general concept showing various measurements that can be activated or performed.

Shown in conjunction with FIG. 13G, the physician's voice commands 190 can be used for various different measurements 196, such as without limitation, measurement of post-pacing interval (PPI) 198, checking for line of block with CS-pacing 200, checking for line of block with pacing from the ablation catheter 202, and various other measurements 204. Once these measurements are performed, the results are displayed 208 on the monitor.

Figure 13H:
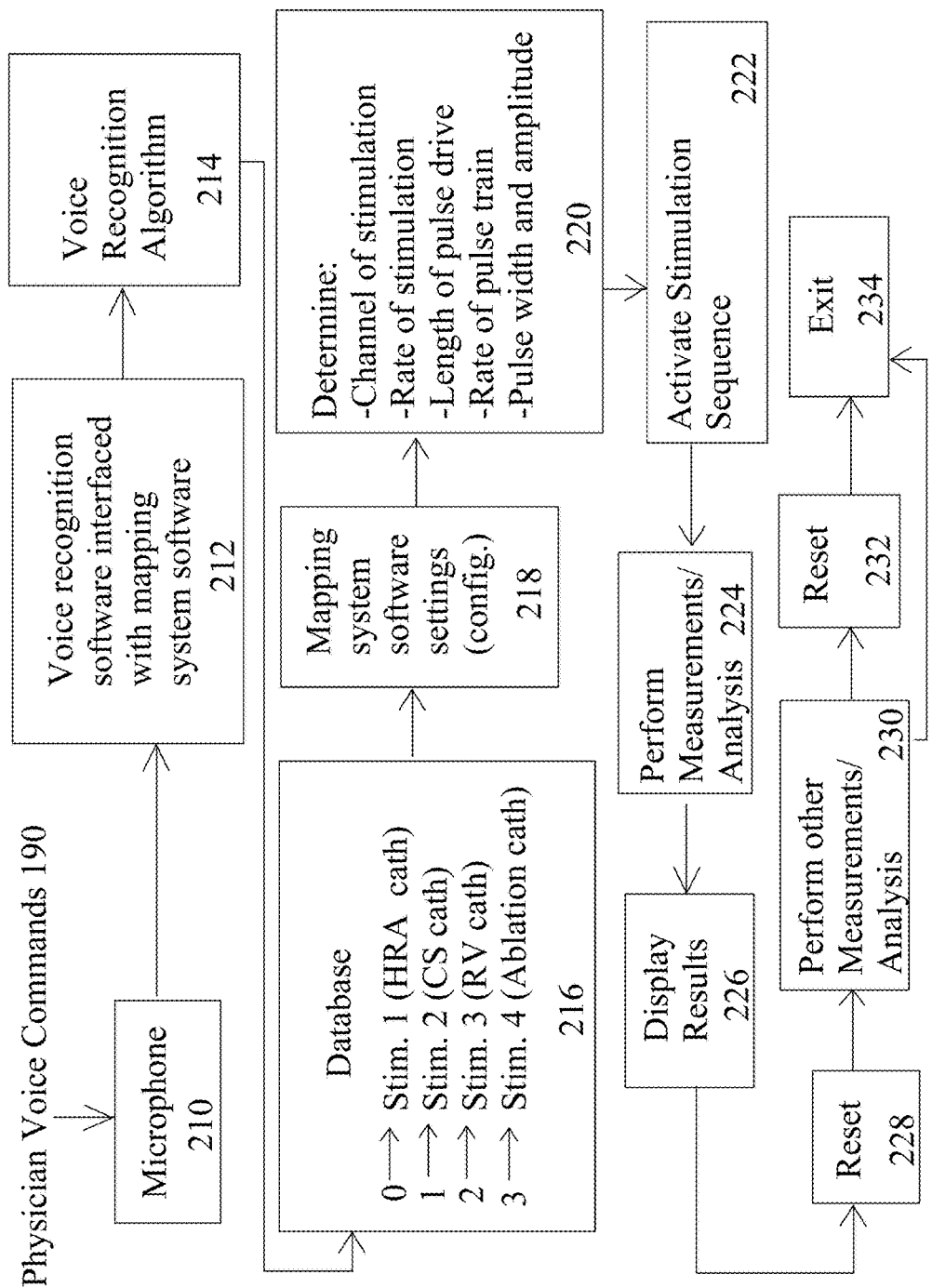
FIG. 13H is a more detailed block diagram of the concept of voice activated commands for automated measurements.

The sequence of events for this embodiment is generally shown in further detail in conjunction with FIG. 13H. The physician's voice commands 190 are spoken into a microphone 210 which is configured and connected to the computer 7. The voice recognition software 212 is the interface to the mapping system. The voice recognition software may be Microsoft Windows based software which may be interfaced to the Mapping system software, or may be any available voice recognition software that is available which is then interfaced with the Mapping system software. Some of the commonly available voice recognition software is Dragon Naturally Speaking, Speakeasy, Microsoft Office, these or any other speech recognition software may be used. Pre-determined voice commands, are coded and stored in a database 216 within the computer 7. Also, stored in the database 216 is the hardware configuration of the pacing stimulator 14 (shown in FIG. 3) which is connected to the computer and software 7 via a junction box 12, which was shown in conjunction with FIG. 3. The hardware configuration includes the different catheters connection information. Typically, the HRA catheter is connected to channel 1 of the stimulator, the CS catheter is connected to channel 2 of the stimulator, the RV catheter is connected to channel 3 of the stimulator, and the ablation catheter is connected to channel 4 of the stimulator. Other connection configurations may also be used. Whichever catheters are connected to the four channels of the stimulator, it is configured into the computer. This information is stored in the database 216 along with the other information.

The voice activation commands are coded. Depending on the voice activation commands, the information is decoded and along with the other information that is stored in the mapping system software configuration file. For example, if the command is "check PPI", the decoded information would calculate the tachycardia cycle length (TCL), pace from the ablation catheter (stimulation Channel 4 in this example) at a cycle which is a predetermined level faster than the tachycardia cycle length (TCL) to capture and drive the atrium faster. The decoded information would also contain the length of pulse drive, and pulse width and amplitude of the pulses. Once the proper sequence is activated, the pulse train is delivered as per the coded predetermined instructions. Once the pacing interval is established, the pacing is recognized by the computer software and stopped after a pre-determined number of pulses, and the first escape interval is measured and displayed on the monitor, as was previously described in conjunction with FIG. 10.

The software is also configured such that the stimulation sequence can be aborted any time with a coded voice command or a command via the keyboard or mouse. These measurements can also be repeated via coded commands multiple times.

Similarly, the measurement for checking for line of block is also automated, as was described in conjunction with FIG. 12 and FIG. 13. The same methodology is used as just described above with different predetermined code words. For example, with appropriate voice commands the checking for line of block with CS pacing is performed by the computer software, by stimulating the appropriate channel which is connected to the CS catheter (in this example stimulation channel 2). In this case, the decoded information contains the cycle length for pacing (typically around 500 msec), the electrode pair for pacing (typically a proximal pair), the number of cycles in the pulse train, and pulse width and output amplitude. As was described earlier, in conjunction with FIG. 12, the measurement that is performed is the time between the CS pacing spike and the signal from the ablation catheter which is placed lateral to the line of block for this measurement. This time is measured and displayed on the screen 208. The measurement can be repeated or the program can be reset.

Similarly, the automation of measurement for checking for line of block in the counterclockwise direction was previously described in conjunction with FIG. 13A. This measurement sequence can be similarly activated and measured and displayed. In this case, the pacing is performed from the distal tip of the ablation catheter, (channel 4 in this example), and the measurement is made from the pacing spike on the ablation catheter to the CS catheter. Again, the ablation catheter is positioned in the low lateral position just lateral to the ablation line.

AVNRT Ablation

The mapping system of this disclosure 160 also finds use in AVNRT (AV nodal reentry tachycardia) ablations. The methodology of AVNRT ablations has been described previously in U.S. patent application Ser. Nos. 11/112,648 and 11/146,601 now U.S. Pat. Nos. 7,578,816 and 7,588,567. The content of both of these disclosures is incorporated herein in its entirety. The application of the current mapping system of this disclosure 160 to AVNRT ablations is shown in conjunctions with FIGS. 14-16C.

Figure 14:
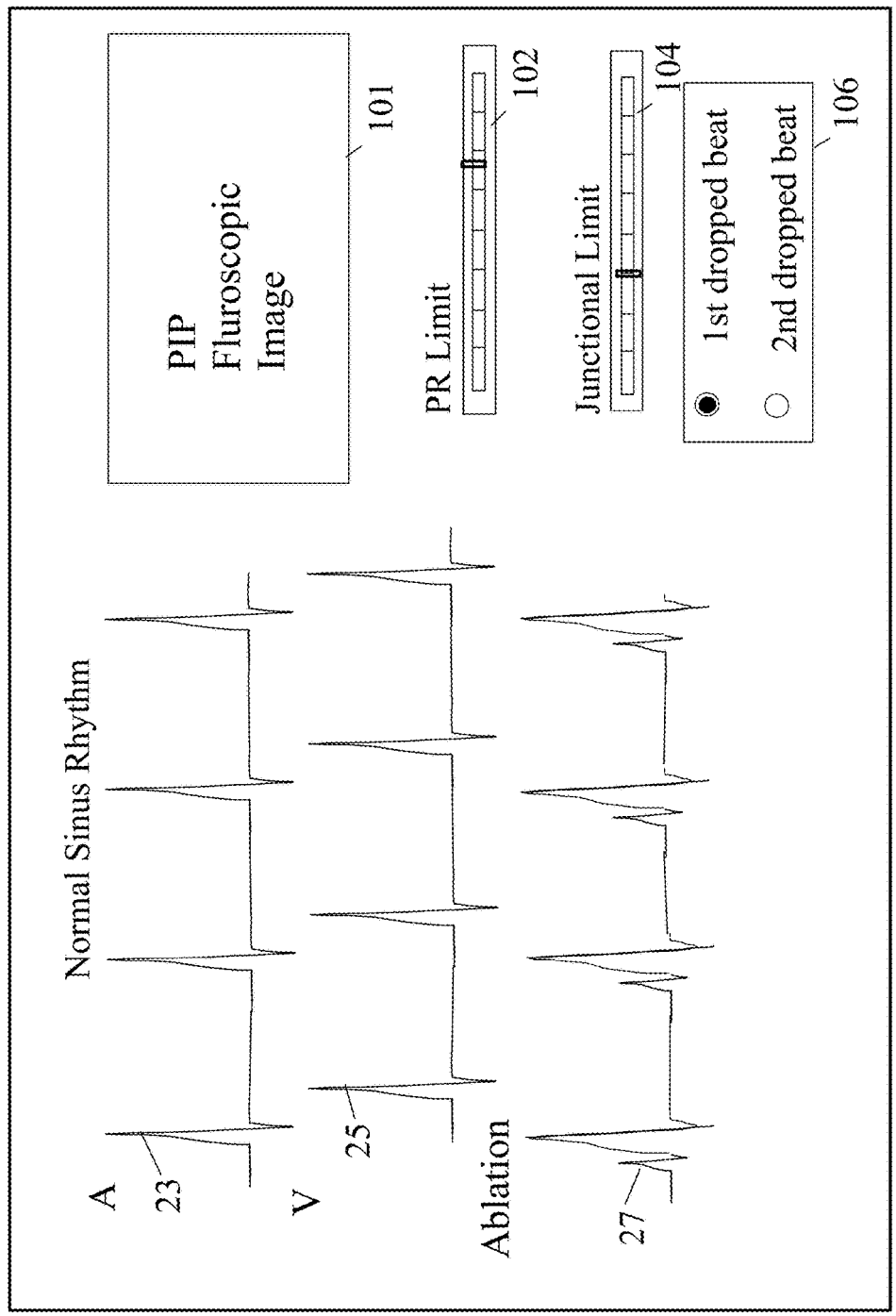
FIG. 14 shows schematically the screen for AVNRT ablation with features for automatically shutting-off ablation energy under pre-determined conditions.

As shown in conjunction with FIG. 14, the mapping system screen incorporates picture in picture (PIP) 101, where both the fluoroscopic image (in PIP 101) and intracardiac electrograms are incorporated into the same screen for convenience. This is very advantageous since during ablation the location of the catheter (from fluoroscopy) and the electrograms can be watched simultaneously. The fluoroscopic image 101 may be in any view. Some of the common views are right anterior oblique (RAO), left anterior oblique (LAO), or anterior-posterior (AP) view. The signals shown in conjunction with FIG. 14 are atrial 23, ventricular 25, and ablation catheter signals 27. Other signals, such as His Bundle recording and surface ECG recording are not shown but may be displayed as well.

Figure 15:
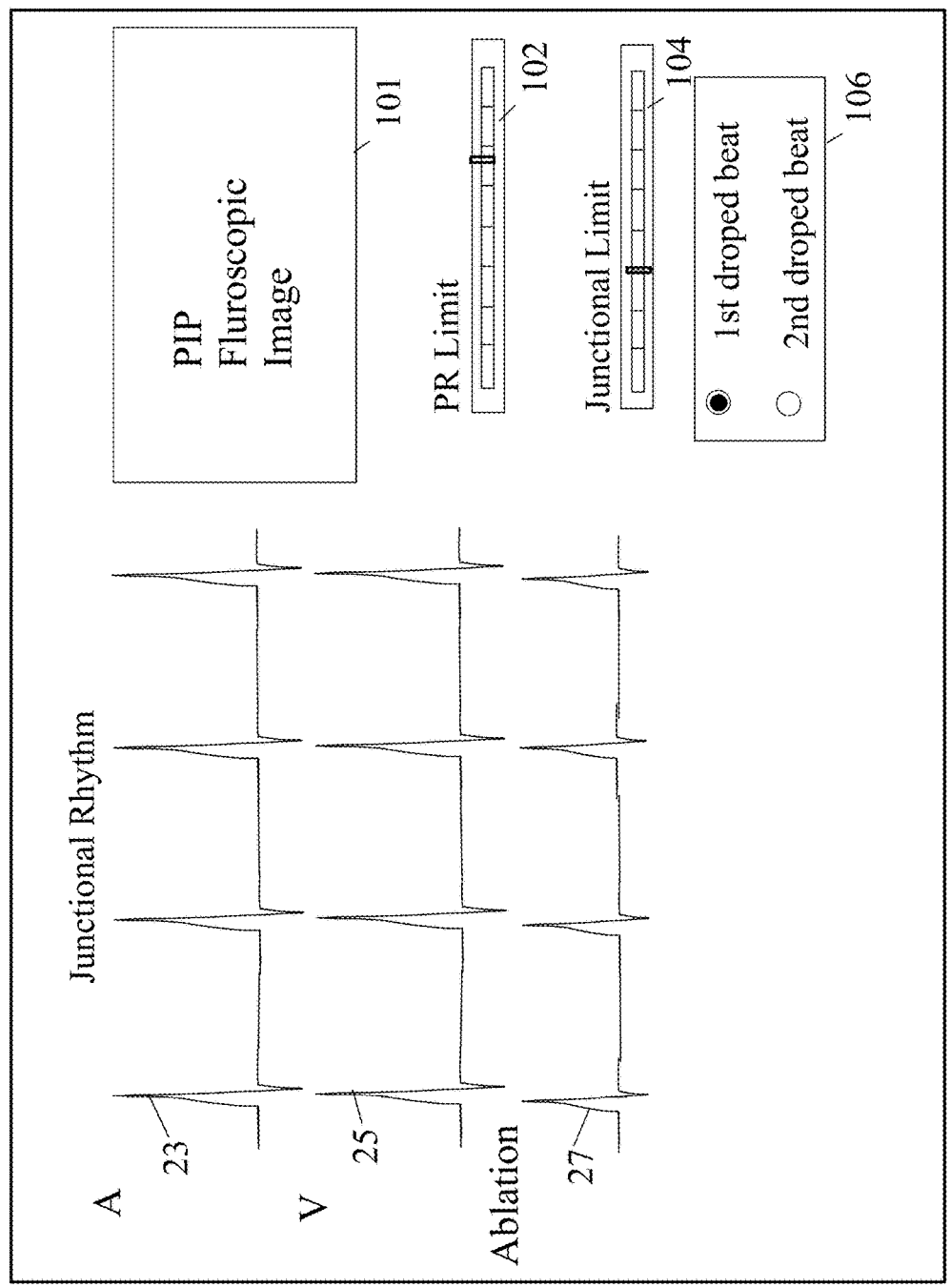
FIG. 15 shows schematically the screen for AVNRT ablation with junctional rhythm.
Figure 16A:
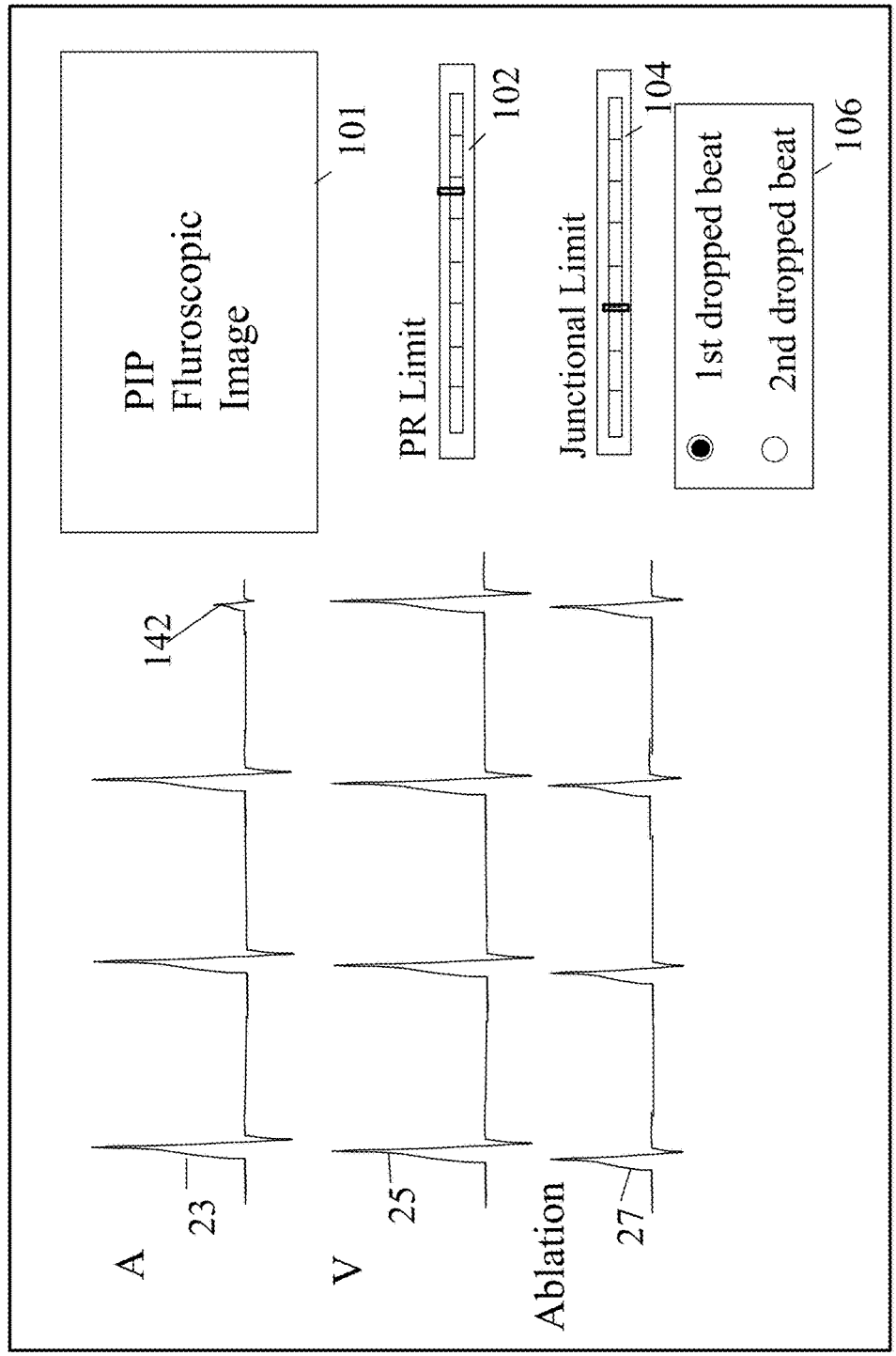
FIG. 16A shows schematically the screen for AVNRT ablation with junctional rhythm, and retrogradely blocked atrial beat.
Figure 16B:
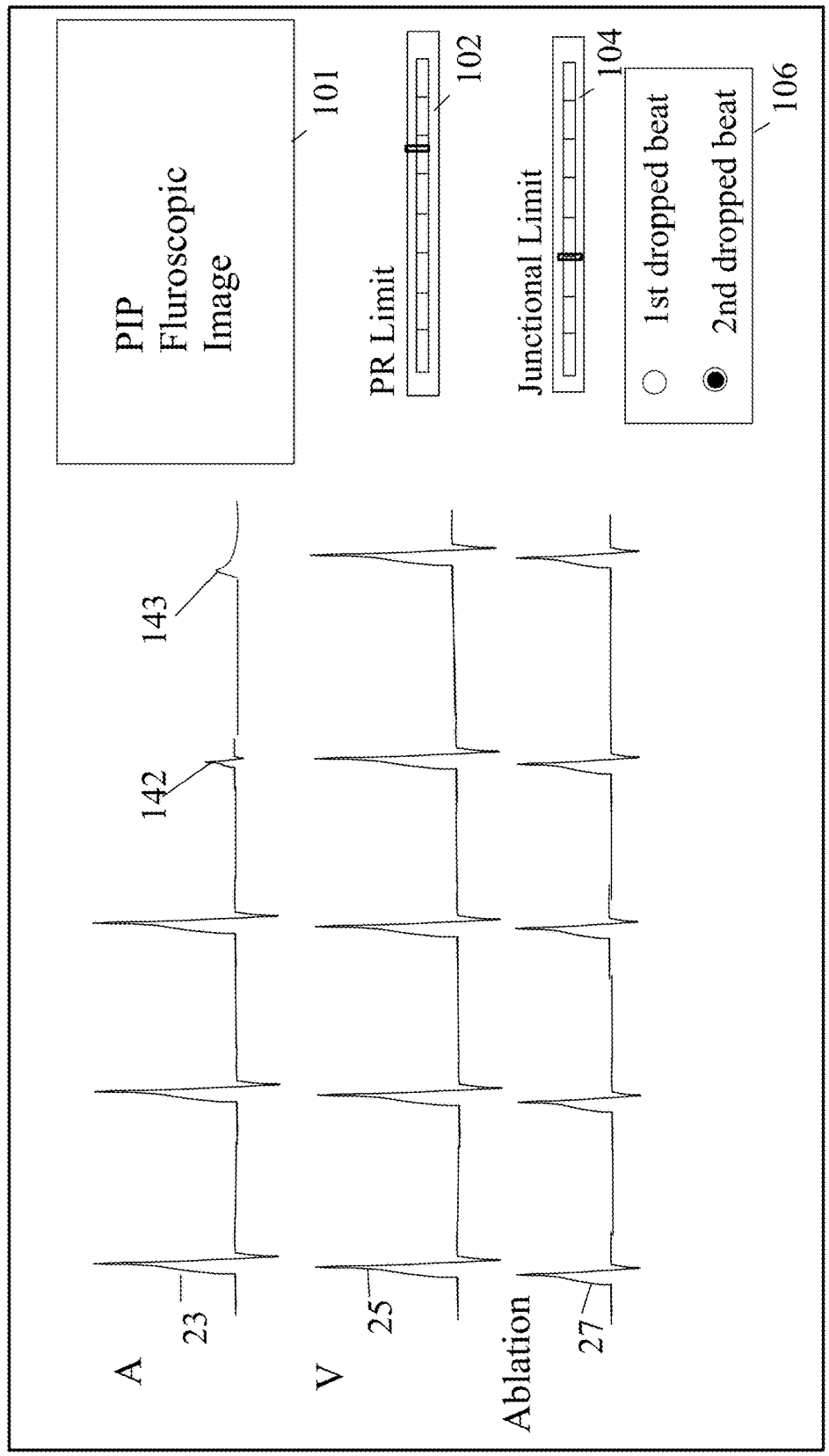
FIG. 16B shows schematically the screen for AVNRT ablation with junctional rhythm, and two retrogradely blocked atrial beats.
Figure 16C:
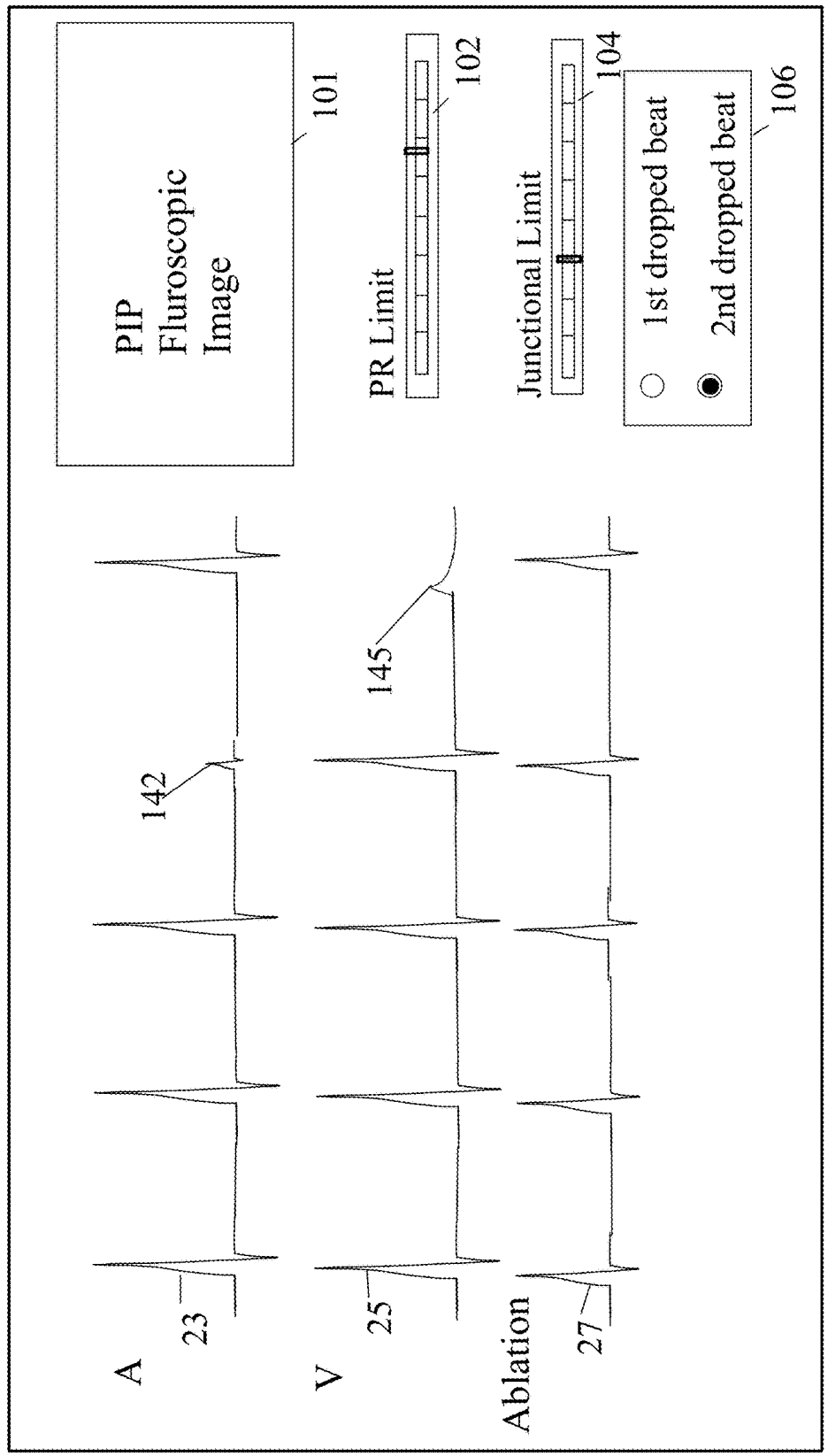
FIG. 16C shows schematically the screen for AVNRT ablation with junctional rhythm, and two blocked beats.

In this method and system, the AVNRT ablations may be automatically stopped (i.e. the delivery of ablation energy may be interrupted) based on pre-determined conditions. The limits of automatically stopping or interrupting can be entered on the screen with indications such as PR prolongation limit 102, and Junctional rate limit 104 and stopping at the first or second dropped beat 106. When the catheter is appropriately placed based on fluoroscopic guidance and the appropriate signal on the ABL channel 27, the ablation is begin. Generally, if the ablation energy is effective junctional rhythm or junctional acceleration is achieved, i.e. the atrial 23 and ventricular 25 signals appear nearly simultaneously in time or are aligned on the timing axis (x-axis). This is shown in FIG. 15 where the atrial 23 and ventricular 25 signals are nearly simultaneous. Shown in conjunction with FIG. 16A, in the method and system of this disclosure, based on a pre-determined event such as retrograde block 142 (where the atrial 23 signal is dropped), the ablation shuts off automatically as a safety mechanism. The software is also configured and programmed such that system may also be programmed to stop on the second dropped beat to avoid false positives in the event of PVC's or PAC's. This is shown in conjunction with FIGS. 16B and 16C. FIG. 16B shows the scenario where the system will stop at the second retrogradely blocked beat 143. FIG. 16C shows the scenario where the system will stop on the second dropped beat, which in this case antegradely dropped beat 145

Figure 17:
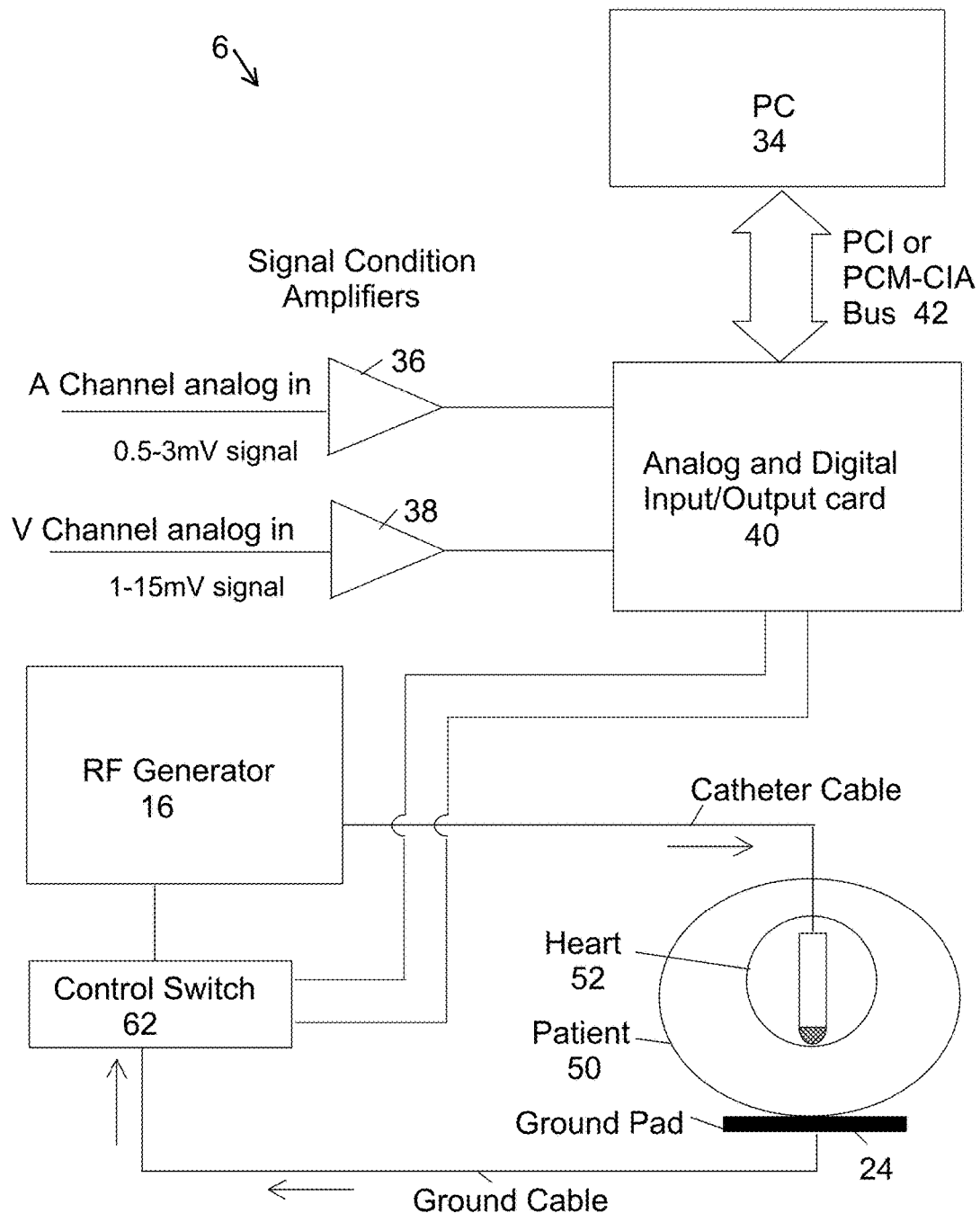
FIG. 17 depicts schematically the block diagram for RF generator 16 connected to the patient and a control switch 62 in the return path for automatically shutting energy delivery.

The system and methodology for achieving this is shown schematically in conjunction with FIG. 17 (from U.S. Pat. No. 7,578,816). As shown in FIG. 17, based on a pre-determined condition, such as retrograde block during junctional rhythm, the computer logic sends a control signal which activates a relay switch to interrupt the energy delivery (or shut the ablation off based on the programmed pre-determined conditions). Following that, the catheter is re-positioned and the ablation procedure is restarted.

In one embodiment, the energy delivery during AVNRT procedure can also be stopped using voice activation, based on the physician observing a pre-determined condition described above. In this embodiment, the command for example "stop ablation" is coded and configured to trip a switch in the ablation circuit, which stops the energy delivery to the patient. The details of voice controlled and voice activation are highlighted in the section on Atrial Flutter.

Among the other predetermined conditions are, antegrade block during junctional rhythm, junctional rate above a pre-determined level, and an increase in PR interval. Shown in conjunction with FIGS. 14 to 16C, the pre-determined PR interval 102 and maximum junctional rate 104 can also be programmed.

Application to Early Activation Timing

Another application of the Mapping system 160 of this disclosure is for ablating cardiac arrhythmias where early activation mapping is needed. Early activation mapping relative to a reference signal (where t=0) is essential for mapping many types of arrhythmias. Some examples, without limitation, are atrial tachycardia (AT), ventricular tachycardia (VT), right ventricular outflow tract tachycardia (RVOT), accessory pathway mediated tachycardia (AVRT), among others. In the method and system of this disclosure, early activation mapping with the mapping system 160 are shown in conjunction with FIGS. 18-21.

Figure 18:
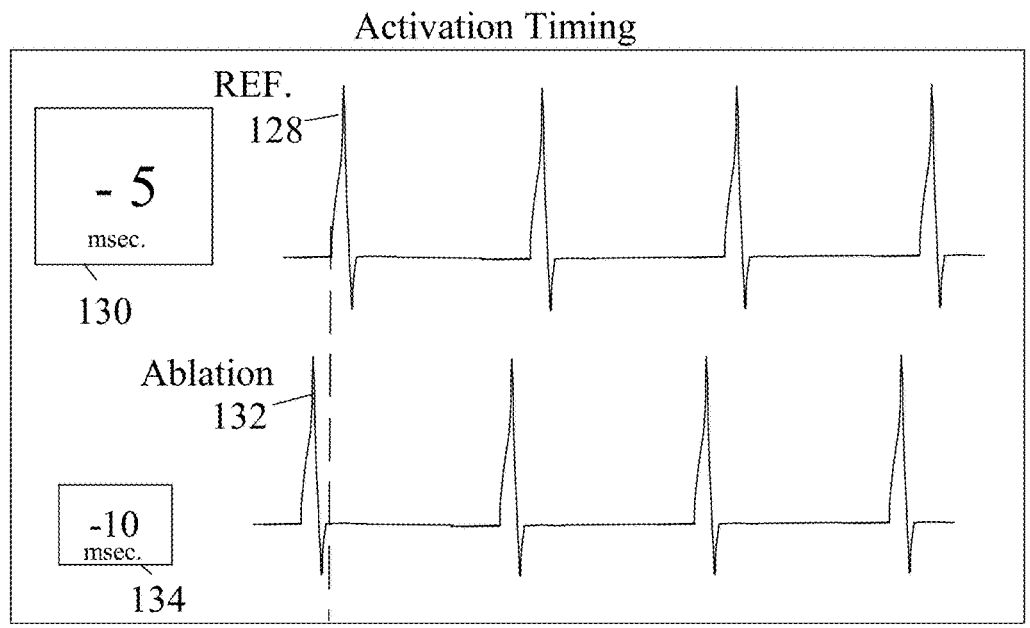
FIG. 18 shows schematically the screen for early activation timing, with an example where the ABL catheter precedes the reference catheter, and the timing is displayed as a negative number.

Shown in conjunction with FIG. 18 is one example of activation mapping using the current system and method. In one embodiment, as shown in the figure a reference signal is displayed (REF 128) on the screen. The reference signal is any signal that is used for comparison of timing, i.e. for the reference signal t=0. The timing of the ablation catheter signal (ABL 132) may be earlier than the REF signal 128, same as the REF 128, or later than the REF signal 128. In the method and system of this disclosure, the software (algorithm/program) is configured and programmed to continuously measure the time between the REF signal 128 and ABL signal 132, and display it in large and convenient way as to what the current timing of the ABL signal 132 is relative to the REF signal 128 in real-time or beat-to-beat basis. This is shown in FIG. 18 as block 130 where the time is displayed as −5 msec (relative to the reference signal) in this example. To make it more convenient for the ablating physician, the block 110 displaying the relative value is coded in color whenever the relative value is negative (generally the more negative the better). As one example, without limitation, whenever the ABL signal 132 is earlier than the REF signal 128 or same as the display box 110 turns green as an indication that the ablation target is generally close and the timing is relatively good.

The method and system of this disclosure, is a distinctly different concept than the existing mapping systems. In the existing mapping systems, as the physician manipulates the catheter, individual distinct points are taken at various different locations. Each one of those points contains relative location information and relative timing information. These points can be stored in a file in the computer. When enough points are collected, the whole file may be run in a review mode. Current methods and systems do not run or display the timing information continuously in real-time or near real-time, among other things, as is done in the method and system of this disclosure. Generally, difference here is running the timing in a review mode or running it continuously in real-time mode as in the method and system of the current disclosure.

As an another example, whenever the ABL signal 132 is after the REF signal 128, i.e. the value of relative number is positive, the display box 130 turns red indicating that the ablation site is not close. Alternatively, when the display box 130 value is negative, the color of the ABL signal 132 itself may turn green and when the display box 110 is positive, the color of the ABL signal 132 itself may turn red, or some other color indicating that the site in not good for ablating. It will be obvious to one skilled in the art, that the indication may be displayed in one of various ways, and any of ways indicating a relatively good or bad site is considered within the scope of this disclosure.

In this disclosure, unlike the existing systems the time between the REF signal 128 and ABL signal 132 is automatically displayed and updated continuously in real-time or near real-time. As for the flutter application, one of many different software available can be used for its implementation, and the use of any software is considered within the scope of this disclosure.

Another feature of the system of this disclosure, is that the software is configured and programmed such that there is another display box 134 shown in the bottom left of FIG. 18, which displays the "best" negative value that has been observed in the current session. This serves as a reference as to the best number so far that needs to be "beaten" to get to a better site. This can be "reset" at any time during the session. The number in this box becomes the number to beat, as the physician manipulates the catheter to achieve the "best" site to ablate. Reset means initializes and restarts the updating of the early activation time for that session.

Figure 19:
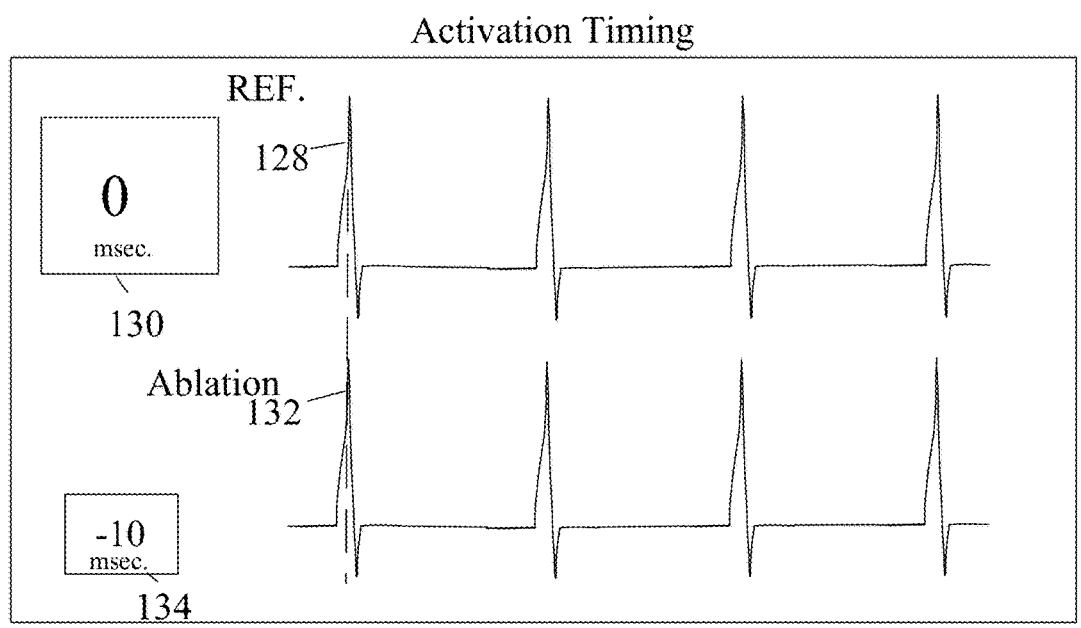
FIG. 19 shows schematically the screen for early activation timing, with an example where the ABL catheter is at the same time as REF catheter, giving a value of 0 msec in the display on the top left of the figure.
Figure 20:
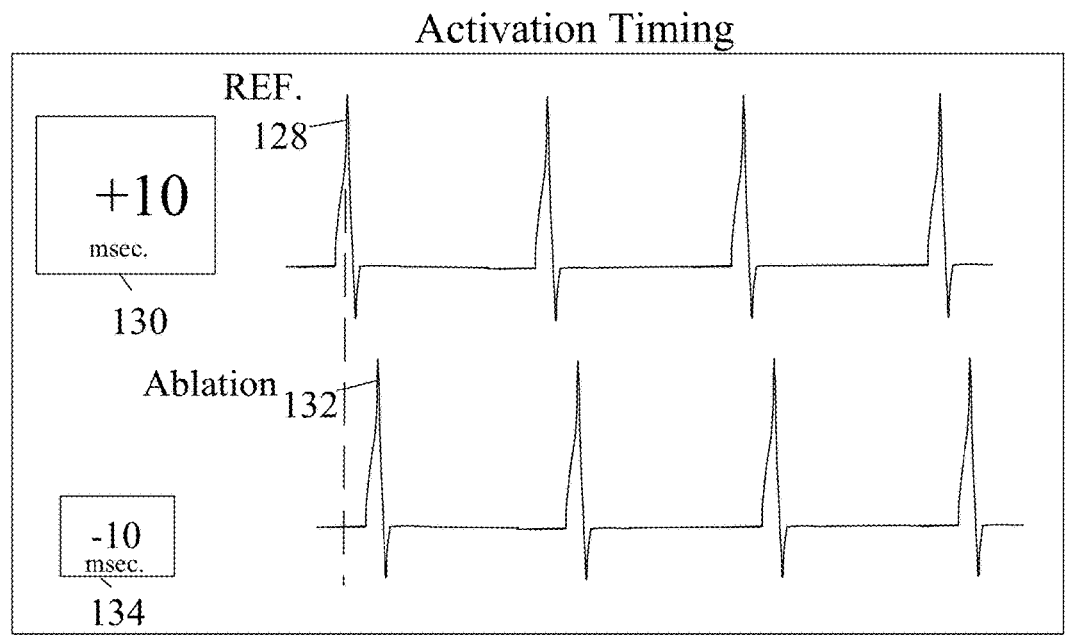
FIG. 20 shows schematically the screen for early activation timing, with an example where the ABL catheter is later in timing than the REF catheter, giving a value of positive number in the display on the top left of the figure.
Figure 21:
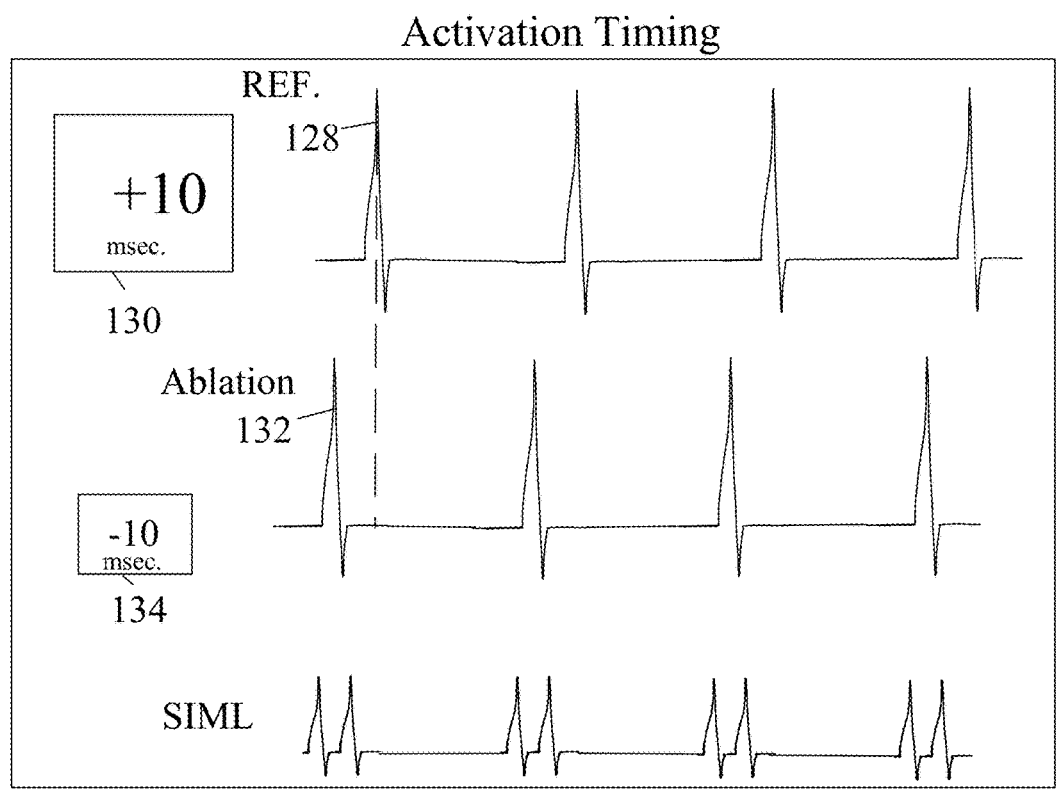
FIG. 21 shows schematically the screen for early activation timing, with an example where the ABL catheter precedes the reference catheter, and a third channel where the REF signal and the ABL are superimposed on each other.

FIG. 19 shows an example where the timing of the REF signal 106 is the same as ABL signal 132. In this example, without limitation, the display box turns green. Shown in FIG. 20 is an example where the ABL signal 132 is after the REF signal 128, i.e. the display number is a positive number. In this example, without limitation, the display box stays blank or turns red, indicating the undesirability of the site for ablation. The undesirablility of the site may be indicated by many other means, another example being the color of ablation signal turning red. In one embodiment, shown in conjunction with FIG. 21, a separate channel is displayed where the REF signal 128 and ABL signal 132 are superimposed. This will be helpful to physicians in determining the appropriate activation timing. The use of early activation timing may be for non-ischemic (normal heart) or ischemic heart cases.

Figure 22:
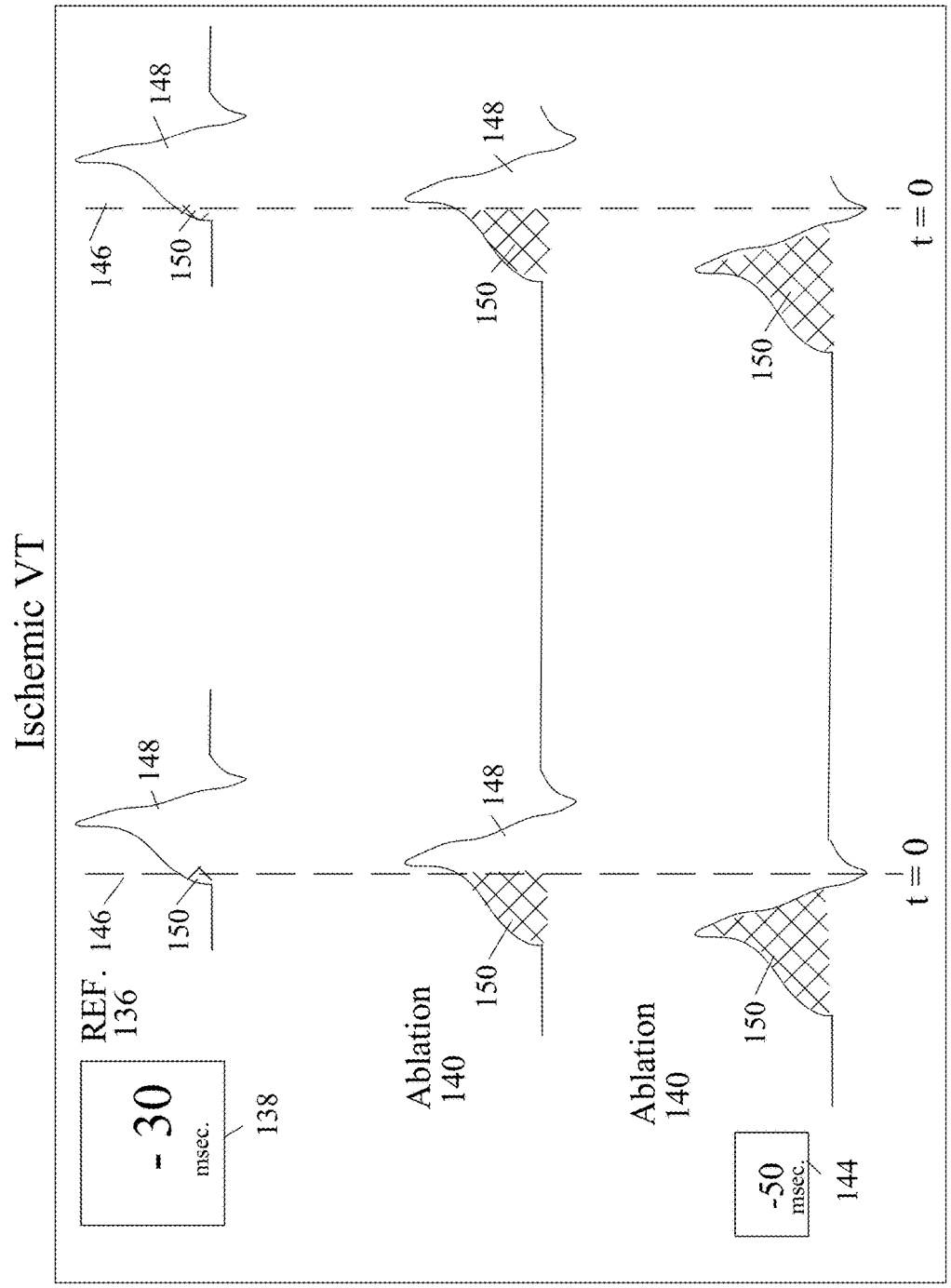
FIG. 22 shows schematically the screen for early activation timing for ischemic VT where the complex is wider and the part of the complex which precedes the reference is shaded with a different color.

In one embodiment, particularly useful for ischemic VT cases is shown in conjunction with FIG. 22. It is known in the art, that in ischemic VT cases the signals can be very wide. In this embodiment, a line 146 is drawn from the fiducial point (where t=0) of the REF signal 136 which extends to the ABL signal 140. In this embodiment, the part of the ABL signals 140 that is before the line depicted as 150 is color coded to visually show the early activation part. As the catheter is manipulated, and an earlier position is obtained, more part of the total signal 148 will be color coded to the earlier activation position, which is shown in the bottom tracing 150 in FIG. 22.

Advantageously, in this methodology the physician can see the full signal to appreciate any potentials (early potential, mid diastolic potential etc), as well as, see how the timing of the ABL signal 140 relative to the REF signal 136. The color coding scheme may be any scheme that may be used. As one example, without limitation, the part of the ABL signal 140 that precedes the fiducial line 146 may be color coded green, to show the desirability for ablation. Similarly any number of other color coding schemes may be used and are considered within the scope of this disclosure. Also, as shown in FIG. 22 the activation timing block 138 is also displayed as an additional aid to the ablating physician.

Template Matching for Tachycardia

Figure 23:
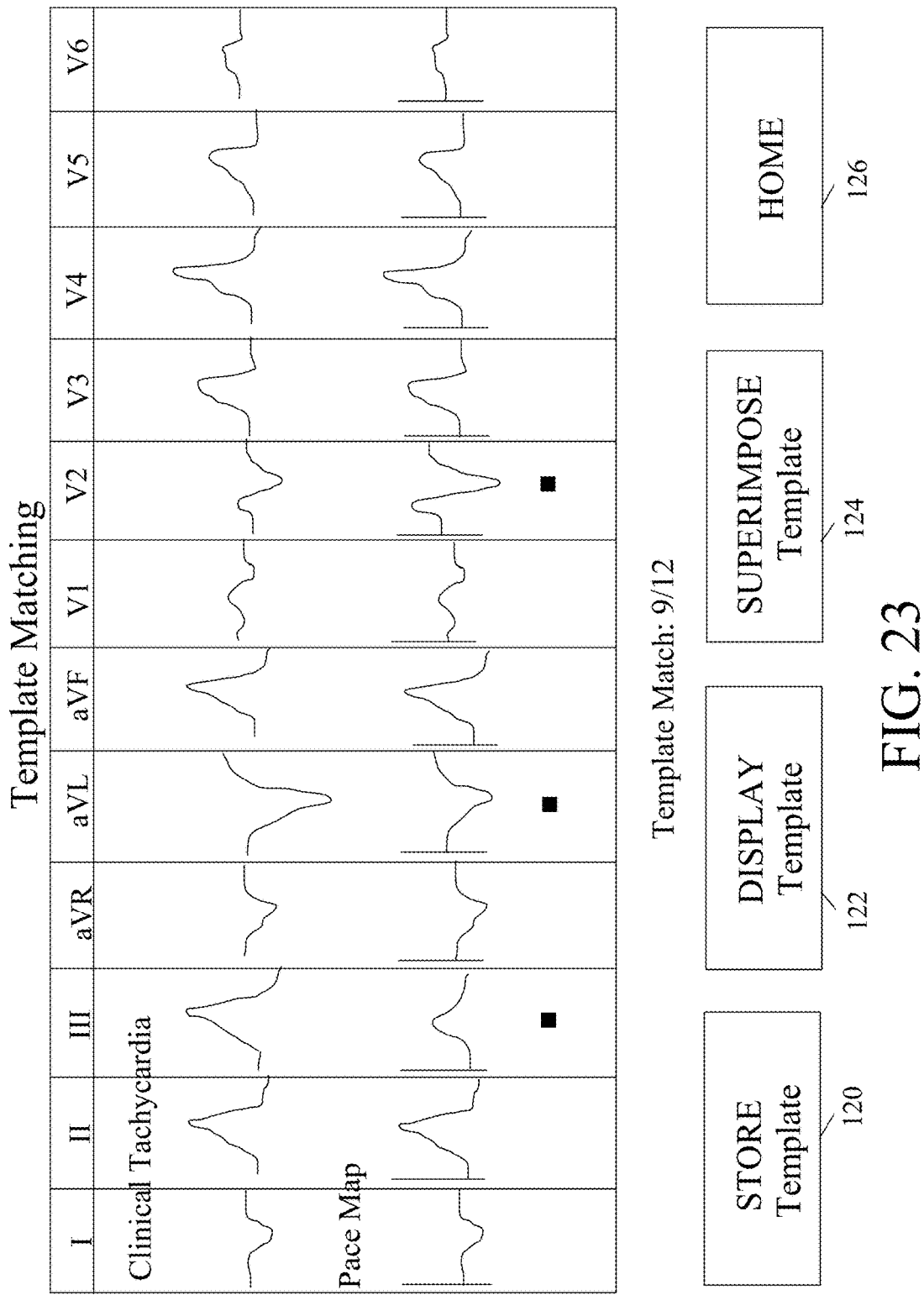
FIG. 23 shows schematically the screen for template matching for 12 leads (I, II, III, aVR, aVL, aVF, V1, V2, V3, V4, V5, and V6) and for pace mapping, where the corresponding signals are displayed adjacent to each other.

In this aspect of the disclosure, the screen for template matching is shown in conjunction with FIGS. 23 and 24. In FIG. 23 template matching is shown where the clinical tachycardia morphology 180 and pace map morphologies 185 are shown adjacent to each other. In this aspect of the disclosure, 12 channels of surface lead information (i.e. leads I, II, III, aVR, aVL, aVF, V1, V2, V3, V4, V5, V6) is brought into the program with 12 inputs into the data acquisition's A/D converter (FIG. 7). The software in the computer is configured/programmed such that by inducing the tachycardia, a store template 120 button on the screen stores the 12 surface channels of template for later comparison. The goal of template matching is to aid the physician to the ablation site, and increase the efficacy of the ablation procedure.

When pace mapping is performed in normal sinus rhythm, as shown in conjunction with FIG. 23, the original template of the clinical tachycardia 180 and pace map morphologies 185 are displayed adjacent to each other. This gives the ablating physician a quick look at the match between the template and the pace map morphology from the site where the catheter is located at the time. This procedure can be repeated as many times as needed to get a pace map that is almost identical to the clinical tachycardia. In the example in FIG. 23, signals from three leads shown as numbers 170, 171, and 172 are not matching.

Further, as shown in conjunction with FIG. 24, by pressing the superimpose template button 124 the clinical tachycardia template 180 and the pace map template 185 are superimposed on each other. In one embodiment, a table displaying the match of each of the 12 leads is shown below, with percent match for each of the 12 leads. Therefore, by utilizing the correlation function built into the software program, a 8/12 match (as an example) is displayed on the screen. A closer look reveals that channels marked with numbers 173, 174, 175 and 176 are not a match. Again, this may be repeated as many times as needed to get an appropriate match for the optimal ablation site. Advantageously, by configuring and programming the software which automats this procedure, the ablation procedure can proceed in an efficient and efficacious manner.

ECG Localization

In one aspect of the disclosure, initial localization or regionalization for the location site or exit site of the arrhythmia is performed utilizing the surface leads. This is typically done with a 12-lead EKG which are brought into the mapping system via A/D converter 111 as was shown in FIGS. 7A and 7B previously. In some cases, additional leads to the standard 12-leads may be used, i.e. 12-20 lead systems may also be used.

Initial 12-lead localization or regionalization is very useful for many different types of arrhythmias, including but not limited to Atrial tachycardia (AT), antegradely conducting accessory pathway such as Wolf-Parkinson-White syndrome (WPW), Ischemic VT, Idiopathic VT (RVOT or LVOT), and PVC mapping, among others.

The 12-lead localization of the current disclosure can also be used as a training and teaching tool for EP training.

In this disclosure, even though this embodiment is described in detail for AT and ischemic VT, it will be understood that it is applicable for all arrhythmias where surface leads can be used for localization.

It will be clear to one skilled in the art that the EKG localization based on the 12-lead can be interactive or may be done automatically by the computer program. In the embodiment where the 12-lead localization is performed automatically, the computer software is programmed and configured such that it evaluates morphology in each lead whether the P-wave or QRS complex is positive, negative or isoelectric. Based on the said morphology information and other information such as, including but not limited to, area under the curve, width of the QRS complex, and amplitude of the signal, the program algorithms makes determination based on the flow-chart logic as described below for the interactive portion of the program.

Figure 25:
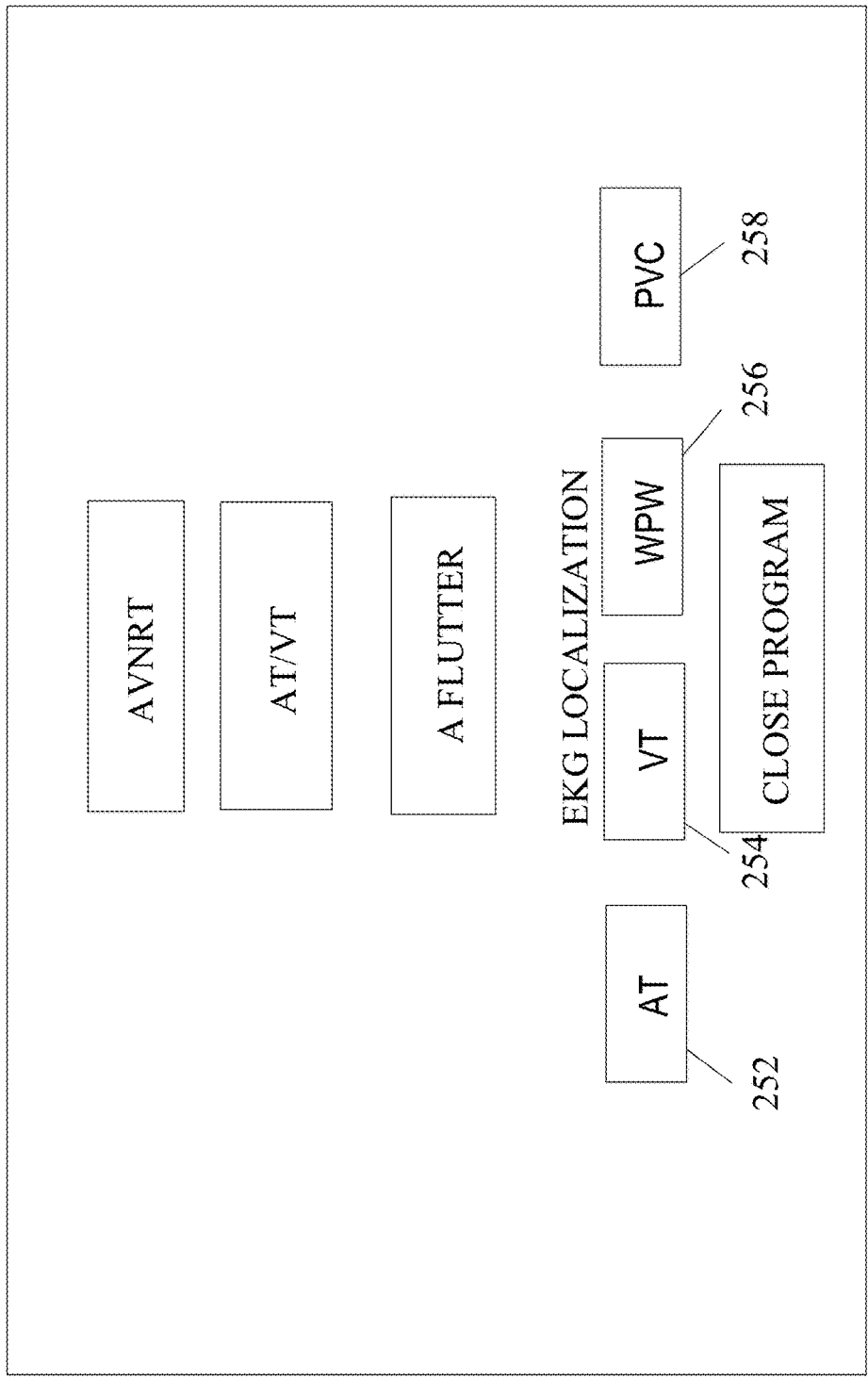
FIG. 25 shows one of the main menu screen of the program for ECG localization.

One implementation of the physician interactive program is shown in conjunction with FIG. 25, which shows the opening screen of this embodiment. In this screen under the EKG Localization portion the options shown are AT 252, VT 254, WPW 256, PVC 258, other programs not shown in this figure may also be included there.

Figure 26:
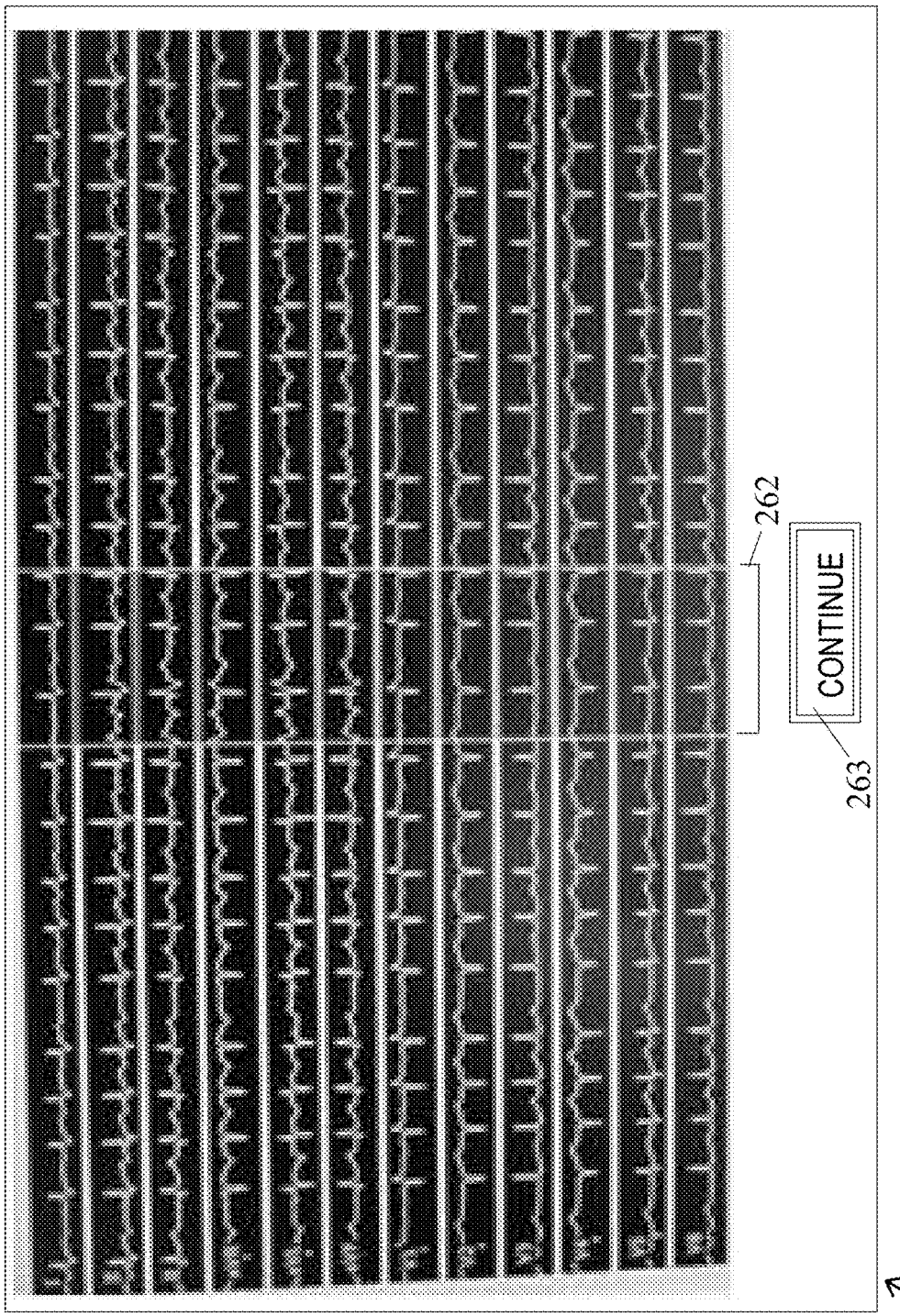
FIG. 26 shows the segment selection screen for the AT localization program.
Figure 27:
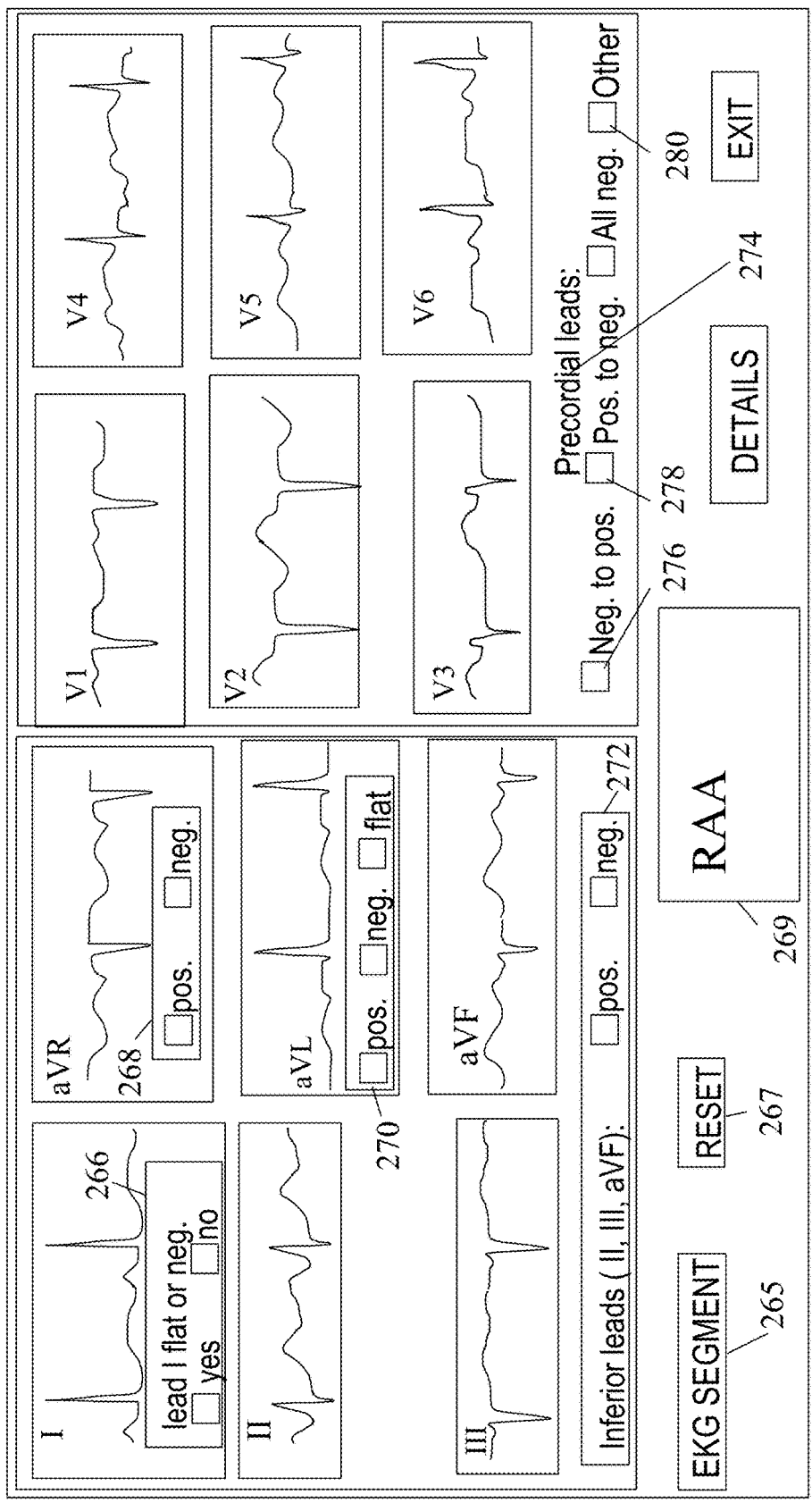
FIG. 27 shows the question answering screen for the AT localization program.

In one configuration, upon clicking AT 252, the screen shown in FIG. 26 is displayed. In one embodiment, the rationale for this screen is to select an appropriate or good segment which can be analyzed in detail. In the case of P-wave analyses, sometimes maneuvers may be performed to get unadulterated P-waves. These maneuvers may include drug infusion for AV dissociation or pacing to dissociate P-waves and R-waves. After an appropriate segment 62 is selected, by clicking on the continue button 263 the program proceeds to the analyses mode which is shown in conjunction with FIG. 27 in this disclosure. In the analyses screen, the segment 262 that was selected is displayed in a 12-lead format along with questions that the physician or operator needs to answer. In one example of this embodiment the question just below lead I is whether the P-wave is Flat or Negative 266. Advantageously, the question corresponding to each lead is displayed next to the morphology of the P-wave for that lead. After answering the question on Lead I, the physician or operator answers the questions on lead aVR 268, Inferior leads (II, III, aVF) 272 and Precordial leads 274 which include leads V1, V2, V3, V4, V5, and V6. When all the questions are answered by clicking the appropriate check boxes, the answer pops in a window which in this figure is shown in the bottom middle 269 of FIG. 27.

At any time during the process of filling out the screen, if the operator or physician feels that a different segment would be useful, they simply press the EKG Segment button 265 and the program takes them back to segment selection screen which was shown previously in FIG. 26. After re-selecting a different segment and pressing Continue 263 the program goes back to the screen shown in FIG. 27 for answering question. While the questions are being answered, a Back button (not shown) or a Reset button 267 allows the user to change or re-enter the answers.

Figure 28:
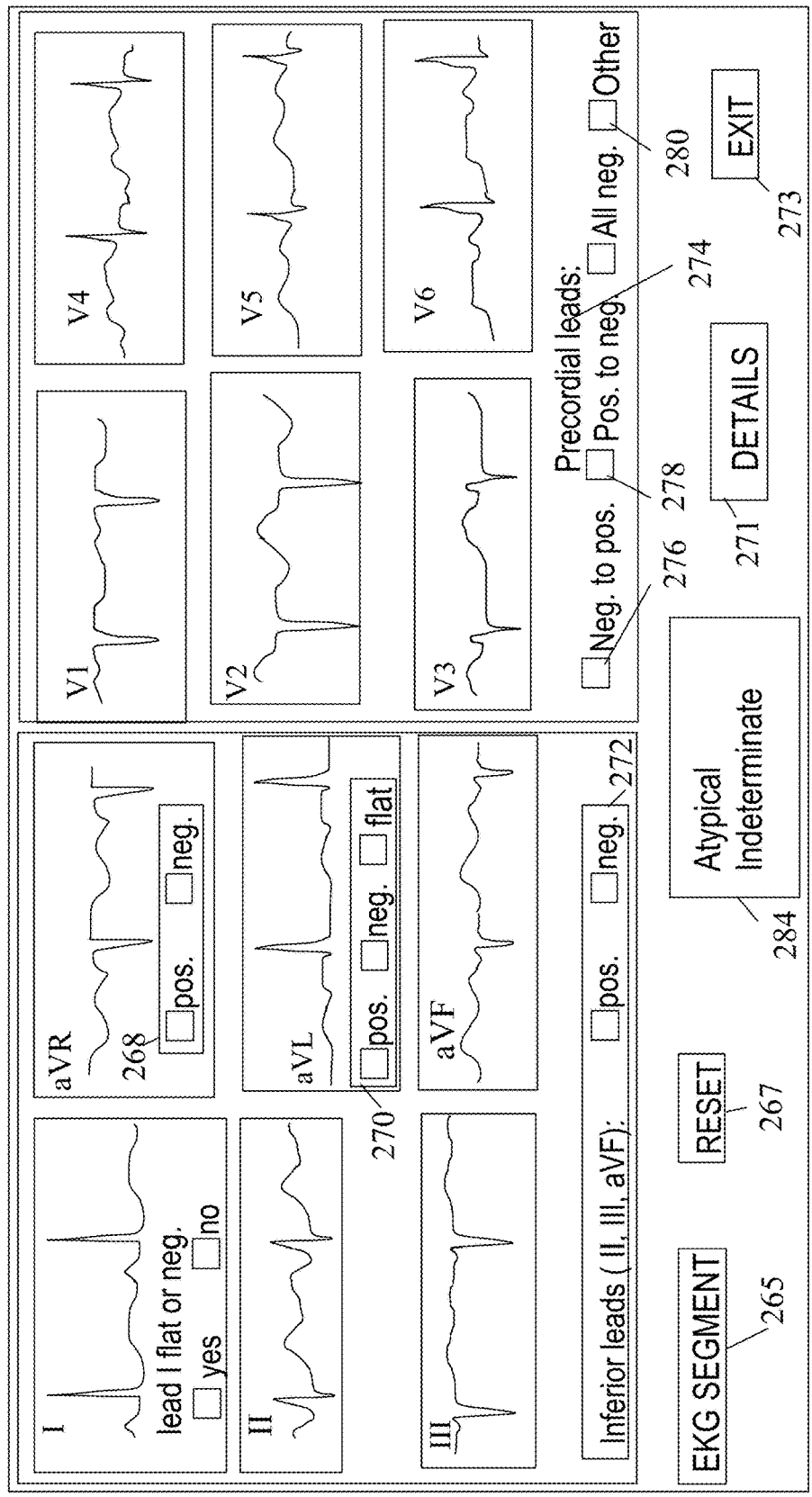
FIG. 28 shows the question answering screen for the AT localization program where the answer is "Atypical/Indeterminate".

As previously mentioned, when all the check boxes are completed, the answer appears on the screen. As shown in conjunction with FIG. 28, sometimes the answer is simply Indeterminate or Atypical 284. Further, by pressing the Details button 171 as shown in the figure, a detailed explanation appears on the screen. When the EKG localization is complete the Exit button 273 takes the user out of the program and into the main menu.

Figure 29:
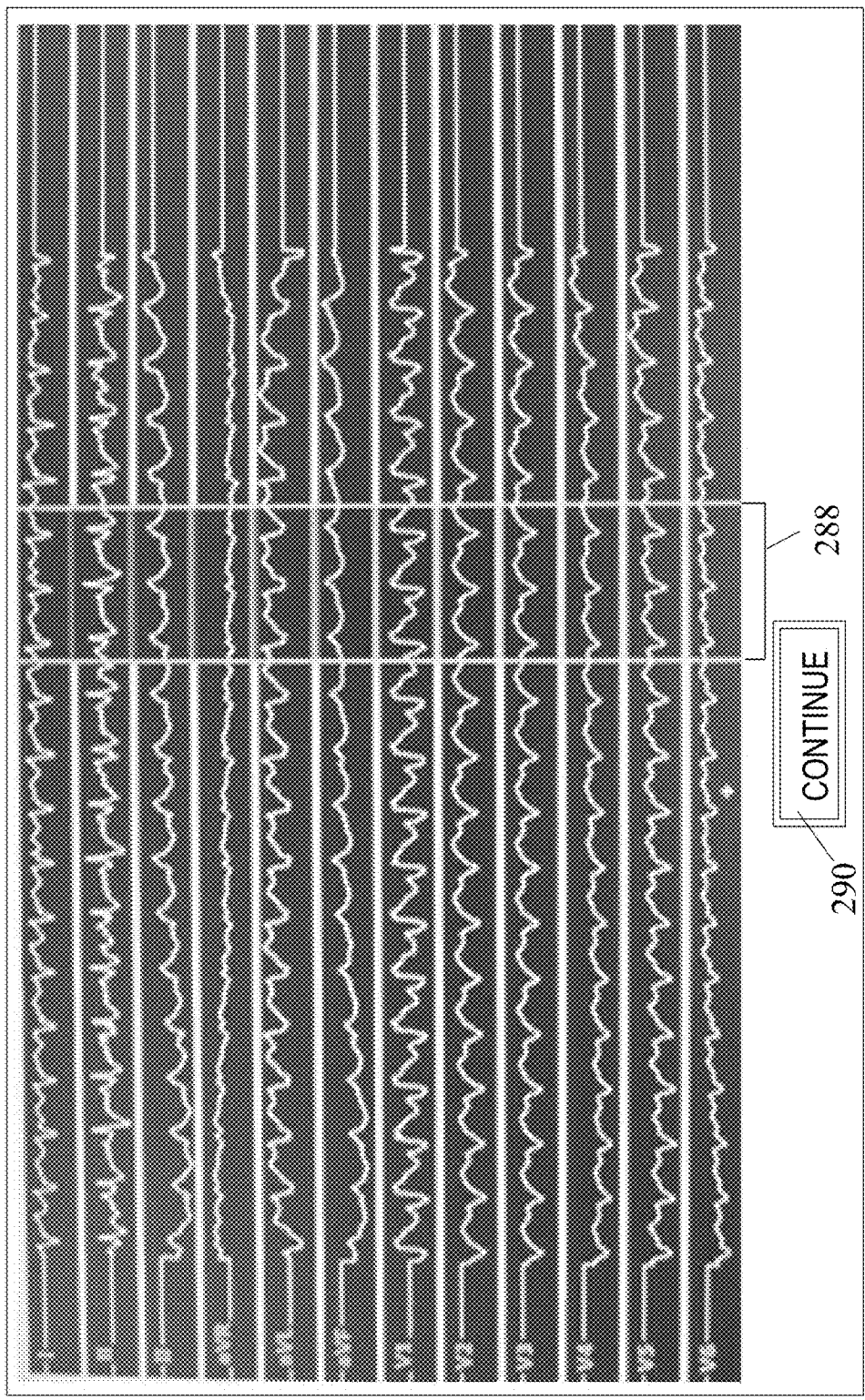
FIG. 29 shows the segment selection screen for the Ischemic VT localization part of the program.

In a similar methodology to the above AT program, when the VT button 254 which is shown in FIG. 25 is selected, the segment selection 288 for the VT program appears, which is shown in conjunction with FIG. 29. Once the proper screen is selected, and Continue button 290 is clicked, the next part of the program is displayed as is shown in conjunction with FIG. 30. In a similar fashion to the above described AT program, the 12-leads of the selected QRS segments are displayed on the screen. The physician or operator answers the questions regarding the location of the scar and the morphology of the QRS complex and the answer appears on the screen.

Figure 30:
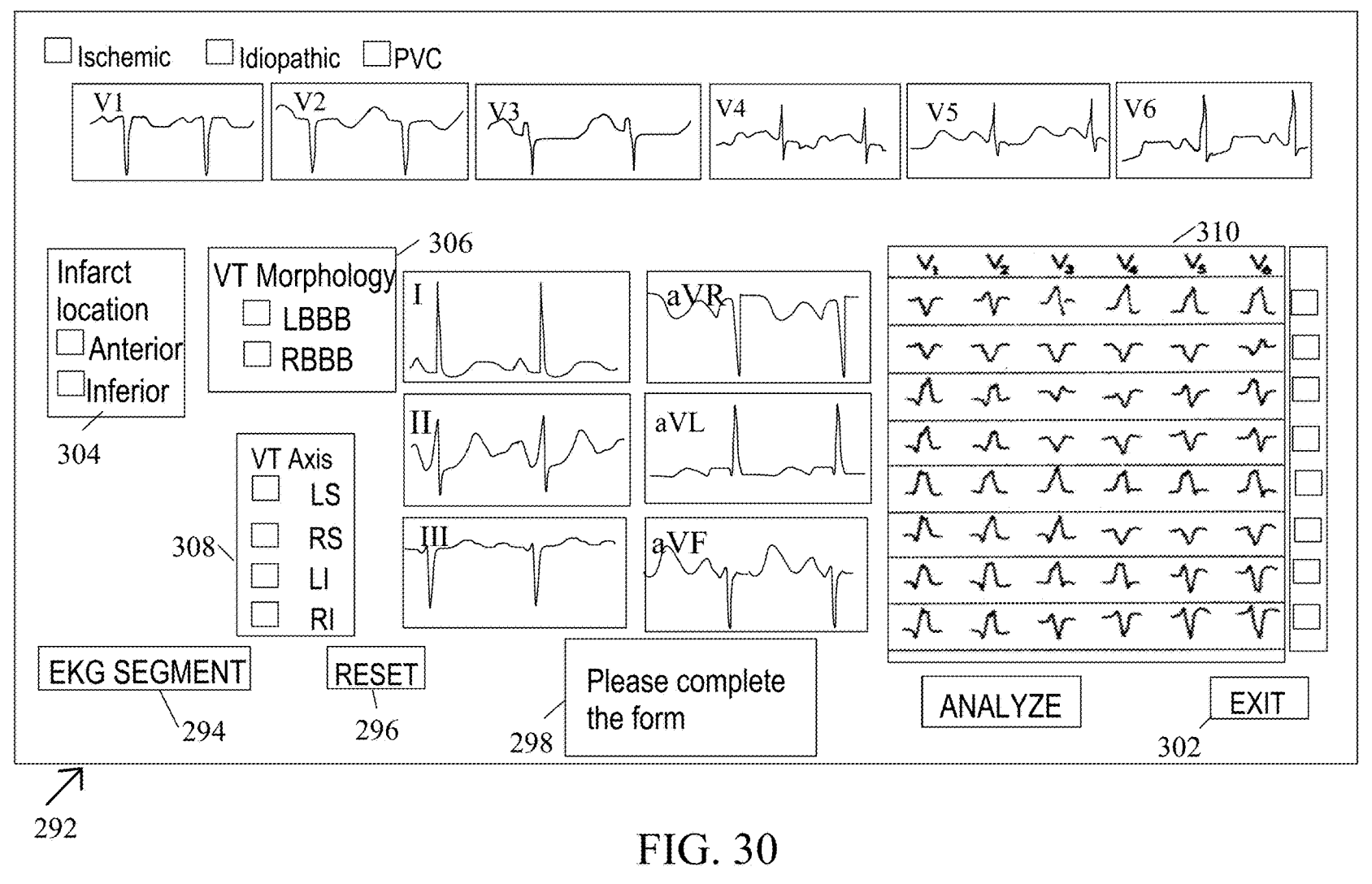
Figure 31:
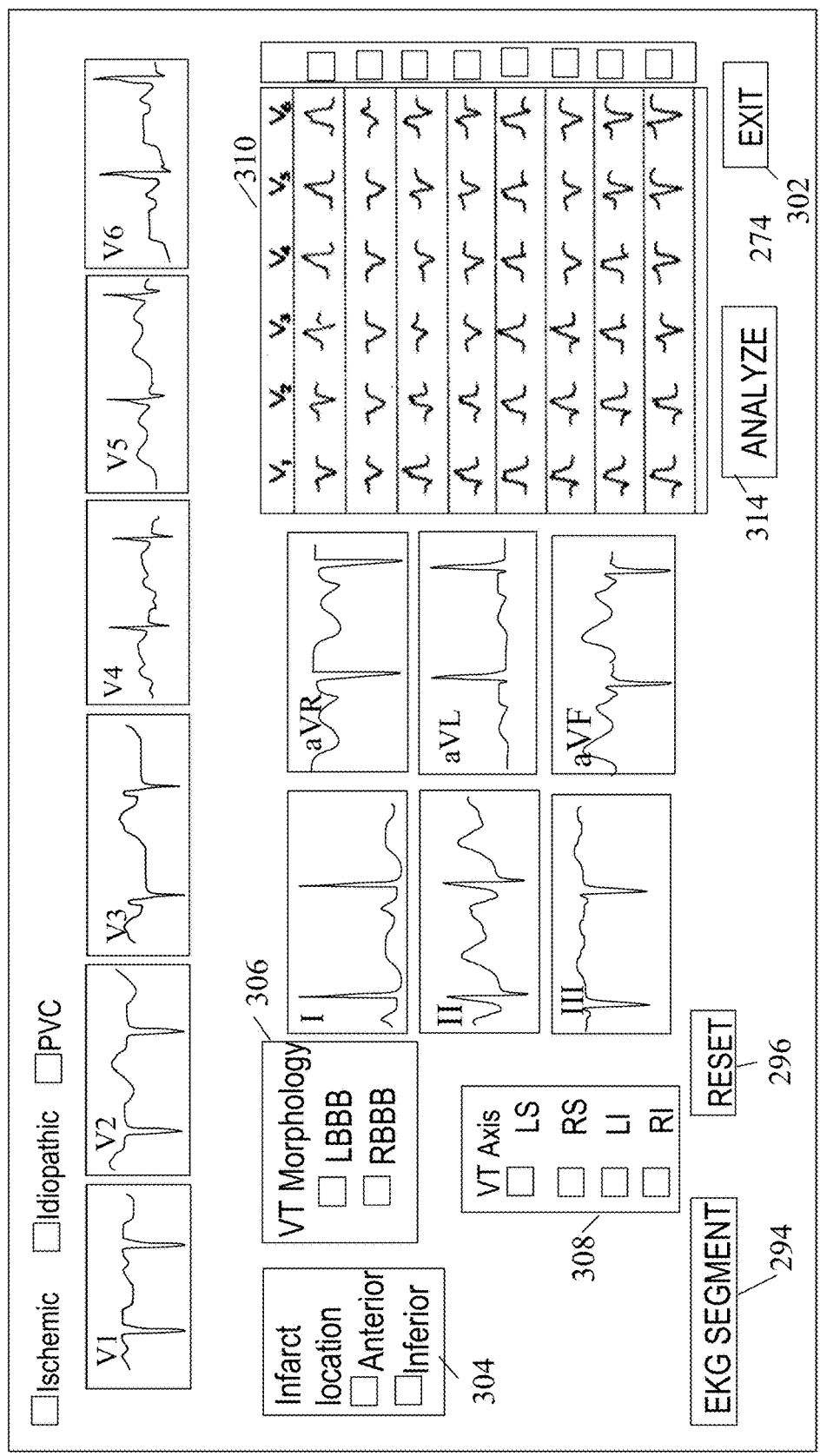
FIG. 31 shows the question answering screen of the Ischemic VT localization program, where the questions have been answered and the program is ready for analyses.
Figure 32:
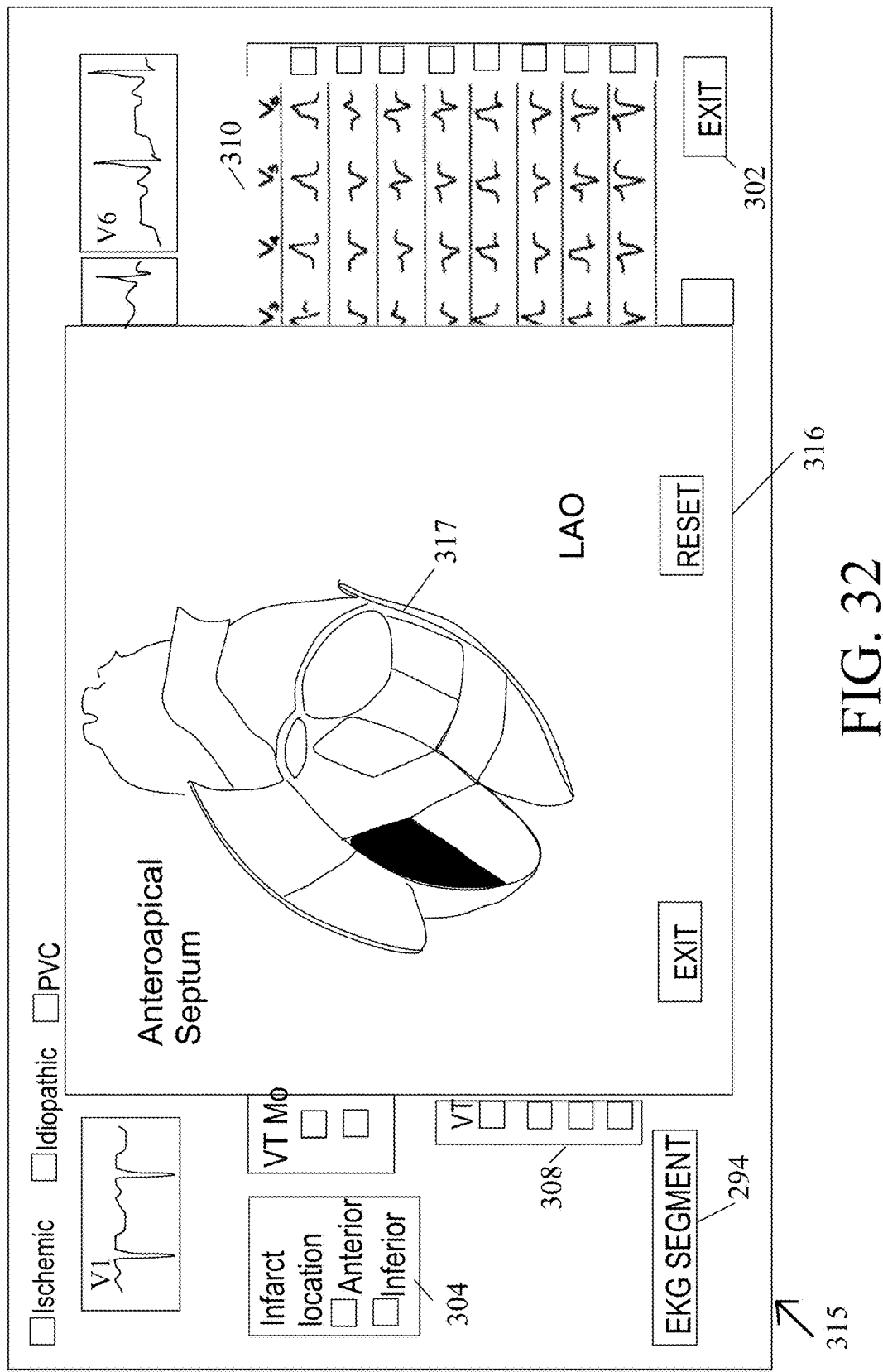
FIG. 32 shows the question answering screen of the Ischemic VT localization program, where the answer is displayed in graphical form.

As shown in FIG. 30, in one embodiment shown here as an example the physician or operator answers questions about whether the infarct is located Anterior or Inferior 304. There are other questions, such as whether the VT morphology has LBBB or RBBB 306 pattern. There is a box for VT Axis 308 whether it is LS, RS, LI, or RI. Further, in one embodiment a template may also be provided to match the most closest pattern for Precordial leads (V1, V2, V3, V4, V5, and V6). When all the boxes are appropriately checked, the Please Complete the Form 298 gets hidden, as is shown in FIG. 31. By clicking on the Analyze box 314 (FIG. 31), a picture of the heart 317 with shaded area of where the localization or regionalization is in the ventricle is displayed. This is shown in conjunction with FIG. 32. It will be clear to one skilled in the art that the results can be displayed in text form, in a 2D or 3D picture, or a 3D heart model, or on the patient's fluoroscopic image.

In one example, the physician or operator has the option to Reset and start over or to Exit from the program. As was the case in the AT version of the program, some combination of answers may result in "Atypical/Indeterminate" answer which will be displayed on the screen. The operator then has the option to reset and change some of the answers, which may result in a localization site.

Figure 33:
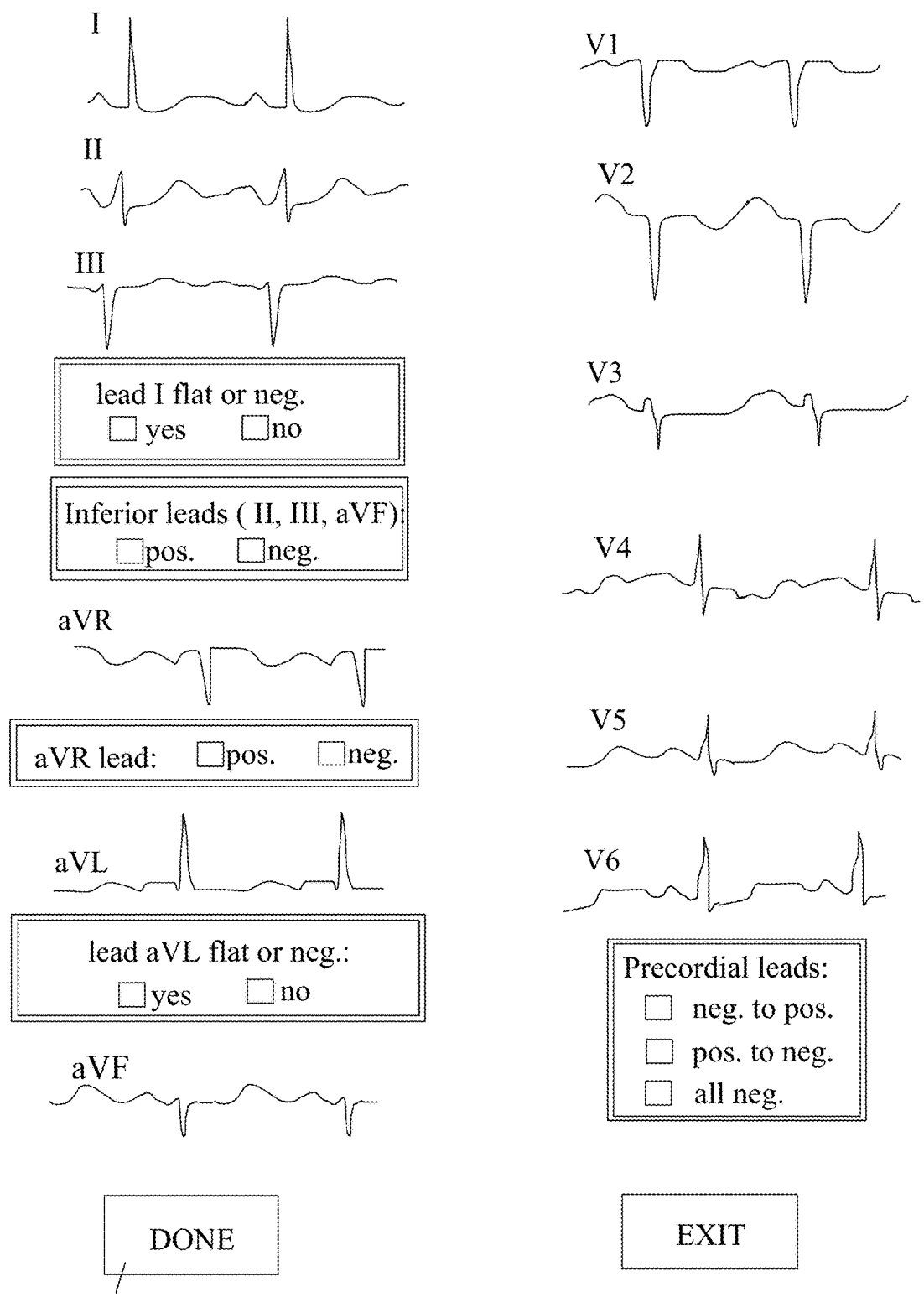
FIG. 33 shows another example of screen for the EKG localization program.

It will be clear to one skilled in the art that various modifications of the above can be implemented and are considered within the scope of the disclosure. For example, one modification of this implementation is shown in FIG. 33. As shown in the figure, once the answers to all the questions are checked off, the physician or operator clicks on the Done 318 button. This takes the program to an answer screen, where the EKG localization site is stated and any explanation is detailed.

Figure 34:
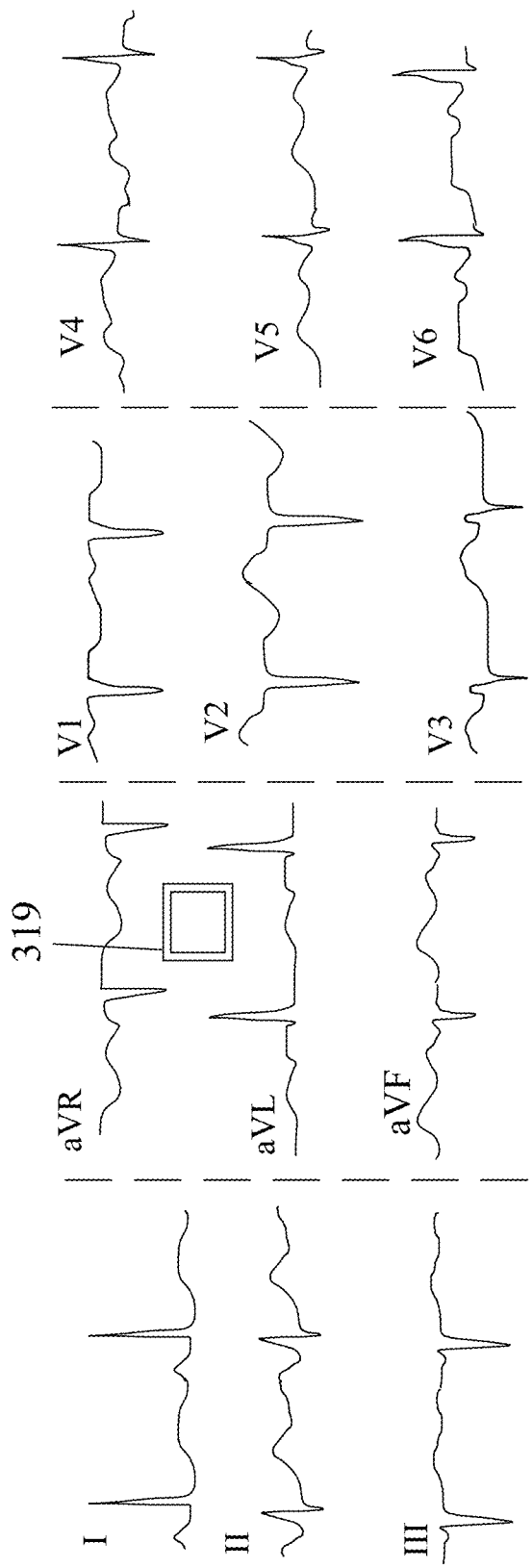
FIGS. 34 and 35 shown more examples of "interactive" EKG localization program.
Figure 35:
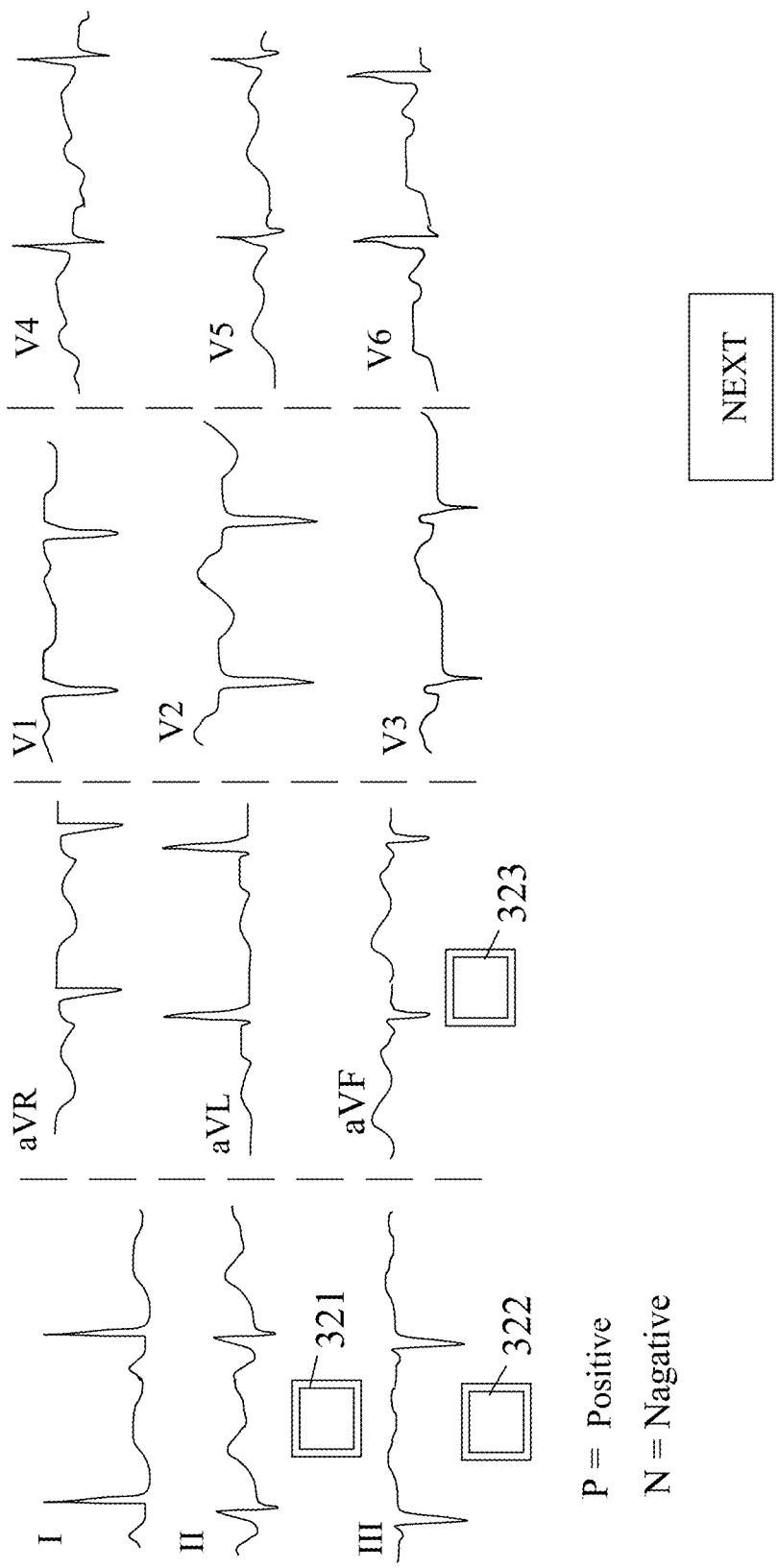
Figure 36:
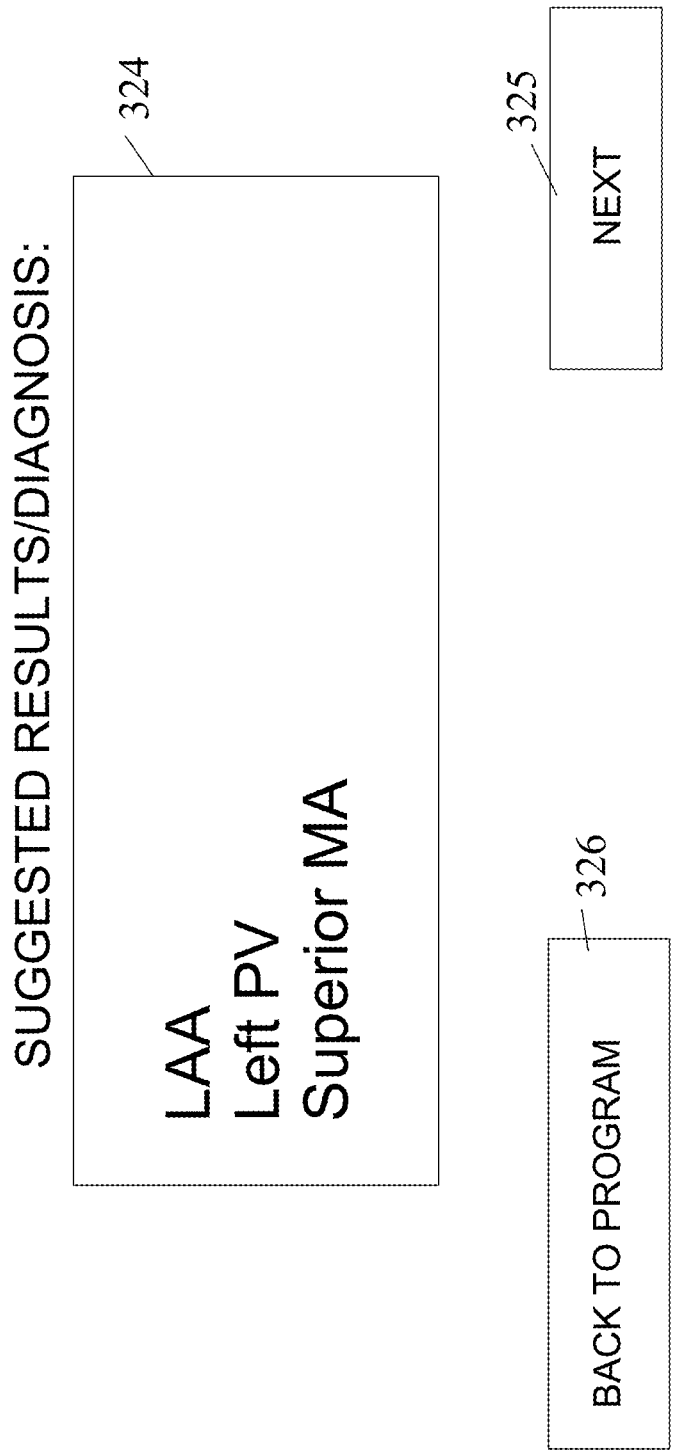
FIG. 36 shows a menu screen for the EKG localization program.

Yet another example of implementation is shown in conjunction with FIGS. 34-36. As shown in FIG. 34, as the screen appears on the display, the physician or operator answers the question about lead aVR 319 and clicks Next 320. Shown in FIG. 35, the operator then answers questions on Lead II 321, Lead III 322, and Lead aVF 323, then clicks on Next. As shown in FIG. 36, the suggested Results/diagnosis are displayed, and the operator has the option to move forward in the program by clicking Next 325 or going back in the program by clicking Back to Program 326 button. Various other modifications and combinations of these examples can be implemented, and are considered within the scope of this disclosure.

The present disclosure may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the disclosure.

The invention claimed is:

1. A method of identifying or measuring the zone of slow conduction, in a cardiac ablation procedure, comprising:
   providing a computer based system with hardware and software wherein, the software comprises algorithm(s) capable of identifying or measuring the zone of slow conduction in a cardiac atrial flutter ablation procedure, said algorithm(s) are coupled with a patient's cardiac signals;
   providing fluoroscopy;
   providing intracardiac and surface signals into said computer based system wherein, said intracardiac signals include atrial intracardiac signals;
   utilizing a fluoroscopy based system which utilizes fluoroscopy for manipulating ablation catheter, analyzing said patient's cardiac signals with said algorithm(s) wherein, said algorithm(s) comprise methods for measuring the quantification of zone of slow conduction by measuring relative timing information between signals from ablation catheter and said atrial intracardiac signals to determine and indicate the zone of slow conduction, wherein said quantification is based on centering signals from ablation catheter between two consecutive atrial intracardiac signals; and
   displaying analyzed signals on a monitor showing the result of the quantified zone of slow conduction during the cardiac atrial flutter ablation procedure wherein, placed indicators on said monitor are activated to aid in said cardiac atrial flutter ablation procedure, said indicators indicating a desirable site to ablate, or a non-desirable site to ablate, or a site in-between desirable and non-desirable site, wherein said indicators are color coded.

2. The method of claim 1, wherein said cardiac ablation procedure is performed for one of typical atrial flutter arrhythmias, atypical artial arrhythmias or atrial or ventricular reentrant arrhythmias.

3. The method of claim 1, wherein said algorithms utilize timing analysis of intracardiac signals and the relationship between said atrial intracardiac signals and ablation catheter signals.

4. The method of claim 1, wherein said quantifying and displaying zone of slow conduction in a cardiac ablation procedure is automated.

5. The method of claim 1, wherein said method can be incorporated into an electrophysiology (EP) mapping, electrophysiology (EP) recording or an ablation generator system.

6. The method of claim 1, wherein said algorithm(s) may be combined with a program configured for an electrophysiology (EP) data recording system or with a program used in a mapping system for cardiac ablations.

7. The method of claim 1, wherein said quantifying and displaying zone of slow conduction is automated by voice command.

8. A system for identifying, or measuring, or checking at least one of zone of slow conduction, or line of block in cardiac atrial flutter ablations, comprising:
   a computer based mapping system utilizing fluoroscopy image and cardiac signals, wherein said mapping system comprises hardware and software comprising algorithm(s) and wherein said mapping system utilizes fluoroscopy for manipulating ablation catheter;
   said algorithm(s) capable of identifying, or measuring, or checking zone of slow conduction in cardiac atrial flutter ablations, based upon utilizing timing analysis of intracardiac signals and the relationship between atrial based intracardiac signals and signals from ablation catheter wherein, said algorithm(s) comprise quantifying and displaying zone of slow conduction by measuring relative timing information between signals from ablation catheter and said atrial based intracardiac signals based on centering from two consecutive said intracardiac signals;
   said computer coupled with said algorithm(s); and
   display means for displaying on a monitor measured and quantified zone of slow conduction, or line of block in cardiac atrial flutter ablations wherein, placed indicators on said monitor are activated to aid in said cardiac atrial flutter ablation, said indicators indicating a desirable site to ablate, or a non-desirable site to ablate, or a site in-between desirable and non-desirable site, wherein said indicators are color coded.

9. The system of claim 8, wherein said cardiac ablation is performed for one of typical atrial flutter arrhythmias, atypical artial arrhythmias or atrial or ventricular reentrant arrhythmias.

10. The system of claim 8, wherein said quantifying and displaying zone of slow conduction is automated.

11. The system of claim 8, wherein said quantifying and displaying zone of slow conduction is automated by voice command.

12. The system of claim 8, wherein said algorithm(s) can be written in part or its entirety in at least one of, LAB WINDOWS/CVI®, LABVIEW® (NATIONAL INSTRUMENTS CORP.), C, MICROSOFT® VISUAL C++®, DOT NET FRAMEWORK®, MATLAB®, MICROSOFT VISUAL BASIC®, PYTHON®, or a software language used for writing medical programs or algorithms.

13. The system of claim 8, wherein said system can be incorporated into an electrophysiology (EP) mapping system, electrophysiology (EP) recording system or an ablation generator system.

14. The system of claim 8, wherein said algorithm(s) may be combined with a program configured for electrophysiology (EP) data analysis or data recording or with a program used in a mapping system for cardiac ablations.

15. A method of guiding a physician for ablating in the zone of slow conduction within isthmus of the heart, comprising:
 providing a computer based mapping system for acquiring cardiac signals and imaging wherein said system comprises hardware and software, wherein said software comprising algorithm(s) for quantifying and displaying a zone of slow conduction in atrial flutter ablations;
 utilizing said algorithms wherein said algorithm(s) comprise measuring zone of slow conduction by measuring relative timing information and centering between signals from ablation catheter and two consecutive intracardiac reference signals;
 determining zone of slow conduction during ablation procedure wherein, said zone of slow conduction is measured and quantified utilizing said two consecutive intracardiac reference signals; and
 displaying analyzed or measured results, whereby providing guidance or visual guidance for ablating in the zone of slow conduction within the isthmus of the heart for cardiac atrial flutter ablations wherein, placed indicators on a monitor are activated to aid in said cardiac atrial flutter ablations, said indicators indicating a desirable site to ablate, or a non-desirable site to ablate, or a site in-between desirable and non-desirable site, wherein said indicators are color coded.

16. The method of claim 15, wherein said guidance is for atrial flutter arrhythmia ablations performed using radio frequency or cryogenic ablation techniques.

17. The method of claim 15, wherein said identification of said zone of slow conduction is further based upon timing the midpoint of said two consecutive intracardiac reference signals and its relationship to the timing of said ablation catheter.

18. The method of claim 15 wherein, said method can be incorporated into a stand-alone computer, an electrophysiology (EP) mapping system, an electrophysiology (EP) recording system or an ablation generator system.

19. The method of claim 15, wherein said identification of said zone of slow conduction is further color coded for visual guidance.

20. The method of claim 15, wherein said identification of said zone of slow conduction is automated.

* * * * *